US008288100B2

(12) United States Patent
Lo et al.

(10) Patent No.: US 8,288,100 B2
(45) Date of Patent: Oct. 16, 2012

(54) METHODS FOR DETECTING FETAL DNA IN A PLASMA OR SERUM SAMPLE FROM A PREGNANT WOMAN

(75) Inventors: Yuk Ming Dennis Lo, Kowloon (HK); Rossa Wai Kwun Chiu, New Territories (HK); Stephen Siu Chung Chim, Quarry Bay (HK); Chunming Ding, New Territories (HK); Kwan Chee Chan, Kowloon (HK); Hing Nam Ivy Wong, New Territories (HK); Ka Chun Ryan Yuen, New Territories (HK)

(73) Assignee: The Chinese University of Hong Kong, Hong Kong, SAR (CN)

( * ) Notice: Subject to any disclaimer, the term of this patent is extended or adjusted under 35 U.S.C. 154(b) by 0 days.

(21) Appl. No.: 12/791,776

(22) Filed: Jun. 1, 2010
(Under 37 CFR 1.47)

(65) Prior Publication Data

US 2011/0143342 A1 Jun. 16, 2011

Related U.S. Application Data

(62) Division of application No. 11/784,501, filed on Apr. 6, 2007, now Pat. No. 7,754,428.

(60) Provisional application No. 60/797,506, filed on May 3, 2006.

(51) Int. Cl.
*C12Q 1/68* (2006.01)
*C07H 21/02* (2006.01)
*C07H 21/04* (2006.01)

(52) U.S. Cl. ...... 435/6.11; 435/6.1; 435/6.12; 435/91.2; 536/23.5

(58) Field of Classification Search .................. None
See application file for complete search history.

(56) References Cited

U.S. PATENT DOCUMENTS

| 2004/0137470 A1* | 7/2004 | Dhallan ............................ 435/6 |
| 2005/0153316 A1* | 7/2005 | Jeddeloh et al. .................. 435/6 |
| 2006/0051768 A1 | 3/2006 | Hoon et al. |

FOREIGN PATENT DOCUMENTS

| WO | WO 03/020974 A2 | 3/2003 |
| WO | WO 2005/118852 A2 | 12/2005 |
| WO | WO 2005/118852 A3 | 12/2005 |

OTHER PUBLICATIONS

Chim et al. PNAS. 2005. 102: 14753-14758. available online Oct. 3, 2005.*
Chiu et al. The American Journal of Pathology. Mar. 2007. 170: 941-950.*
Bianchi et al. Clinical Chemistry. 2001. 47: 1867-1869.*
Lun et al. Clinical Chemistry. 2007. 53: 796-798.*
Illanes et al. Prenatal Diagnosis. 2006. 26: 1216-1218.*
Majer et al. Prenatal Diagnosis. 2007. 27: 1219-1223.*
Lo et al. The New England Journal of Medicine. 1998. 339: 1734-1738).*
Muller et al. Clinical Chemistry. 2004. 50: 1065-1068.*
Eads et al. Nucleic Acids Research. 2000. 28 (8): E3.*
International Search Report from PCT/GB2007/001625, dated Jul. 12, 2007.
Battagli et al.; "Promoter Hypermethylation of Tumor Suppressor Genes in Urine from Kidney Cancer Patients"; 2003, *Cancer Research*, vol. 63, pp. 8695-8699.
Bianchi et al.; "Large Amounts of Cell-free Fetal DNA are Present in Amniotic Fluid"; 2001, *Clinical Chemistry*, vol. 47, pp. 1867-1869.
Chan et al.; "Hypermethylated *RASSF/A* in Maternal Plasma: A Universal Fetal DNA Marker that Improves the Reliability of Noninvasive Prenatal Diagnosis"; 2006, *Clinical Chemistry*, vol. 52, No. 12, pp. 2211-2218.
Chim et al.; "*SOCS1* and *SHP1* hypermethylation in multiple myeloma: implications for epigenetic activation of the Jak/STAT pathway"; 2004, *Blood*, vol. 103, No. 12, pp. 4630-4635.
Chiu et al.; "Hypermethylation of of *RASSF1A* in Human and Rhesus Placentas"; 2007, *The American Journal of Pathology*, vol. 170, No. 3, pp. 941-950.
Eads et al.; "MethylLight: a high-throughput assay to measure DNA methylation"; 2000, *Nucleic Acids Research*, vol. 28, No. 8, pp. E32.
Hara et al.; "Dynamic Changes in the Expression of Protein Tyrosine Phosphatases During Preimplantation Mouse Development: Semi-Quantification by Real-Time PCR"; 2003, *Journal of Reproduction and Development*, vol. 49, No. 4, pp. 323-328.
Illanes et al.; "Detection of cell-free fetal DNA in maternal urine"; 2006, *Prenatal Diagnosis*, vol. 26, pp. 1216-1218.
Lee et al.; "Down syndrome and cell-free fetal DNA in archived maternal serum"; 2002, *Am. J. Obstet. Gynecol.*, vol. 187, pp. 1217-1221.
Leung et al.; "Increased Maternal Plasma Fetal DNA Concentrations in Women who Eventually Develop Preeclampsia"; 2001, *Clinical Chemistry*, vol. 47, pp. 137-139.
Lo et al.; "Prenatal Diagnosis of Fetal RhD Status by Molecular Analysis of Maternal Plasma"; 1998, *The New England Journal of Medicine*, vol. 339, pp. 1734-1738.
Lo et al.; "Presence of fetal DNA in maternal plasma and serum"; 1998, *Transfusion Medicine Reviews*, vol. 12, No. 2, p. 146.
Lun et al.;"Epigenetic Analysis of *RASSF1A* Gene in Cell-Free DNA in Amniotic Fluid"; 2007, *Clinical Chemistry*, vol. 53, pp. 796-798.
Majer et al.; "Maternal urine for prenatal diagnosis—an analysis of cell-free fetal DNA in maternal urine and plasma in the third trimester"; 2007, *Prenatal Diagnosis*, vol. 27, pp. 1219-1223.
Müller et al.; "DNA Methylation Changes in Sera of Women in Early Pregnancy Similar to Those in Advanced Breast Cancer Patients"; 2004, *Clinical Chemistry*, vol. 50, pp. 1065-1068.
Nishiyama et al.; "A DNA Repeat, NBL2, is Hypermethylated in Some Cancers by Hypomethylated in Others"; 2005, *Cancer Biology and Therapy*, vol. 4, pp. 440-448.

\* cited by examiner

*Primary Examiner* — Carla Myers
(74) *Attorney, Agent, or Firm* — Kilpatrick Townsend & Stockton LLP

(57) ABSTRACT

This application describes the discovery that, in a pregnant woman, certain genes (such as RASSF1A, APC, CASP8, RARB, SCGB3A1, DAB2IP, PTPN6, THY1, TMEFF2, and PYCARD) originated from a fetus are highly methylated, whereas the same genes of maternal origin are unmethylated. This discovery allows the easy detection of one or more of these methylated fetal genes in a biological sample from a pregnant woman, serving as a universal indicator of the presence of fetal DNA in the sample. These fetal methylation markers are particularly useful as positive controls for a non-invasive analytical process during which the quality and quantity of fetal DNA are monitored. These newly identified fetal markers can also be measured directly for diagnosis of certain pregnancy-related conditions.

22 Claims, 40 Drawing Sheets

| Oligo | Sequence (5' to 3') | Product length (bp) | Citation (if any) |
|---|---|---|---|
| Methylation-specific PCR | | | |
| RASSF1A-MF | GTGTTAACGCGTTGCGTATC | 82 | Lo, K. W. et al |
| RASSF1A-MR | AACCCCGCGAACTAAAAACGA | | Cancer Res 61, |
| RASSF1A-UF | TTTGGTTGGAGTGTGTTAATGTG | 94 | 3877-81 (2001). |
| RASSF1A-UR | CAAACCCCACAAACTAAAAACAA | | |
| Bisulfite sequencing (human) | | | |
| RASSF1A | | | |
| HsPromoter-F | GGGTTTTATAGTTTTTGTATTTAGGTTTTT | 201 | |
| HsPromoter-R | CAACTCAATAAACTCAAACTCCCCC | | |
| HsExon1-F | GGGGAGTTTGAGTTTATTGAGTTG | 297 | |
| HsExon1-R | CTACCCCTTAACTACCCCTTCC | | |
| APC | | | |
| HsPromoter-F | TAATTTATTTAATATTATTGTTTTTTTGTGTTGT | 414 | |
| HsPromoter-R | CACCCTAACRAACTACACCAATACAA | | |
| RARB | | | |
| HsRARBPromoter-F | GTAGGYGGAATATYGTTTTTTAAGTTAAGT | 378 | |
| HsRARBPromoter-R | ACTTCCTACTACTTCTATCACACAAAATAAAA | | |
| HsRARBExon1-F | TTTTATTTTGTGTGATAGAAGTAGTAGGAAGT | 290 | |
| HsRARBExon1-R | AATCATTTACCATTTTCCAAACTTACTC | | |

Notes on oligo suffix, sequence prefix and suffix:
 F    Forward primer
 R    Reverse primer Reaction conditions and thermal profile for bisulfite PCR of human *RASSF1A* promoter and exon 1

| | Final | | | |
|---|---|---|---|---|
| 10X Buffer II | 1X | 95°C | 10 min | |
| MgCl₂ | 3.0mM | 95°C | 40 sec | |
| dNTP | 200μM | 57°C | 45 sec | x 40 cycles |
| Forward primer | 200nM | 72°C | 45 sec | |
| Reverse primer | 200nM | 72°C | 7 min | |
| AmpliTaq Gold | 1U | | | |
| Bisulfite converted DNA | 80ng | | | |
| Total reaction volume | 25μl | | | |

Reaction conditions and thermal profile for bisulfite PCR of human *APC* promoter

| | Final | | | |
|---|---|---|---|---|
| 10X Buffer II | 1X | 95°C | 10 min | |
| MgCl₂ | 3.0mM | 95°C | 40 sec | |
| dNTP | 300μM | 57°C | 1 min | x 45 cycles |
| Forward primer | 400nM | 72°C | 40 sec | |
| Reverse primer | 400nM | 72°C | 7 min | |
| AmpliTaq Gold | 1U | | | |
| Bisulfite converted DNA | 120ng | | | |
| Total reaction volume | 25μl | | | |

Reaction conditions and thermal profile for bisulfite PCR of human *RARB* promoter and exon 1

| | Final conc | | | |
|---|---|---|---|---|
| 10X Buffer II | 1X | 95°C | 10 min | |
| MgCl₂ | 3.0mM | 95°C | 40 sec | |
| dNTP | 200μM | 57°C | 1 min | x 40 cycles |
| Forward primer | 200nM | 72°C | 40 sec | |
| Reverse primer | 200nM | 72°C | 7 min | |
| AmpliTaq Gold | 1U | | | |
| Bisulfite converted DNA | 80ng | | | |
| Total reaction volume | 25μl | | | |

Fig. 1

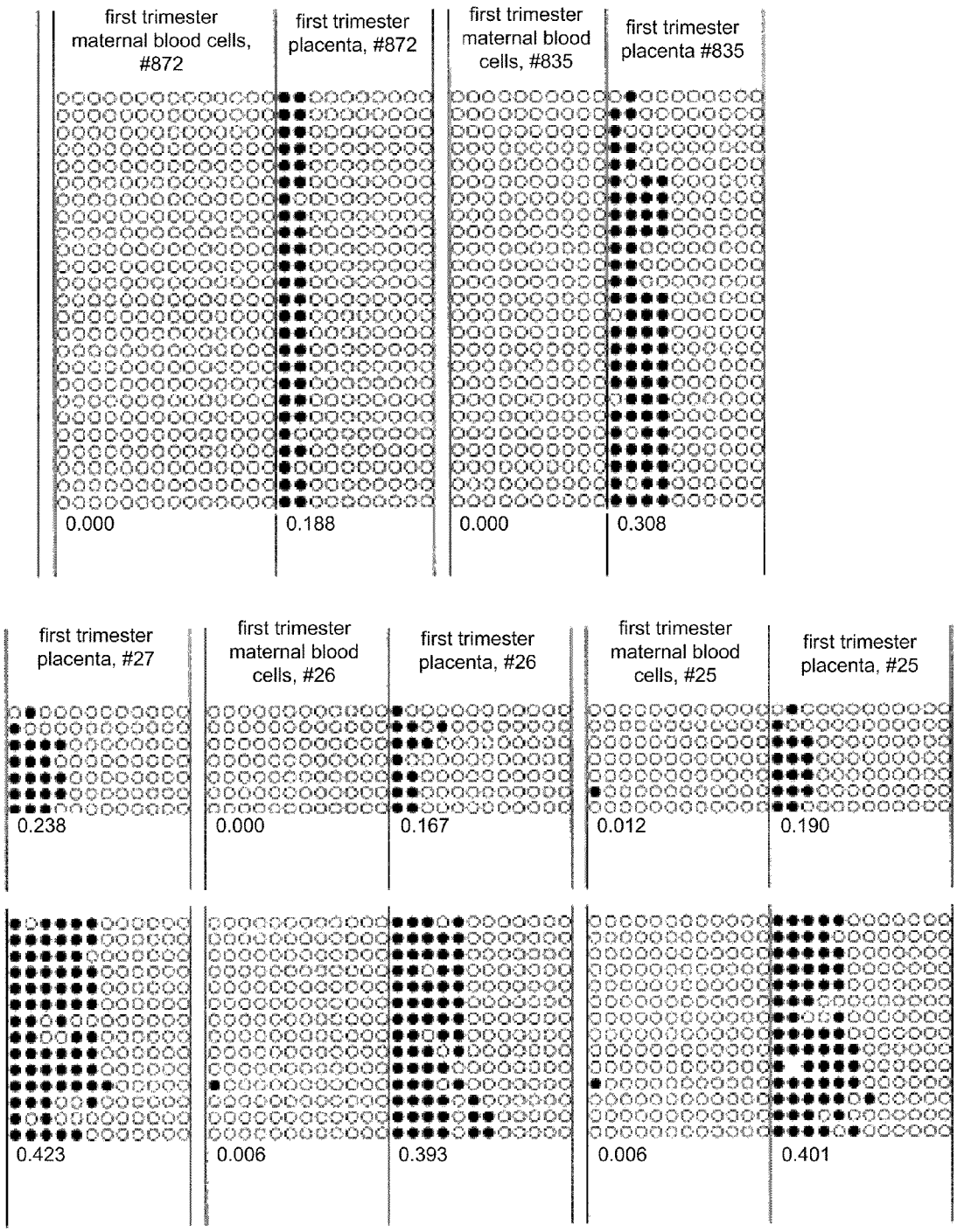
Fig. 3 Part 1

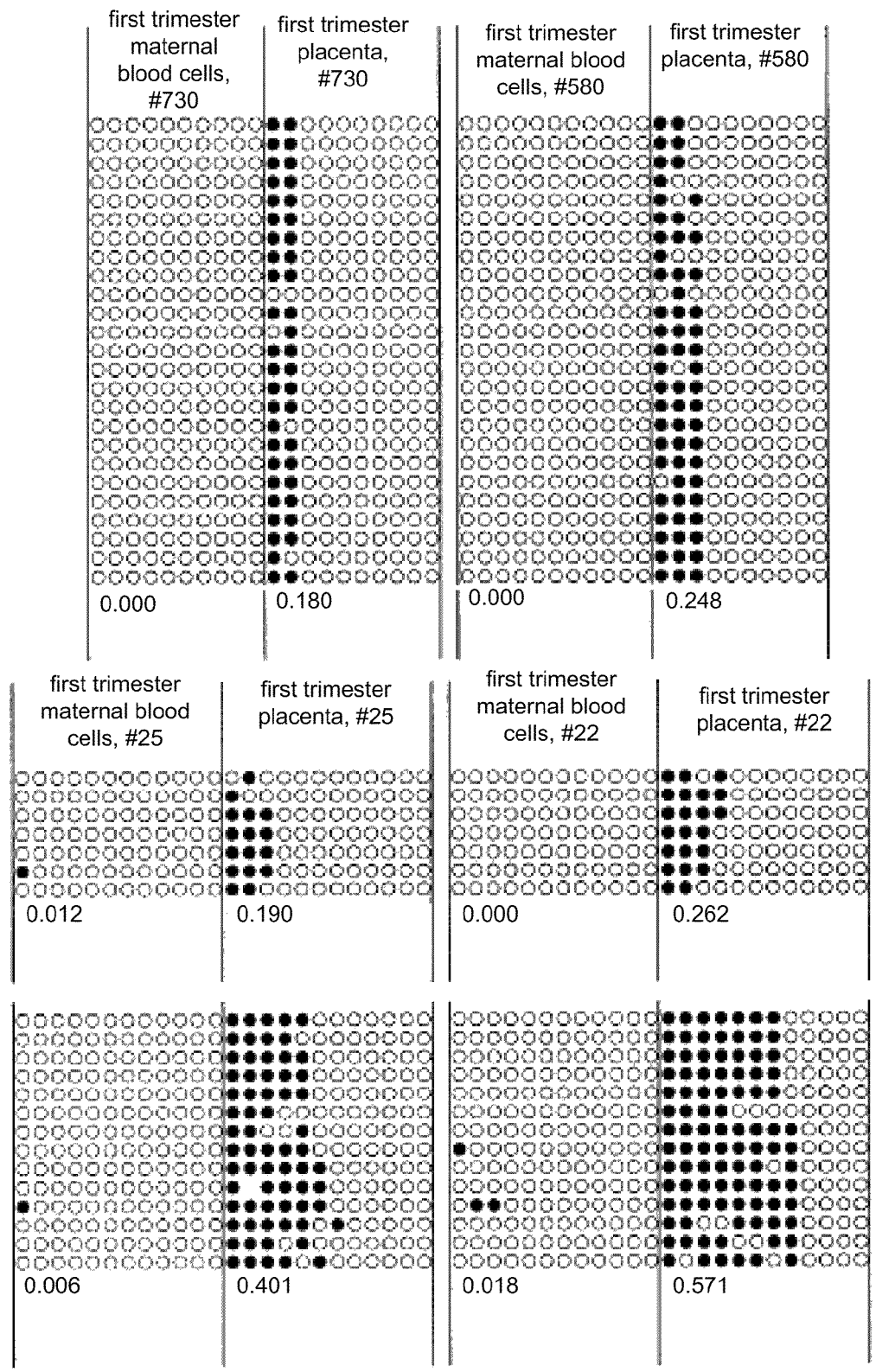
Fig. 3 Part 1 (cont'd)

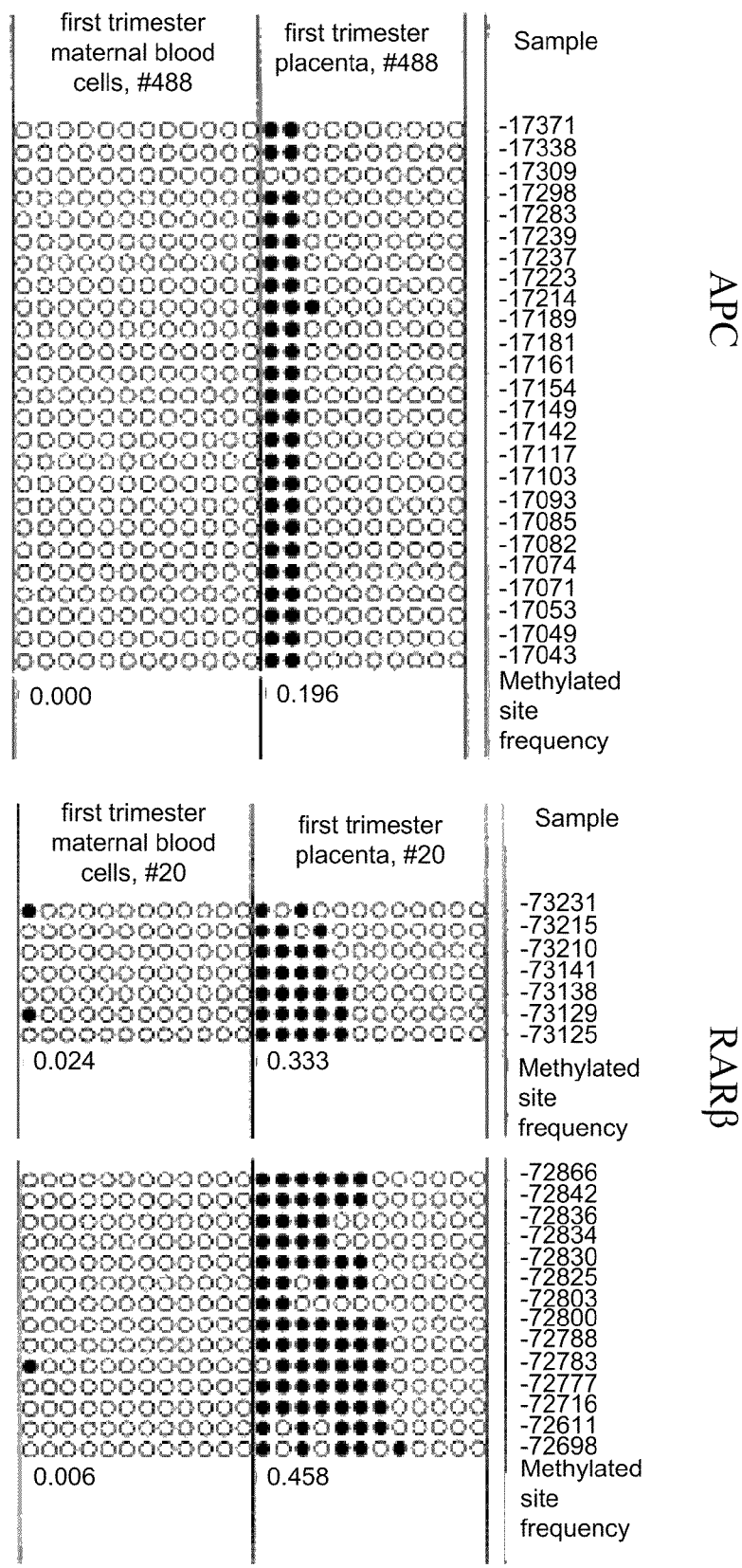
Fig. 3 Part 1 (cont'd)

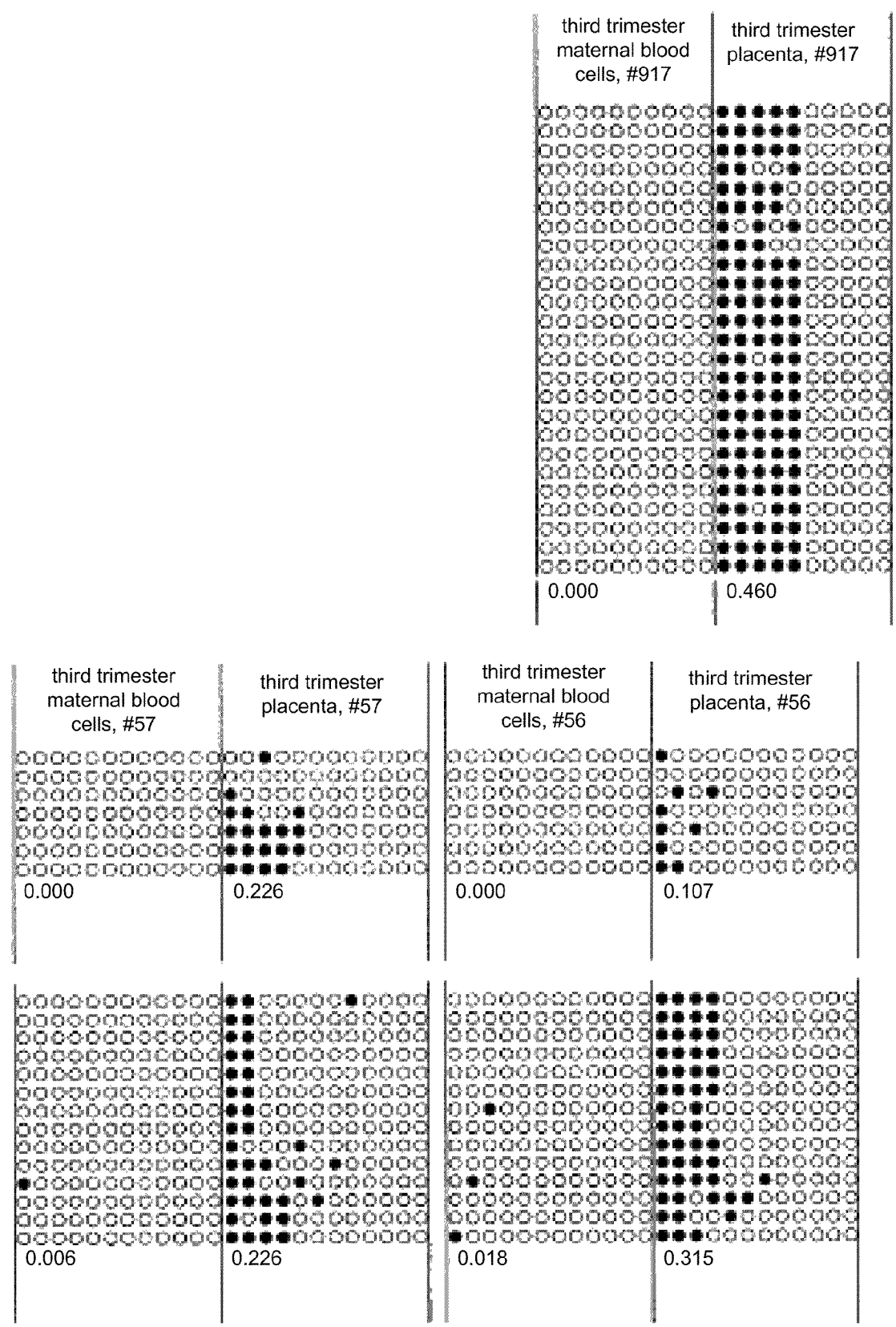
Fig. 3 Part 2

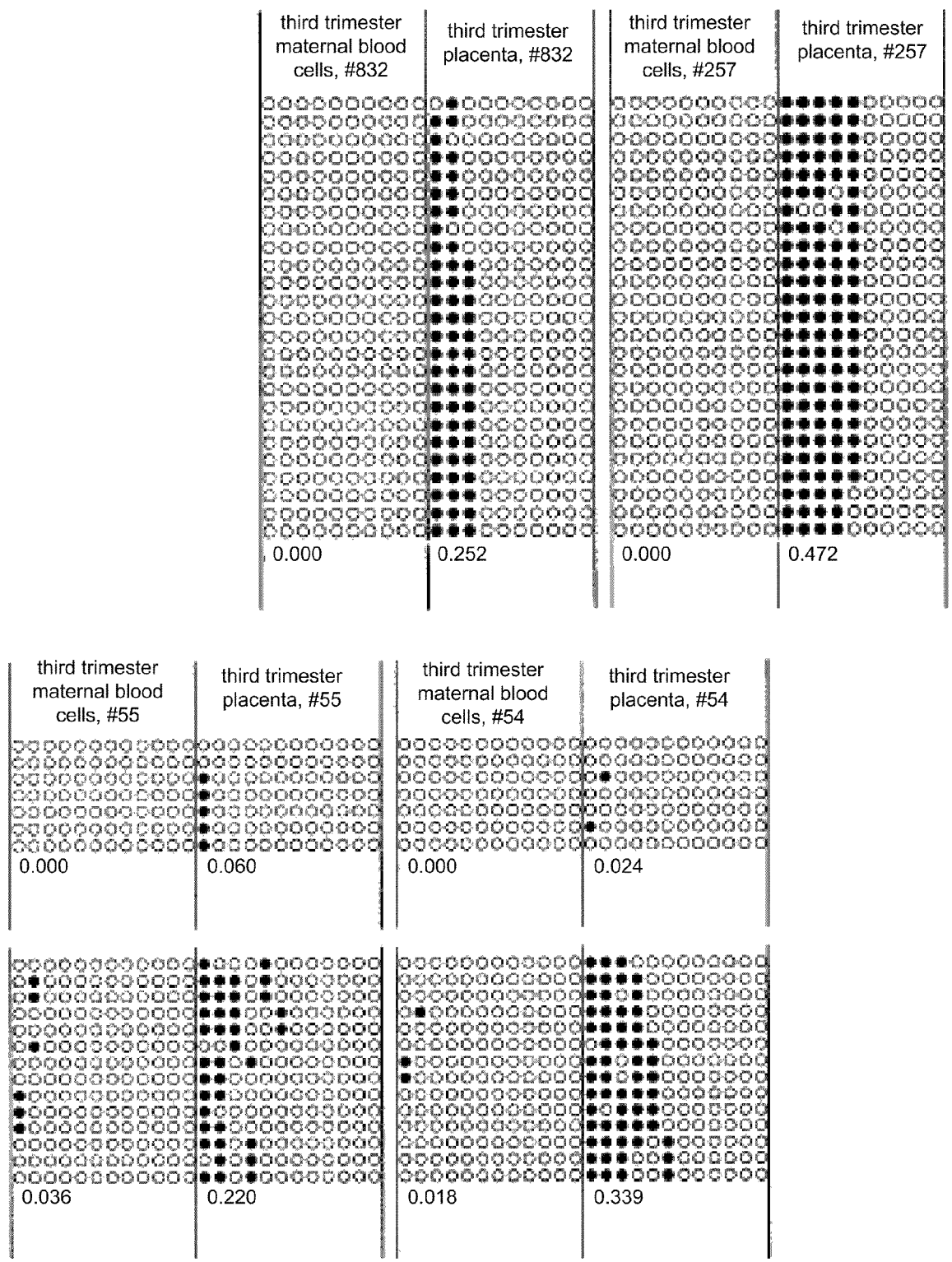
Fig. 3 Part 2 (cont'd)

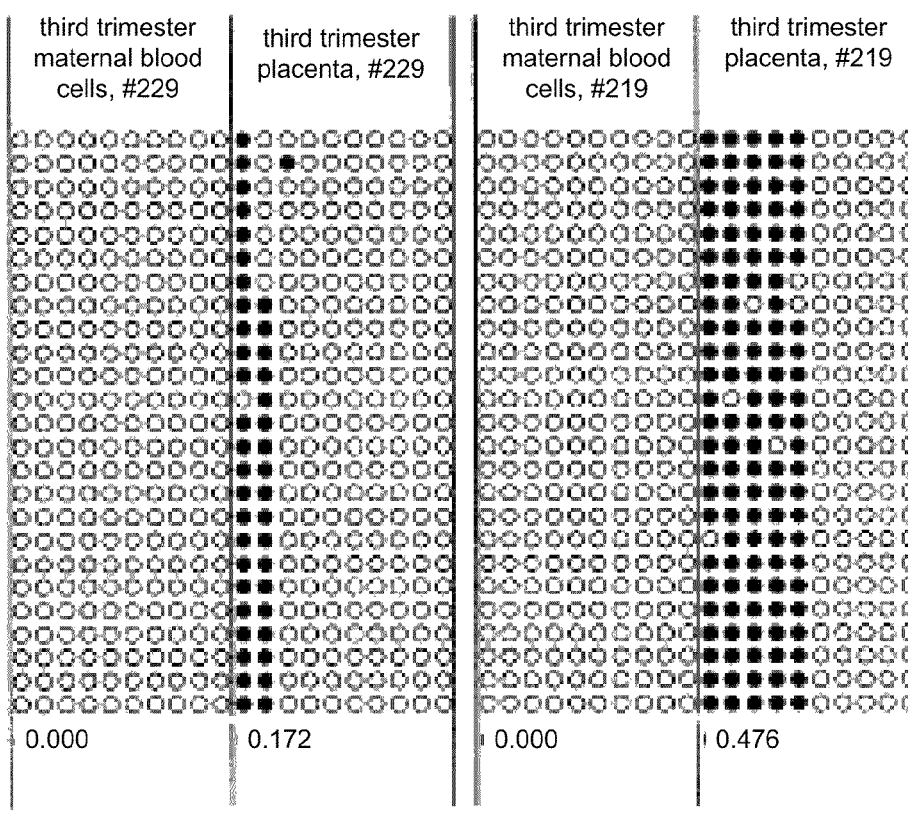
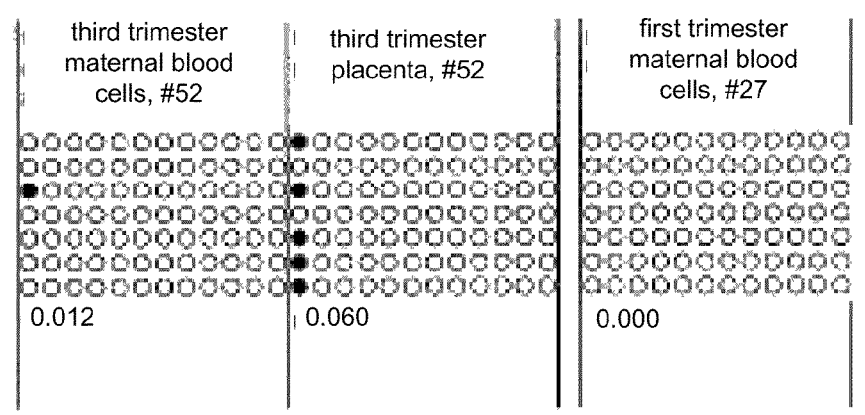
Fig. 3 Part 2 (cont'd)

Figure 4

Methylation-specific PCR

| Oligo | Sequence (5' to 3') | Product length (bp) |
|---|---|---|
| CASP8-MF | GGTTAGGGGATTCGGAGATTGC | 331 |
| CASP8-MR | AAAAAACCGTATATCTACATTCGAAACG | |

Bisulfite sequencing (human)

*CASP8*

| | | |
|---|---|---|
| HsExon1-F | ACGGAAGTGTTTTTATAGGTTTTT | 269 |
| HsExon1-R | ATAATTCCTATTAAAAACCACCTTAA | |

Notes on oligo suffix, sequence prefix and suffix:

F    Forward primer
R    Reverse primer

Reaction conditions and thermal profile for bisulfite PCR of human CASP8 exon 1

| | Final | | |
|---|---|---|---|
| 10X Buffer II | 1X | 95°C | 10 min |
| MgCl₂ | 3.0mM | 95°C | 40 sec |
| dNTP | 200µM | 57°C | 40 sec  } x 40 cycles |
| Forward primer | 200nM | 72°C | 40 sec |
| Reverse primer | 200nM | 72°C | 7 min |
| AmpliTaq Gold | 1U | | |
| Bisulfite converted DNA | 80ng | | |
| *Total reaction volume* | *25 µl* | | |

Figure 6

| Oligo | Sequence (5' to 3') | Product length (bp) | Citation (if any) |
|---|---|---|---|

Methylation-specific PCR

| | | | |
|---|---|---|---|
| SCGB3A1-MF | TTTAGTTTTGTAGGGGGTGTGC | 195 | |
| SCGB3A1-MR | ACCAACTTCCTACTACGACCGACG | | |

Bisulfite sequencing (human)

SCGB3A1

| | | | |
|---|---|---|---|
| Hspromoter-F | GATTAGAGGTAGGGATTAGGGAGTT | 200 | |
| Hspromoter-R | TAACAAACRCTAAAACCCTCTAAA | | |

Notes on oligo suffix, sequence prefix and suffix:

F    Forward primer
R    Reverse primer

Reaction conditions and thermal profile for bisulfite PCR of human SCGB3A1 promoter

| | Final | | |
|---|---|---|---|
| 10X Buffer II | 1X | 95°C | 10 min |
| MgCl₂ | 3.0 mM | 95°C | 40 sec |
| dNTP | 200 μM | 57°C | 40 sec | × 40 cycles
| Forward primer | 200 nM | 72°C | 40 sec |
| Reverse primer | 200 nM | 72°C | 7 min |
| AmpliTaq Gold | 1U | | |
| Bisulfite converted DNA | 80 ng | | |
| Total reaction volume | 25 μl | | |

Selective amplification of methylated DNA sequences

Complete digestion

Selective amplification of fetal-derived *Rsf*
No detectable $\beta$-actin signal Non-specific amplification of maternal- and fetal-derived Rsf
β-*actin* signal detectable

Figure 17

Oligo        Sequence (5' to 3')        Product length (bp)    Citation (if any)

Methylation-specific PCR

| Oligo | Sequence (5' to 3') | Product length (bp) | Citation (if any) |
|---|---|---|---|
| DAB2IP-MF | GTAAGGGTGCGGGTTTCGC | 230 | |
| DAB2IP-MR | GAACTCACCTCTCATTATCCGCG | | |

Bisulfite sequencing (human)

*DAB2IP*

| Oligo | Sequence (5' to 3') | Product length (bp) | Citation (if any) |
|---|---|---|---|
| HsExon1-F | AAGGGTTTTATTAAGYGTATTAAGAGTT | 313 | |
| HsExon1-R | ACCCCRAAAAAAAAACACAAA | | |

Notes on oligo suffix, sequence prefix and suffix:
F   Forward primer
R   Reverse primer

Reaction conditions and thermal profile for bisulfite PCR of human DAB2IP exon 1

| | Final |
|---|---|
| 10X Buffer II | 1X |
| MgCl₂ | 2.0 mM |
| dNTP | 200 µM |
| Forward primer | 200 nM |
| Reverse primer | 200 nM |
| AmpliTaq Gold | 1 U |
| Bisulfite converted DNA | 80 ng |
| *Total reaction volume* | *25 µl* |

| | | |
|---|---|---|
| | 95°C | 10 min |
| | 95°C | 40 sec |
| | 57°C | 40 sec | x 40 cycles
| | 72°C | 40 sec |
| | 72°C | 7 min |

METHODS FOR DETECTING FETAL DNA IN A PLASMA OR SERUM SAMPLE FROM A PREGNANT WOMAN

RELATED APPLICATIONS

This application is a division of U.S. patent application Ser. No. 11/784,501, filed Apr. 6, 2007, now U.S. Pat. No. 7,754, 428, which claims priority to U.S. Provisional Patent Application Ser. No. 60/797,506, filed May 3, 2006, the contents of both of which are hereby incorporated by reference in the entirety for all purposes.

BACKGROUND OF THE INVENTION

Early detection of pregnancy-related conditions, including potential complications during pregnancy or delivery and genetic defects of the fetus is of crucial importance, as it allows early medical intervention necessary for the safety of both the mother and the fetus. Prenatal diagnosis has been routinely conducted using cells isolated from the fetus through procedures such as chorionic villus sampling (CVS) or amniocentesis. These conventional methods are, however, invasive and present an appreciable risk to both the mother and the fetus despite most careful handling (Tabor et al., *Lancet* 1:1287-1293, 1986).

Alternatives to these invasive approaches have been developed for prenatal screening, e.g., to detecting fetal abnormalities, following the discoveries that several types of fetal cells can be found in maternal circulation (Johansen et al., *Prenat. Diagn.* 15:921-931, 1995) and more importantly, circulating cell-free fetal DNA can be detected in maternal plasma and serum (Lo et al., *Lancet* 350:485-487, 1997). The amount of fetal DNA in maternal blood has been shown to be sufficient for genetic analysis without complex treatment of the plasma or serum, in contrast to alternative methods requiring steps for isolating and enriching fetal cells. Fetal rhesus D (RhD) genotyping (Lo et al., *N. Engl. J. Med.* 339:1734-1738, 1998), fetal sex determination (Costa et al., *N. Engl. J. Med.* 346:1502, 2002), and diagnosis of several fetal disorders (Amicucci et al., *Clin. Chem.* 46:301-302, 2000; Saito et al., *Lancet* 356: 1170, 2000; and Chiu et al., *Lancet* 360:998-1000, 2002) have since been achieved by detecting fetal DNA in maternal plasma or serum using a polymerase chain reaction (PCR)-based technique.

In addition, quantitative abnormalities of fetal DNA in maternal plasma/serum have been reported in preeclampsia (Lo et al., *Clin. Chem.* 45:184-188, 1999 and Zhong et al., *Am. J. Obstet. Gynecol.* 184:414-419, 2001), fetal trisomy 21 (Lo et al., *Clin. Chem.* 45:1747-1751, 1999 and Zhong et al., *Prenat. Diagn.* 20:795-798, 2000) and hyperemesis gravidarum (Sekizawa et al., *Clin. Chem.* 47:2164-2165, 2001). Detection of fetal nucleic acid in maternal blood for prenatal genetic analysis is also disclosed in U.S. Pat. No. 6,258,540.

Because fetal DNA co-exists with maternal DNA in the acellular portion of a pregnant woman's blood, e.g., serum or plasma, there is a need to distinguish DNA from fetal origin and maternal origin to ensure accurate results in fetal DNA-based diagnosis. It was first disclosed in U.S. patent application Ser. No. 09/944,951, published as 20030044388, that fetal and maternal DNA may be distinguished by their different methylation profiles. Landes et al. in U.S. Patent Application Publication No. 20030211522 also proposed differential methylation markers may be used for prenatal diagnosis. On the other hand, to ensure the efficacy of fetal DNA-based testing methods and to eliminate erroneous interpretation of test results due to insufficient recovery of fetal DNA obtained from such methods, there also exists a need for determining the presence and quantity of fetal DNA in a sample used for the testing procedure. It is therefore desirable to identify a fetal DNA marker that can effectively serve as a universal indicator of the presence or absence of fetal DNA in general in a test sample. It is important that such a fetal DNA marker is consistently and uniformly distinct from its maternal counterpart, and that the presence or absence of the marker can be readily determined over the background of maternal DNA and directly correlated with the presence or absence of fetal DNA in general. This invention addresses this and other related needs.

In this application, a number of human genes have been identified for the first time as those having highly distinct methylation patterns in fetal tissues (e.g., derived from placenta) and in maternal tissues. Originated from a fetus, these genes are methylated at a high level of uniformity, whereas the genes from a maternal source that releases significant amount of cell-free DNA into the maternal blood are unmethylated at a similarly high level of uniformity. These features allow the genes to effectively serve as internal positive controls of a test sample used in a prenatal diagnostic process, for the purpose of ensuring that a sufficient amount of fetal DNA has been recovered in the sample during the process. Because of the high level of uniformity in these genes' methylation status with regard to their origin, these genes are particularly reliable controls, indicative of both quality and quantity of the fetal DNA. Another advantage of these genes as fetal markers is the relative ease in detecting only the methylated fetal version in contrast to their unmethylated maternal counterparts. Furthermore, the fetal genes described in this application can also be used directly as diagnostic markers for certain conditions or disorders related to pregnancy.

BRIEF SUMMARY OF THE INVENTION

In the first aspect of this invention, a method is provided for detecting fetal DNA in a biological sample from a pregnant woman. This method comprises the following steps: (a) treating the sample with an agent that differentially modifies methylated and unmethylated DNA; and (b) detecting DNA sequence of RASSF1A, APC, CASP8, RARB, SCGB3A1, DAB2IP, PTPN6, THY1, TMEFF2 (GenBank accession No. NM_016192), or PYCARD (GenBank accession No. NM_013258) in the sample. The presence of the DNA sequence indicates the presence of fetal DNA in the sample, whereas the absence of the DNA sequence indicates the absence of fetal DNA in the sample.

In some embodiments, the sample from a pregnant woman is whole blood. In the alternative, the sample may be plasma, serum, urine, or saliva. In some embodiments, the agent capable of differentially modifying methylated and unmethylated DNA digests unmethylated DNA but not methylated DNA. This agent may be a methylation sensitive enzyme, particularly a methylation sensitive restriction enzyme, such as Hpa II or BstU I. In other embodiments, the agent may contain bisulfite.

In some embodiments, step (b) of the method comprises an amplification process. In an exemplary embodiment, the amplification process is a polymerase chain reaction (PCR), such as real-time PCR. In other embodiments, step (b) determines the quantity of the DNA sequence.

In some embodiments, when step (b) indicates the presence of fetal DNA in the sample, the method may include further steps of: (c) determining the amount of a second fetal DNA sequence in a second sample. The second sample is identical to the sample in step (a) prior to being treated with the agent that differentially modifies methylated and unmethylated DNA, and the second sequence is not RASSF1A, APC, CASP8, RARB, SCGB3A1, DAB2IP, PTPN6, THY1, TMEFF2, or PYCARD; and (d) comparing the amount of the second sequence with a standard control. When an increase in the amount of the second sequence from the control is detected, it is interpreted as an indicator of either the presence of a pregnancy-associated condition or an increased risk for developing such a condition. In some cases, the second sample in step (c) is not treated with any agent that differentially modifies methylated and unmethylated DNA, whereas in other cases, the second sample in step (c) is treated with the agent before the amount of the second fetal DNA sequence is determined. For instance, the second sample in step (c) is treated with a second, different agent that differentially modifies methylated and unmethylated DNA before the amount of the second fetal DNA sequence is determined. This method is suitable for detecting the presence of various pregnancy-associated conditions or an increased risk for developing one during pregnancy. Some examples of such a condition include preeclampsia, preterm labor, and intrauterine growth retardation (IUGR).

In other embodiments, when step (b) indicates the presence of fetal DNA in the sample, the method may comprise the further step of: (c) detecting a second fetal DNA sequence in a second sample. The second sample is identical to the sample in step (a) prior to being treated with the agent, and the second sequence is a gene of a RhD blood type, a gene of an ABO blood type, a gene of a RhC blood type, a gene of a RhE blood type, a gene of a HLA type, or a gene located on the Y chromosome, or a gene containing a pre-determined mutation, wherein the presence of the second sequence indicates the presence of the particular RhD blood type, the particular ABO blood type, the particular RhC blood type, the particular RhE blood type, the particular HLA type, the Y chromosome, or the pre-determined mutation within the gene in the fetal genome. In some cases, the second sample in step (c) is not treated with any agent that differentially modifies methylated and unmethylated DNA. Optionally, step (c) comprises an amplification process. In an exemplary embodiment, the amplification process is a polymerase chain reaction (PCR), such as real-time PCR.

In the second aspect of this invention, a method is provided for detecting a pregnancy-associated condition in a pregnant women. This method comprises the following steps: (a) treating a biological sample obtained from the woman with an agent that differentially modifies methylated and unmethylated DNA; (b) detecting the amount of DNA sequence of RASSF1A, CASP8, RARB, SCGB3A1, DAB2IP, PTPN6, THY1, TMEFF2, or PYCARD in the sample; and (c) comparing the amount of the DNA sequence with a standard control, wherein an increase from the control indicates the presence of or an increased risk for developing the pregnancy-associated condition.

In some embodiments, the agent capable of differentially modifying methylated or unmethylated DNA digests unmethylated DNA but not methylated DNA. One possibility is that the agent is a methylation sensitive enzyme, such as a methylation sensitive restriction enzyme (e.g., Hpa II or BstU I). Another possibility is that the agent comprises bisulfite.

In some embodiments, step (b) of the method comprises an amplification process, which may accomplished by various means, including polymerase chain reaction (PCR), such as real-time PCR. This method is suitable for the diagnosis, monitoring, or risk assessment of a number of pregnancy-associated conditions, including is preeclampsia, preterm labor, and intrauterine growth retardation (IUGR).

BRIEF DESCRIPTION OF THE DRAWINGS

FIG. 1. Primer, probe and standard calibrator sequences for RASSF1A (SEQ ID NOs: 1-8), APC (SEQ ID NOs: 9 and 10), and RARB (SEQ ID NOs: 11-14) sequences and PCR reaction conditions.

FIG. 3. Methylation status of APC and RARB CpG islands in first- and third-trimester placental tissues and corresponding maternal blood cells. For APC, the analysed CpG sites are named according to GenBank Accession NM_000038 with the start codon of its protein coding sequence as position +1. The first CpG site (−17371) corresponds to chr5:112101115 of the human genome in the UCSC Genome Browser (May 2004 assembly, hg17). For RARB, the analysed CpG sites are named according to GenBank Accession NM_016152 with the start codon of its protein coding sequence as position +1. The first CpG site (−73231) corresponds to chr3:25444475 (forward strand) of the human genome in the UCSC Genome Browser (May 2004 assembly, hg17). Filled and unfilled circles represent methylated and unmethylated CpG sites, respectively.

FIG. 4. Primer, probe and standard calibrator sequences for CASP8 (SEQ ID NOs: 15-18) and PCR reaction condition conditions.

FIG. 6. Primer, probe and standard calibrator sequences for SCGB3A1 (SEQ ID NOs: 19-22) and PCR reaction conditions.

FIG. 17. Primer sequences for bisulfite sequencing of DAB21P (SEQ ID NOs: 23-26) and PCR reaction conditions.

DEFINITIONS

Figure 2A:
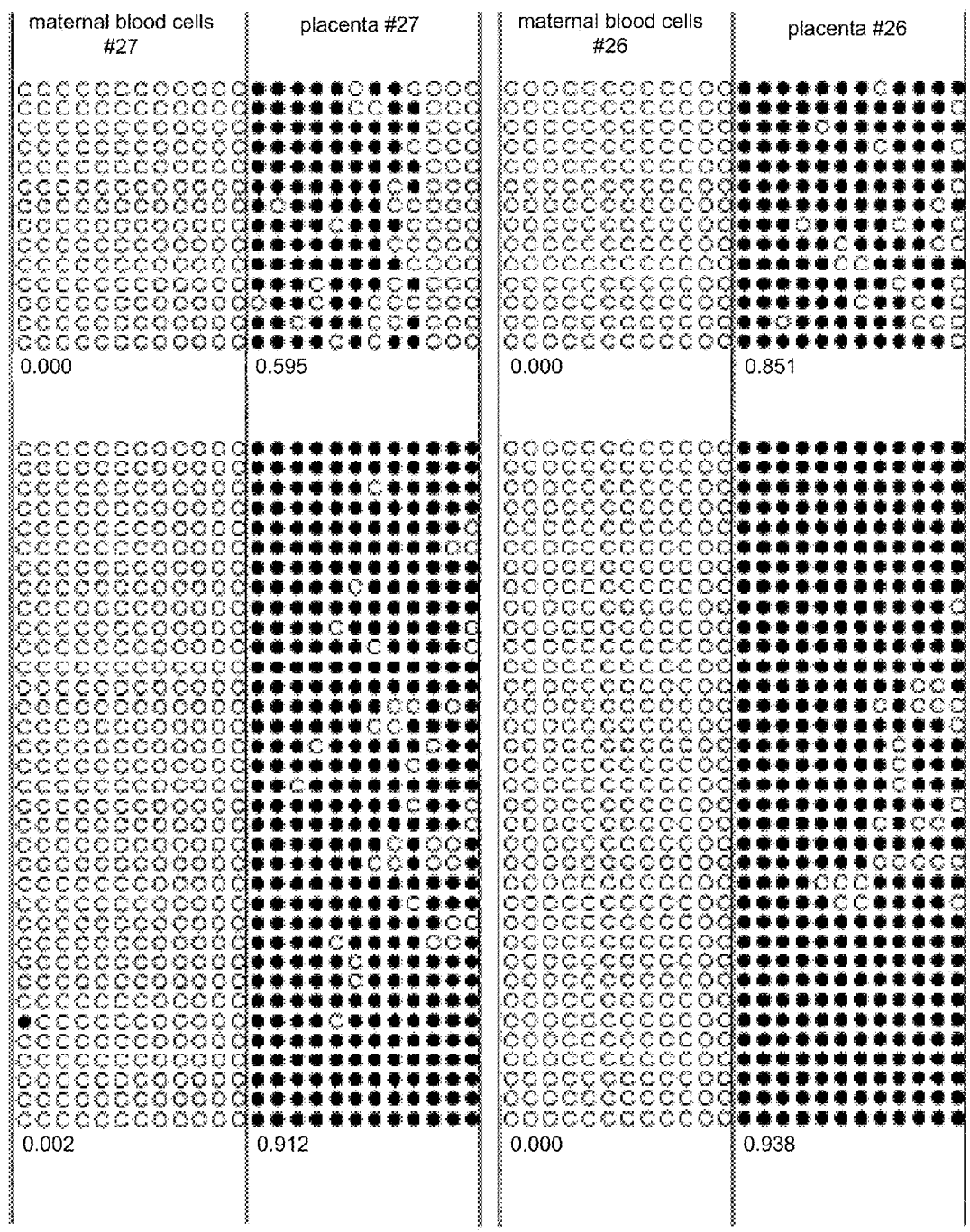
FIG. 2. Methylation status of RASSF1A CpG island in (a) first and (b) third trimester placental tissues and corresponding maternal blood cells. The analyzed CpG sites are numbered serially and named according to the RASSF1 (*Homo sapiens*) GenBank Accession NM_007182 with the start codon of its protein coding sequence as position +1 (in parentheses). The first CpG site (−113) corresponds to chr3: 50353354 (reverse strand) of the human genome in the UCSC Genome Browser (May 2004 assembly, hg17). Filled and unfilled circles represent methylated and unmethylated CpG sites, respectively.
Figure 2A:
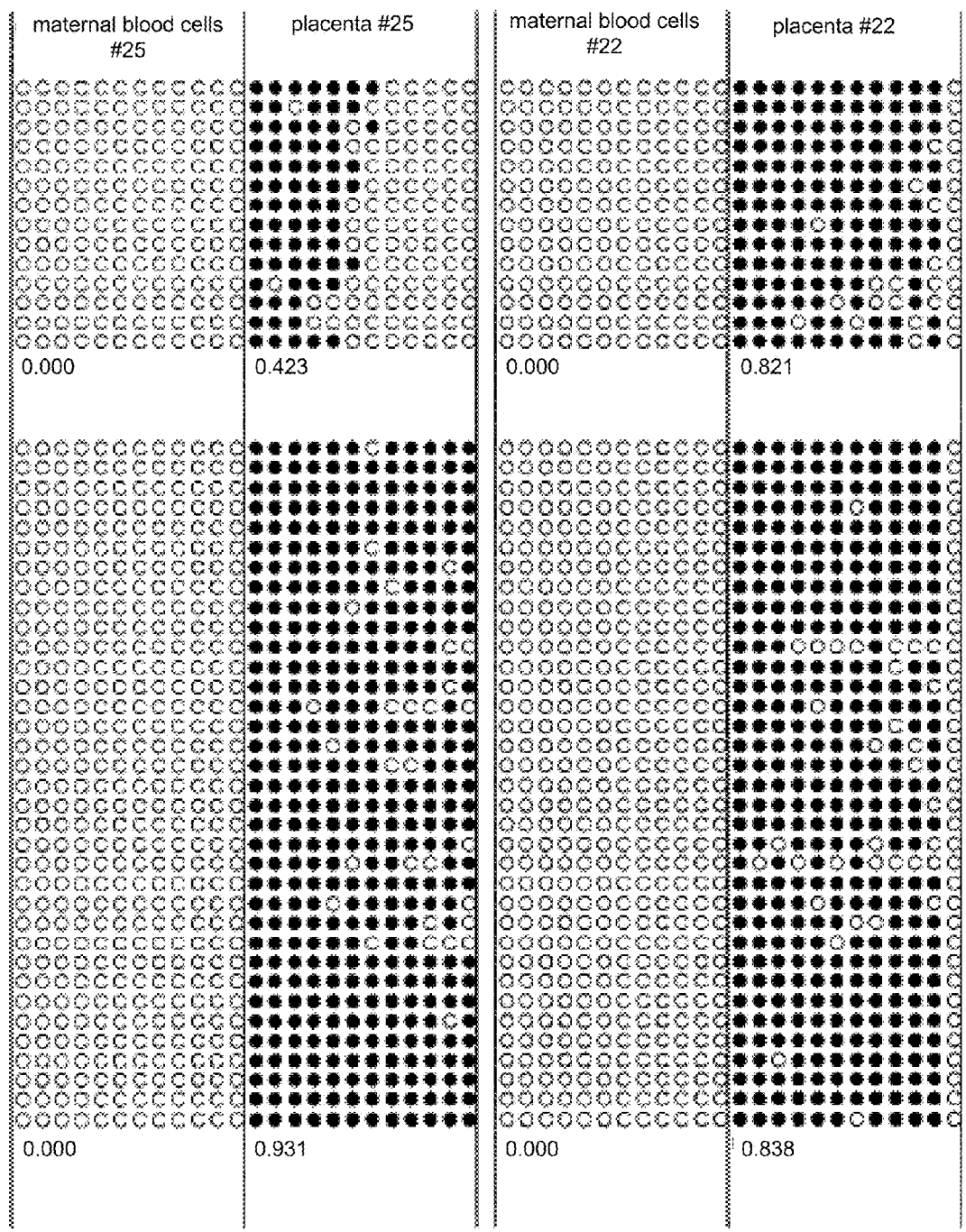
Figure 2A:
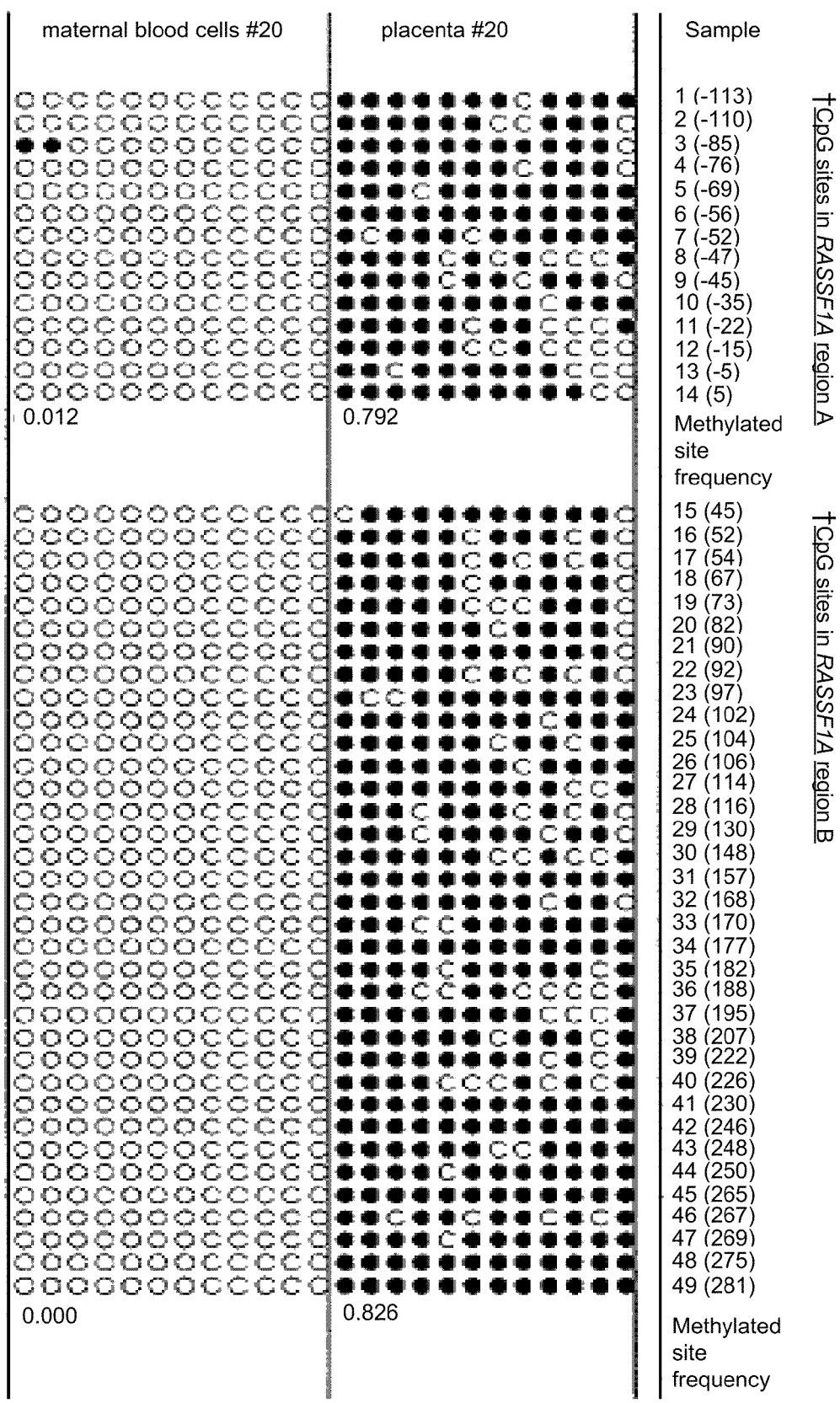
Figure 2B:
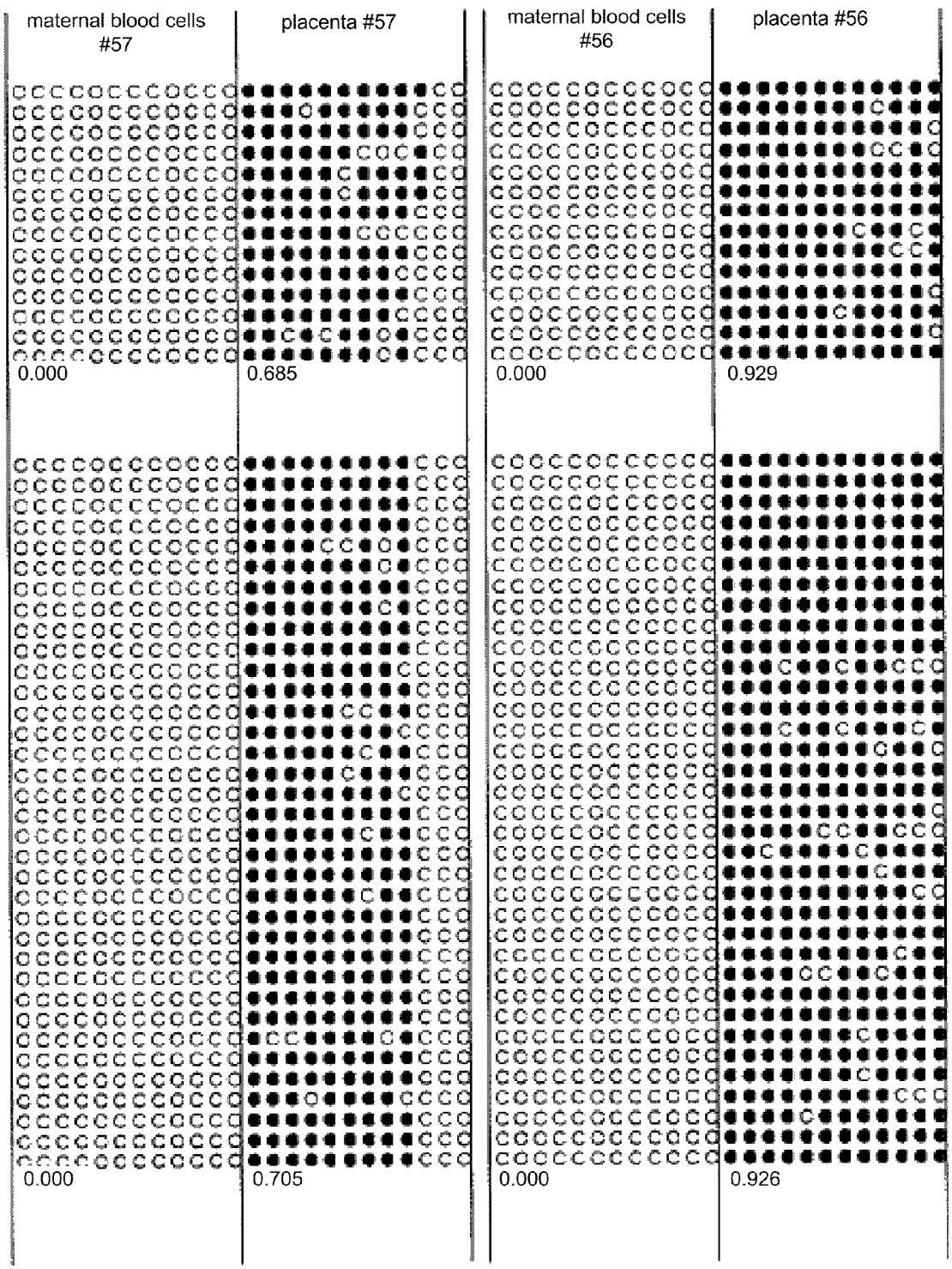
Figure 2B:
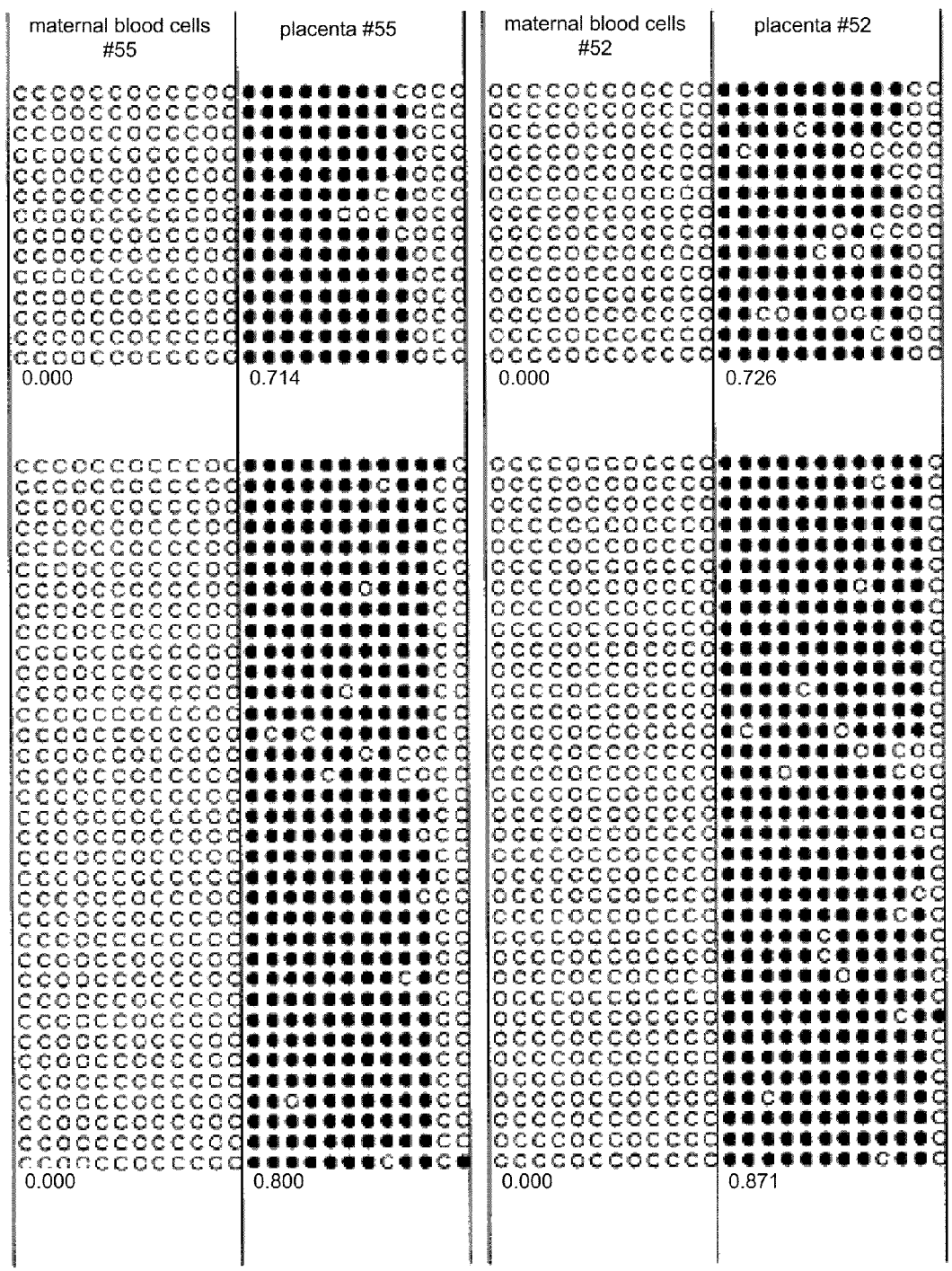
Figure 2B:
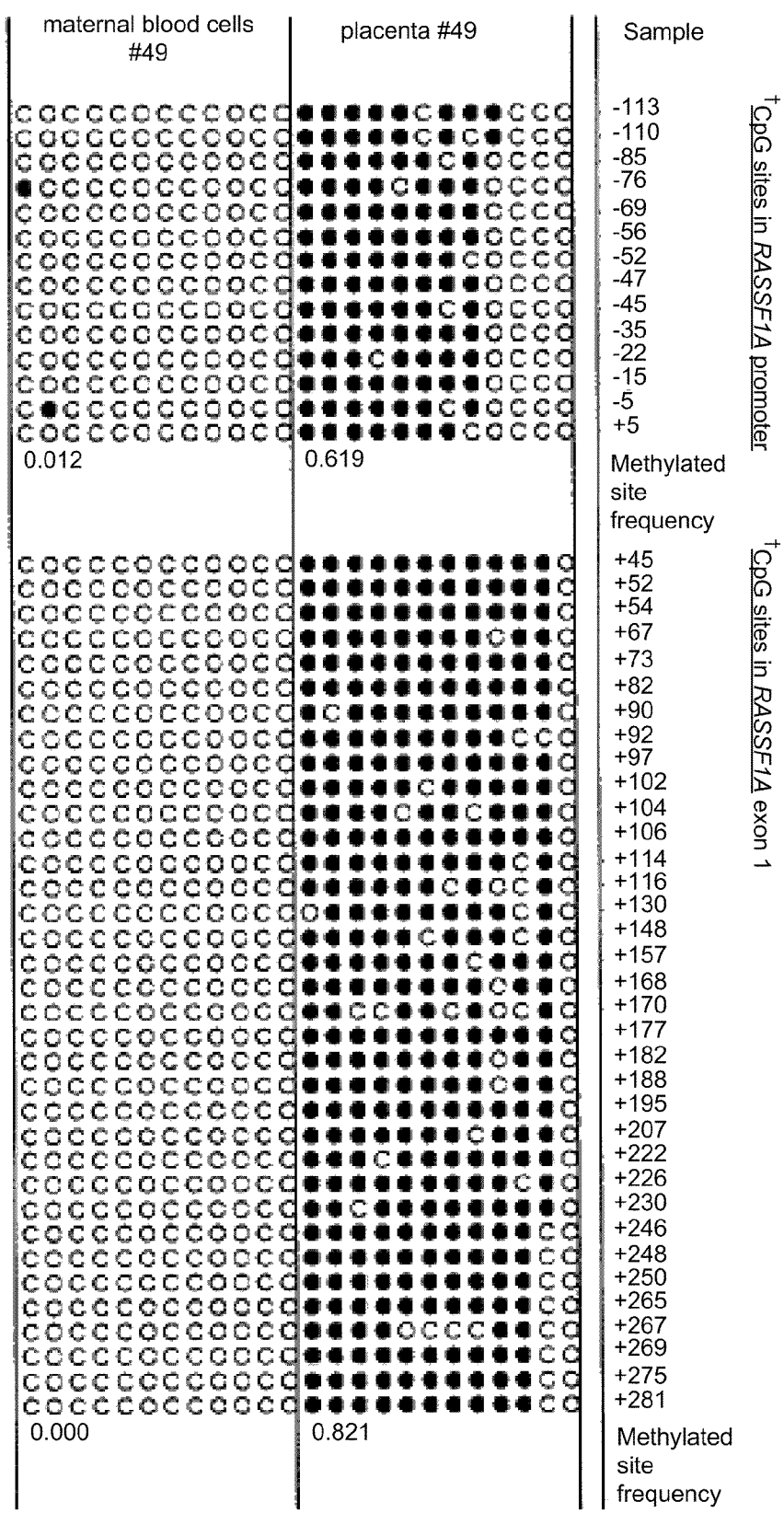

The term "pregnancy-associated disorder," as used in this application, refers to any condition or disease that may affect a pregnant woman, the fetus the woman is carrying, or both the woman and the fetus. Such a condition or disease may manifest its symptoms during a limited time period, e.g., during pregnancy or delivery, or may last the entire life span of the fetus following its birth. Some examples of a pregnancy-associated disorder include preeclampsia, preterm labor, and intrauterine growth retardation (IUGR).

In this application, the term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, mutations including point mutations, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991);

Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that modifies methylated and/or unmethylated DNA in a process through which distinguishable products result from methylated and non-methylated DNA, thereby allowing the identification of the DNA methylation status. Such processes may include, but are not limited to, chemical reactions (such as a C→U conversion by bisulfite) and enzymatic treatment (such as cleavage by a methylation-dependent endonuclease). Thus, an enzyme that preferentially cleaves or digests methylated DNA is one capable of cleaving or digesting a DNA molecule at a much higher efficiency when the DNA is methylated, whereas an enzyme that preferentially cleaves or digests unmethylated DNA exhibits a significantly higher efficiency when the DNA is not methylated.

In this application, the word "presence" or "absence" is used in a relative sense to describe the level of a particular DNA sequence. In other words, when a given DNA sequence or a gene is said to be "present" in a test sample, it means the level of this DNA sequence or gene is above a pre-determined threshold; whereas when a DNA sequence or gene is "absent" when its level in a test sample is below such a threshold.

As used in this application, an "increase" or a "decrease" refers to a detectable positive or negative change in quantity from an established standard control. An increase is a positive change preferably at least 10%, more preferably 50%, still more preferably 2-fold, even more preferably at least 5-fold, and most preferably at least 10-fold of the control value. Similarly, a decrease is a negative change preferably at least 10%, more preferably 50%, still more preferably at least 80%, and most preferably at least 90% of the control. Other terms indicating quantitative changes or differences from a comparative basis, such as "more" or "less," are used in this application in the same fashion as described above.

A "polynucleotide hybridization method" as used herein refers to a method for detecting the presence and/or quantity of a polynucleotide based on its ability to form Watson-Crick base-pairing, under appropriate hybridization conditions, with a polynucleotide probe of a known sequence. Examples of such hybridization methods include Southern blotting and Northern blotting.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., RASSF1A, APC, CASP8, RARB, SCGB3A1, DAB2IP, PTPN6, THY1, TMEFF2, or PYCARD, either methylated or unmethylated. At least one of the PCR primers for amplification of a polynucleotide sequence is sequence-specific for the sequence.

"Standard control value" as used herein refers to a predetermined amount of a genomic sequence that is originated from a fetus and is present in an established sample. The standard control value is suitable for the use of a method of the present invention, in order for comparing the amount of a gene of interest (or a non-coding sequence) that is present in a test sample. An established sample serving as a standard control provides an average amount of a fetal gene of interest that is typical for a defined time (e.g., first trimester) during pregnancy in the blood of an average, healthy pregnant woman carrying a normal fetus, both of whom are not at risk of developing any pregnancy-associated disorders or complications. A standard control value may vary depending on the genomic sequence of interest and the nature of the sample.

The term "average," as used in the context of describing a pregnant woman, refers to the fact that the woman is free of at least one condition of relevance, such as a pregnancy-associated condition (e.g., preeclampsia or preterm labor). The term "average," when used in other context, refers to certain characteristics, such as the amount or methylation status of a particular gene of both maternal and fetal origins found in the woman's blood, that are representative of a randomly selected group of healthy women who are pregnant with chromosomally normal fetuses and not susceptible to any pregnancy-related diseases or conditions. This selected group should comprise a sufficient number of women such that the average amount or methylation profile of the gene of interest among these women reflects, with reasonable accuracy, the corresponding profile in the general population of healthy pregnant women with healthy fetuses. In addition, the selected group of women generally has a similar gestational age to that of a woman whose blood is tested for indication of a potential pregnancy-associated disorder. The preferred gestational age for practicing the present invention may vary depends on the disorder that is being screened for. For example, a pregnant woman is screened for the risk of preeclampsia preferably during the second trimester of the pregnancy, whereas fetal chromosomal aneuploidy is preferably screened for and diagnosed as early as possible. Moreover, the preferred gestational age for testing may also depend on the gene of interest in testing.

The term "preeclampsia" as used herein refers to a condition that occurs during pregnancy, the main symptom of which is various forms of high blood pressure often accompanied by the presence of proteins in the urine and edema (swelling). Preeclampsia, sometimes called toxemia of pregnancy, is related to a more serious disorder called "eclampsia," which is preeclampsia together with seizures. These conditions usually develop during the second half of pregnancy (after 20 weeks), though they may develop shortly after birth or before 20 weeks of pregnancy.

The term "preterm labor" or "premature labor" as used herein refers to the condition where labor that begins more than three weeks before the full gestation period of about 40 weeks, which often leads to premature birth if not treated.

The term "intrauterine growth retardation (IUGR)" refers to a condition in which the growth of the fetus is abnormally slow, its weight below the 10th percentile for gestational age. When born, the infant appears too small and undernourished for its age. IUGR, also referred to as intrauterine growth restriction, is associated with increased risk of medical illness and death in the newborn.

As used in this application, "a gene of a RhD blood type, of an ABO blood type, of a RhC blood type, of a RhE blood type, of a HLA type, or on the Y chromosome" refers to a gene that is recognized as representative of a particular blood type in accordance with the RhD, ABO, RhC, or RhE blood typing, or a particular HLA type, or a gene that is located on the Y chromosome. The detection of such a gene in fetal DNA is indicative of the fetus being a particular blood type, HLA type, or the male gender.

DETAILED DESCRIPTION OF THE INVENTION

I. Introduction

The presence of fetal DNA in maternal plasma was first reported in 1997, offering the possibility for non-invasive prenatal diagnosis simply through the analysis of a maternal blood sample (Lo et al., *Lancet* 350:485-487, 1997). The co-existence of fetal DNA with background maternal DNA in maternal plasma, however, demands reliable means to distinguish DNA of fetal and maternal origins. Several genes have been previously indicated as differentially methylated between their fetal and maternal versions, see, e.g., Chim et al., *Proc. Natl. Acad. Sci. USA* 102:14753-14758, 2005.

The present inventors discovered, for the first time, that a number of genes (e.g., RASSF1A, APC, CASP8, RARB, SCGB3A1, DAB2IP, PTPN6, THY1, TMEFF2, and PYCARD) derived from a fetus are highly methylated, whereas the same genes derived from the woman pregnant with the fetus are not methylated. Although other genes have previously been reported to have distinct methylation profile when the fetal version of the genes and maternal version are compared, the discovery by the present inventors is unique in that not only was such distinction of methylation status previously unknown with regard to these particular genes, the high level of uniformity in the methylation of the fetal genes and the lack of methylation of the maternal genes was also previously not seen. This discovery thus provides a new, more accurate, and more effective approach for distinguishing fetal and maternal genomic DNA. In particular, the detection of any one of the fetal genes identified herein in a sample during an analytic process for non-invasive prenatal diagnosis allows the confirmation that the process, including sample collection and manipulation, is operating successfully as designed in that fetal DNA in general (not limited to the genes named herein) in the sample is properly preserved both in quality and in quantity. In addition, these newly identified genes can also be used directly as fetal DNA markers to indicate the presence of or heightened risk for certain pregnancy-related conditions and complications, since these genes are uniformly methylated compared to their maternal counterparts, permitting easy distinction between the maternal copy and the fetal copy of the genes.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange high performance liquid chromatography (HPLC) as described in Pearson & Reanier, *J. Chrom.* 255: 137-149 (1983).

Any one of the genes identified in the present invention, RASSF1A, APC, CASP8, RARB, SCGB3A1, DAB2IP, PTPN6, THY1, TMEFF2, and PYCARD, and the polynucleotide sequence of synthetic oligonucleotides can be verified using, e.g., the chain termination method for sequencing double-stranded templates of Wallace et al., *Gene* 16: 21-26 (1981).

III. Acquisition of Blood Samples and Extraction of DNA

The present invention relates to determining the presence and/or quantity of certain fetal genes found in maternal blood based on their distinct methylation status to detect the presence and/or quantity of general fetal DNA, which may be used, for example, as an internal control to indicate the proper operation of a non-invasive analytical process that utilizes fetal DNA for assessing the presence or risk of a pregnancy-associated condition or disorder. Thus, the first steps of practicing this invention are to obtain a biological sample from a pregnant woman where fetal DNA is expected to be present and treat the DNA with an agent that differentially modifies DNA based on the methylation state. One example of such an agent is one that digests only unmethylated DNA but not methylated DNA. Optionally, the DNA is first extracted from the sample.

A. Acquisition of Blood Samples

A blood sample is obtained from a pregnant woman at a gestational age suitable for testing using a fetal DNA-based non-invasive diagnostic method. The suitable gestational age may vary depending on the disorder tested. Collection of blood from a woman is performed in accordance with the standard protocol hospitals or clinics generally follow. An appropriate amount of peripheral blood, e.g., typically between 5-50 ml, is collected and may be stored according to standard procedure prior to further preparation.

B. Preparation of Blood Samples

The analysis of fetal DNA found in maternal blood according to the present invention may be performed using, e.g., the whole blood, serum, or plasma. The methods for preparing serum or plasma from maternal blood are well known among those of skill in the art. For example, a pregnant woman's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. On the other hand, serum may be obtained with or without centrifugation following blood clotting. If centrifugation is used then it is typically, though not exclusively, conducted at an appropriate speed, e.g., 1,500-3,000× g. Plasma or serum may be subjected to additional centrifugation steps before being transferred to a fresh tube for DNA extraction.

In addition to the acellular portion of the whole blood, DNA may also be recovered from the cellular fraction, enriched in the buffy coat portion, which can be obtained following centrifugation of a whole blood sample from the woman and removal of the plasma.

C. Extraction of DNA

There are numerous known methods for extracting DNA from a biological sample including blood. The general methods of DNA preparation (e.g., described by Sambrook and Russell, *Molecular Cloning: A Laboratory Manual* 3d ed., 2001) can be followed; various commercially available reagents or kits, such as QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), may also be used to obtain DNA from a blood sample from a pregnant woman. Combinations of more than one of these methods may also be used.

IV. Methylation-Specific Chemical Modification of DNA

The DNA present in a sample from a pregnant woman, whether or not extracted from the sample, is then treated with an agent capable of preferentially modifying DNA depending on whether the DNA sequence is methylated. For instance, this agent can be an enzyme that digests DNA in a methylation sensitive manner, i.e., only unmethylated DNA will be digested while methylated DNA remains unchanged. Another possibility is that the agent selectively converts a polynucleotide sequence depending on the methylation status. Typically, such an agent reacts with the unmethylated C residue(s) in a DNA molecule and converts each unmethylated C residue to a uracil (U) residue, whereas the methylated C residues remain unchanged. This C→U conversion allows detection and comparison of methylation status based on changes in the primary sequence of the nucleic acid. An exemplary reagent suitable for this purpose is bisulfite, such as sodium bisulfite. Methods for using bisulfite for chemical modification of DNA are well known in the art (see, e.g., Herman et al., *Proc. Natl. Acad. Sci. USA* 93:9821-9826, 1996) and will not be discussed in detail here.

As a skilled artisan will recognize, any other reagents that are unnamed here but have the same property of chemically (or through any other mechanism) modifying methylated and unmethylated DNA differentially can be used for practicing the present invention. For instance, methylation-specific modification of DNA may also be accomplished by methylation-sensitive restriction enzymes, some of which typically cleave an unmethylated DNA fragment but not a methylated DNA fragment, while others (e.g., methylation-dependent endonuclease McrBC) cleave DNA containing methylated cytosines but not unmethylated DNA. In addition, a combination of chemical modification and restriction enzyme treatment, e.g., combined bisulfite restriction analysis (COBRA), may be used for practicing the present invention.

V. Polynucleotide Sequence Amplification and Determination

Following the methylation-dependent differential modification of the DNA, such as chemical modification of DNA in a methylation-specific manner or methylation-sensitive enzymatic digestion, the treated DNA is then subjected to a sequence-based analysis, such that one or more of the relevant genes of the present invention (e.g., RASSF1A, APC, CASP8, RARB, SCGB3A1, DAB2IP, PTPN6, THY1, TMEFF2, or PYCARD) from the fetal source may be distinguished from their counterparts from the maternal source, and that the presence and quantity of the fetal gene(s) may be determined and compared to a standard control. Furthermore, once it is determined that one or more of these genes of fetal origin is indeed present in the sample, particularly when the amount of the gene(s) is greater than a pre-determined threshold, the sample and its equivalents are deemed to contain sufficient amount of fetal DNA for further analyses. On the other hand, one may detect and measure the quantity of these particular genes as fetal markers indicative of certain conditions or disorders related pregnancy, taking advantage of the genes' highly methylated status in contrast to the unmethylated status of their counterparts of maternal origin. For this use, the amount of one or more of the fetal genes selected from RASSF1A, CASP8, RARB, SCGB3A1, DAB2IP, PTPN6, THY1, TMEFF2, and PYCARD in a test sample can be compared to a standard value, where an increase from the standard value indicates the presence or heightened risk of such a pregnancy-associated disorder.

A. Amplification of Nucleotide Sequences

An amplification reaction is optional prior to a sequence-based analysis for a fetal marker of this invention after treatment by the methylation-dependent differential modification process. In some embodiments of this invention, the amplification is performed to preferentially amplify a fetal marker of this invention that has a particular methylation pattern, such that only the genomic sequence from one particular source, e.g., from the placenta or other tissues of the fetus, is detected and analyzed.

A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of a target polynucleotide sequence (e.g., that of RASSF1A, APC, CASP8, RARB, SCGB3A1, DAB2IP, PTPN6, THY1, TMEFF2, or PYCARD) is typically used in practicing the present invention, one of skill in the art will recognize that the amplification of a genomic sequence found in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to qualitatively demonstrate the presence of a particular genomic sequence of this invention, which represents a particular methylation pattern, or to quantitatively determine the amount of this particular genomic sequence in the maternal blood. For a review of branched-DNA signal amplification for direct quantification of nucleic acid sequences in clinical samples, see Nolte, *Adv. Clin. Chem.* 33:201-235, 1998.

B. Determination of Polynucleotide Sequences

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes (e.g., C→U) in a polynucleotide sequence for practicing the methods of the present invention include but are not limited to mass spectrometry, primer extension, polynucleotide hybridization, real-time PCR, and electrophoresis.

VI. Establishing a Standard Control Value

In order to establish a standard control value for practicing the method of this invention, a group of healthy pregnant women carrying healthy fetuses are first selected. These women are of similar gestational age, which is within the appropriate time period of pregnancy for screening of conditions such as preeclampsia and preterm labor using the methods of the present invention.

The healthy status of the selected pregnant women and the fetuses they are carrying are confirmed by well established, routinely employed methods including but not limited to monitoring blood pressure of the women, recording the onset of labor, and conducting fetal genetic analysis using CVS and amniocentesis.

Furthermore, the selected group of healthy pregnant women carrying healthy fetuses must be of a reasonable size, such that the average amount of a particular fetal gene identified in this invention present in the maternal blood obtained from the group can be reasonably regarded as representative of the normal or average amount or methylation profile among the general population of healthy women carrying healthy fetuses. Preferably, the selected group comprises at least 10 women.

Once an average level is established for a particular fetal gene present in the maternal blood based on the individual values found in each woman of the selected healthy control group, this average or median or representative value is considered a standard control value. Any biological sample (e.g., a blood sample) that contains a similar amount of the fetal gene can thus be used to provide a standard control value for samples of the same kind (e.g., blood samples). Furthermore, a solution containing a genomic DNA sequence in the average or median or representative amount can also be artificially assembled and to provide a standard control value. Standard control value may differ from gene to gene and depending on the nature of biological samples, i.e., the standard control value for RASSF1A may be different for a plasma sample from that for a saliva sample.

EXAMPLES

The following examples are provided by way of illustration only and not by way of limitation. Those of skill in the art will readily recognize a variety of non-critical parameters that could be changed or modified to yield essentially the same or similar results.

Example 1

Tumor Suppressor Genes that are Hypermethylated in the Fetus Compared with Maternal Blood We aimed to identify epigenetic markers that are fetal-specific in maternal blood. Previous data suggest that fetal DNA molecules in maternal plasma are predominantly derived from the placenta (Chim et al., *Proc Natl Acad Sci USA.*, 102, 14753-14758; Masuzaki et al., *J Med Genet* 41, 289-292, 2004; Flori et al., *Hum Reprod* 19, 723-724, 2004), while the background DNA in maternal plasma may originate from maternal blood cells (Lui et al., *Clin Chem* 48, 421-427, 2002). Hence, to identify fetal epigenetic markers, the methylation profiles of genomic loci were assessed in both placental tissues and maternal blood cells with an aim to identify loci that demonstrate differential methylation between the two tissue types. Such markers can be used for prenatal diagnosis and monitoring of pregnancy-related conditions.

Subject Recruitment and Sample Collection

Subjects were recruited from the Department of Obstetrics and Gynaecology, Prince of Wales Hospital, Hong Kong. The study and the collection of human clinical samples were approved by the institutional review board. Informed consent was sought from each subject. First trimester placental tissues were collected immediately after elective pregnancy terminations. Third trimester placental tissues were collected after elective cesarean delivery of uncomplicated pregnancies. Maternal peripheral blood samples (12 mL EDTA) were collected just prior to the performance of obstetrics procedures.

Sample Processing and Bisulfite Sequencing

Blood samples were centrifuged at 1,600 g for 10 min at 4° C. After the removal of the supernatant, the peripheral blood cell portion was re-centrifuged at 2,500 g. Any residual plasma was further removed. DNA was extracted from peripheral blood cells using the Nucleon Blood DNA extraction kit (GE Healthcare-Biosciences, Little Chalfont, United Kingdom) and from placental tissues using the QIAamp Tissue Kit (Qiagen, Hilden, Germany), each according to the manufacturer's instructions. Bisulfite converts unmethylated cytosine into uracil, while leaving methylated cytosine unchanged. Extracted DNA samples were bisulfite converted using the CpGenome Universal DNA Modification Kit (Chemicon, Temecula, Calif.) according to the manufacturer's instructions. For each conversion reaction, 1 μg of DNA was incubated at 50° C. for 16 hours after the addition of Reagent I. Each bisulfite converted DNA sample was subjected to PCR by primers that did not discriminate between methylated and unmethylated sequences, using a GeneAmp PCR Core Reagent kit (Applied Biosystems). Each subsequent PCR product was TA-cloned into pGEM-Teasy vector (Promega) for transformation into *E. coli* strain JM109, according to the manufacturer's instructions. Clones were picked randomly and colony PCR was then performed using vector primers T7 and SP6 to amplify the cloned inserts. Cycle sequencing was performed using BigDye version 1.1 (Applied Biosystems) and an automated capillary DNA sequencer Genetic Analyzer 3100 (Applied Biosystems). The sequences obtained were aligned and compared using SeqScape software (Applied Biosystems). The completeness of bisulfite conversion was first confirmed before scoring. The CpG sites sequenced as cytosine or thymine residues were scored as methylated or unmethylated, respectively. The methylated site frequency was calculated for each sample by dividing the total number of methylated sites over all cloned CpG sites.

Data Comparison and Statistical Analysis

Following bisulfite conversion, a CpG site was scored as methylated if the sequence was cytosine; scored as unmethylated if it was occupied by a thymine residue (deoxy counterpart of uracil). The methylated site frequency was calculated for each sample by dividing the total number of methylated sites over all cloned CpG sites.

RASSF1A, APC, and RARB

PCR primers for bisulfite sequencing and the PCR cycling conditions are listed in FIG. 1. The bisulfite sequencing results are listed in FIGS. 2 and 3. These results indicated that RASSF1A, APC, and RARB sequences were hypermethylated in the placenta, but not methylated in the maternal blood cells.

CASP8

Figure 5:
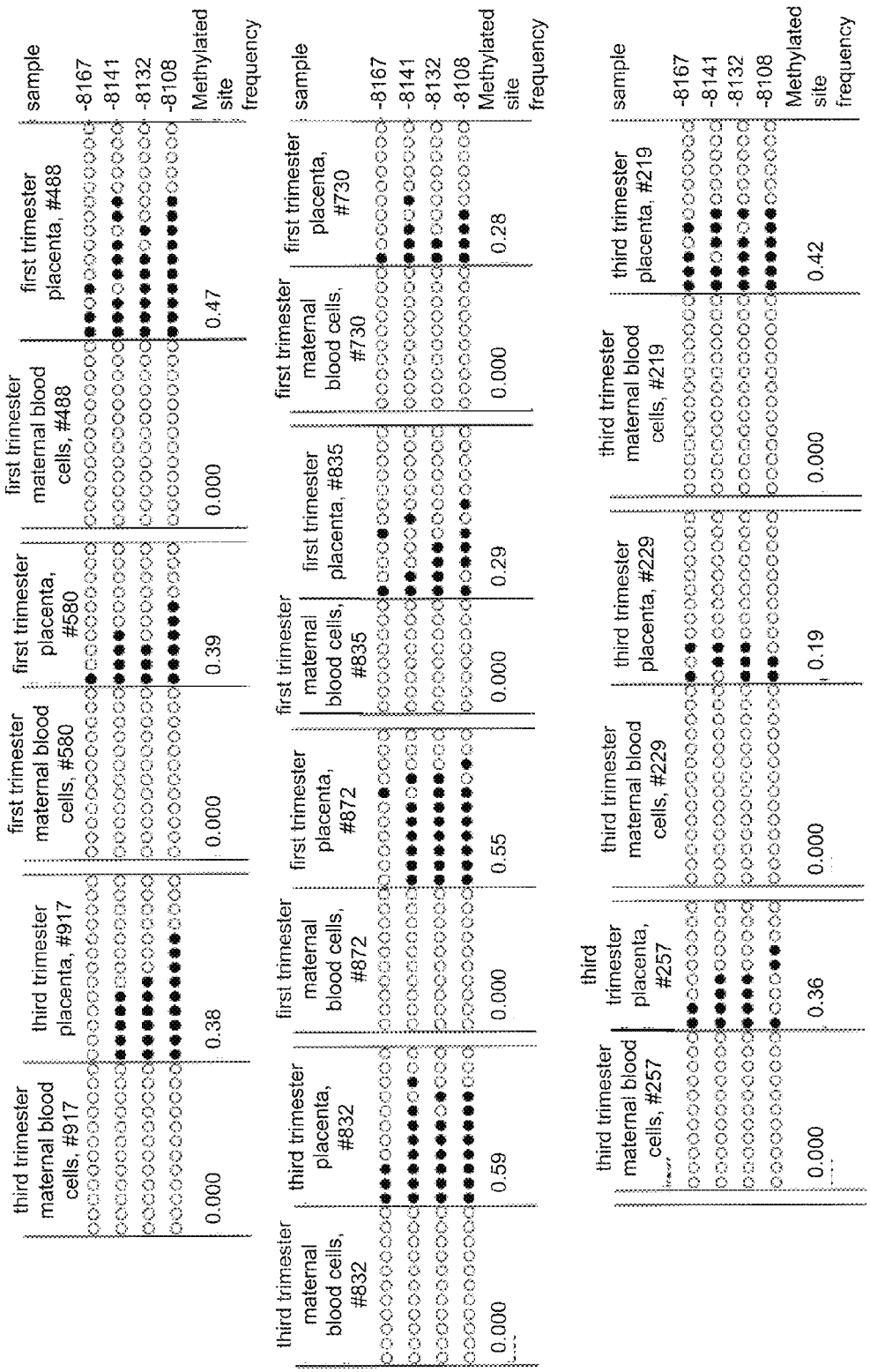
FIG. 5. Methylation status of CASP8 CpG island in first- and third-trimester placental tissues and corresponding maternal blood cells. The analysed CpG sites are named according to the CASP8 (*Homo sapiens*) GenBank Accession NM_033355 with the start codon of its protein coding sequence as position +1. The first CpG site (−8167) corresponds to chr2:201948550 of the human genome in the UCSC Genome Browser (May 2004 assembly, hg17). Filled and unfilled circles represent methylated and unmethylated CpG sites, respectively.

The PCR primers for bisulfite sequencing and PCR cycling conditions are listed in FIG. 4. Bisulfite sequencing results are listed in FIG. 5. These results indicated that CASP8 sequences were hypermethylated in the placenta, but not methylated in the maternal blood cells.

SCGB3A1

Figure 7:
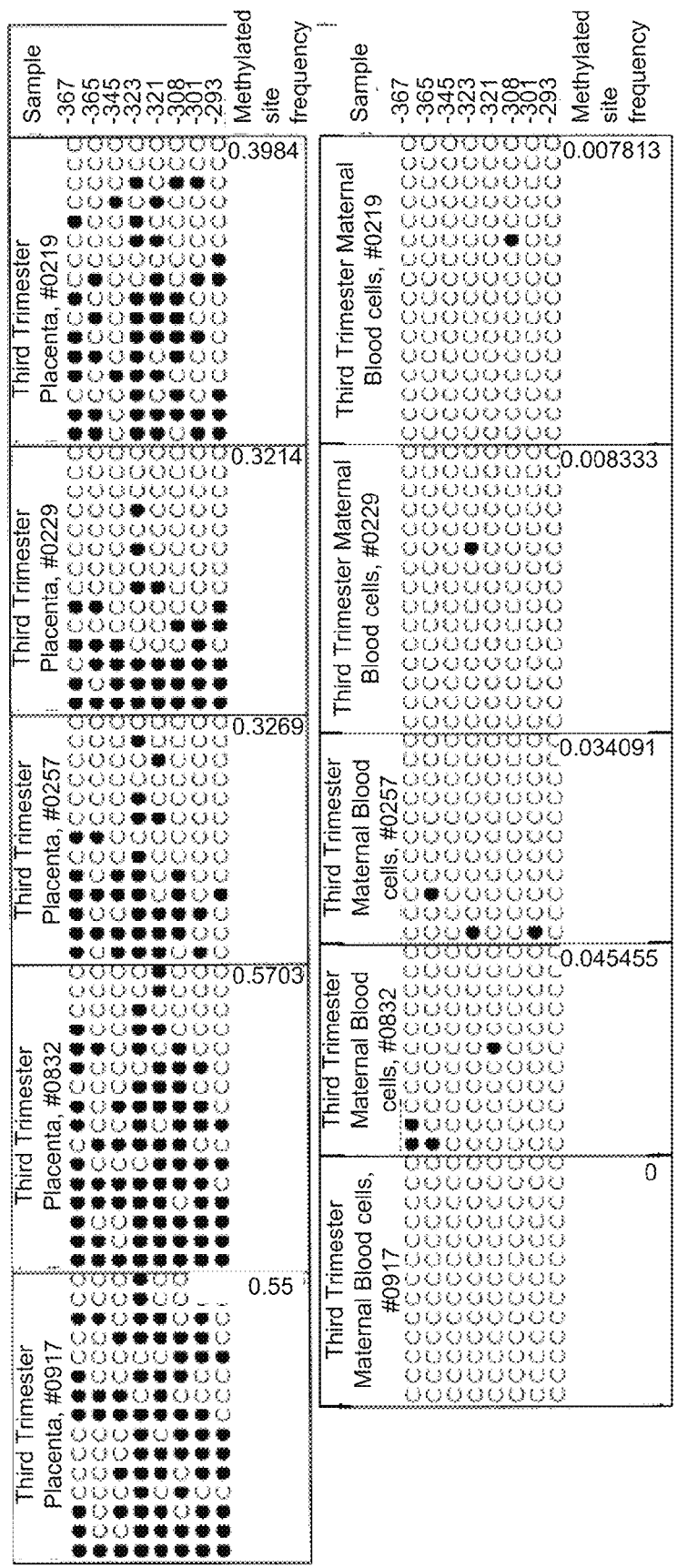
FIG. 7. Methylation status of SCGB3A1 CpG island in third-trimester placental tissues and corresponding maternal blood cells. The analysed CpG sites are named according to the SCGB3A1 (*Homo sapiens*) GenBank Accession NM_052863 with the start codon of its protein coding sequence as position +1. The first CpG site (−390) corresponds to chr5:179951435 of the human genome in the UCSC Genome Browser (May 2004 assembly, hg17).

The PCR primers for bisulfite sequencing and PCR cycling conditions are listed in FIG. 6 Bisulfite sequencing results are listed in FIG. 7. These results indicated that SCGB3A1 sequences were hypermethylated in the placenta, but largely not methylated in the maternal blood cells.

DAB2 Interacting Protein (DAB2IP)

Figure 18:
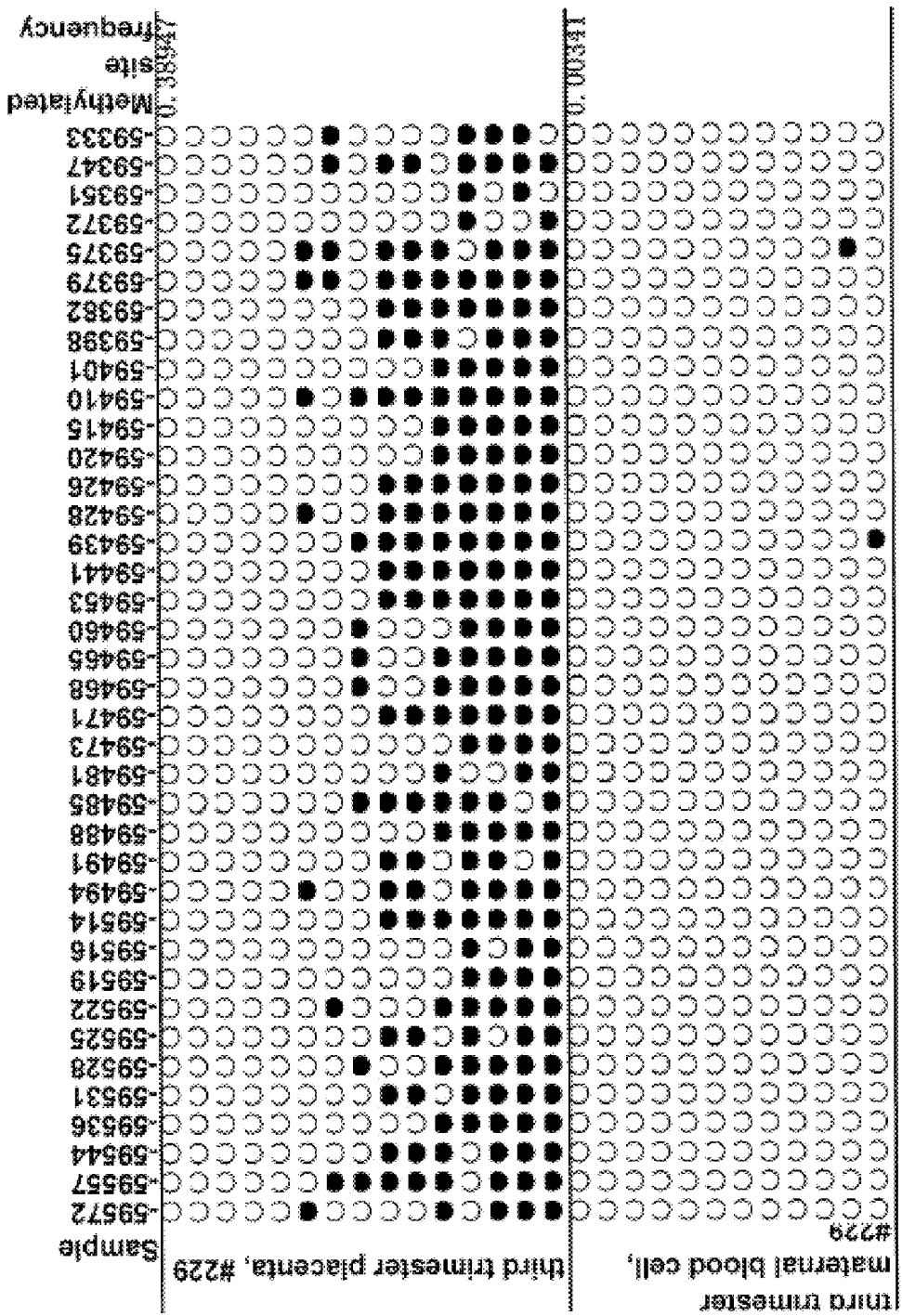
FIG. 18. Methylation status of DAB2IP CpG island in a third-trimester placental tissue sample and corresponding maternal blood cells. The analysed CpG sites are named according to the DAB2IP (*Homo sapiens*) GenBank Accession NM_032552 with the start codon of its protein coding sequence as position +1. The first CpG site (−59572) corresponds to chr9:121541221 of the human genome in the UCSC Genome Browser (May 2004 assembly, hg17). Filled and unfilled circles represent methylated and unmethylated CpG sites, respectively.

The PCR primers for bisulfite sequencing and PCR cycling conditions are listed in FIG. 17. Bisulfite sequencing results for one placental tissue sample and the corresponding maternal blood cells are listed in FIG. 18. These results indicated that DAB2IP sequences were hypermethylated in the placenta, but not methylated in the maternal blood cells.

Example 2

Methylation Sensitive Enzyme Digestion Followed by Real-Time PCR

Figure 8:
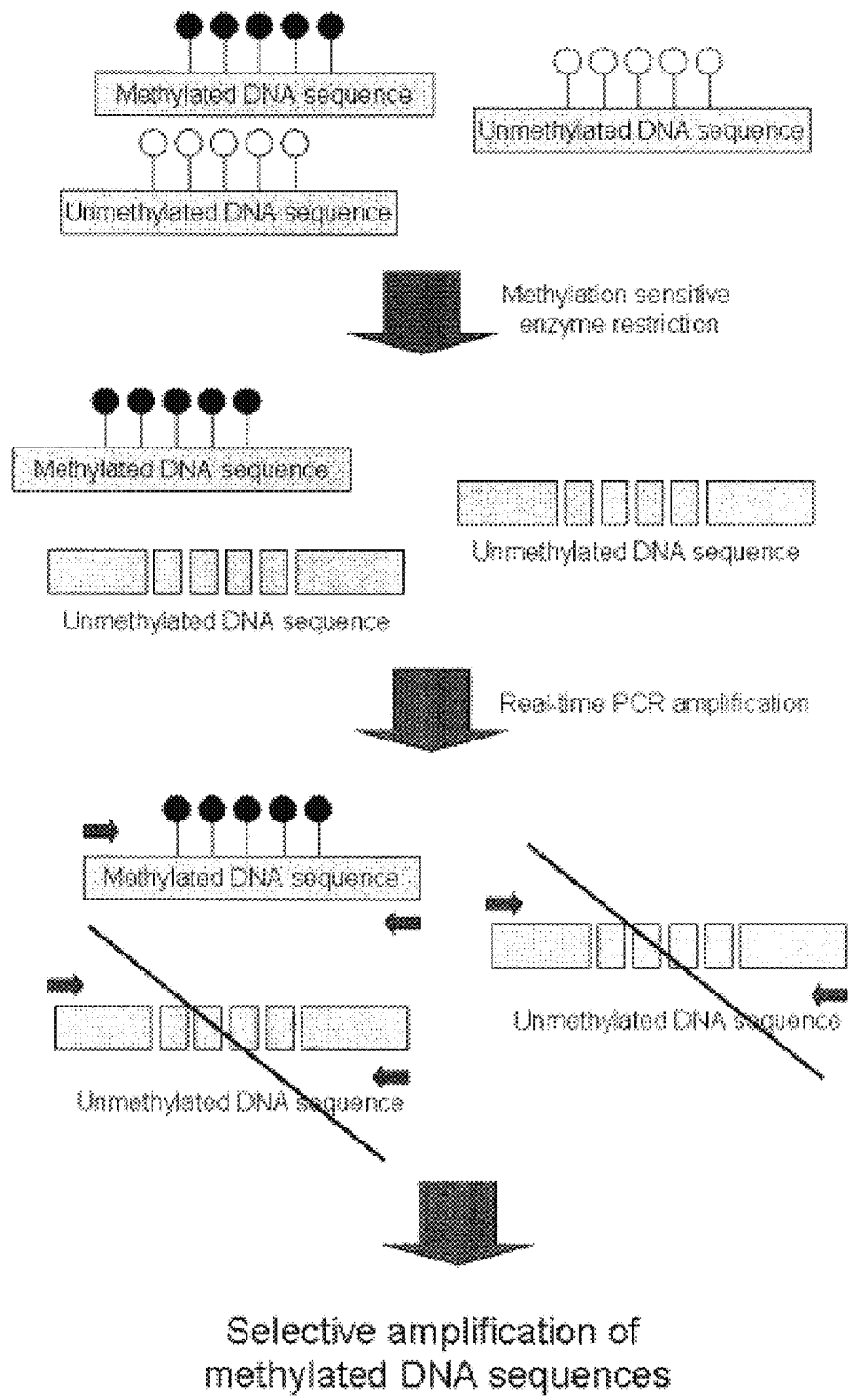
FIG. 8. Selective amplification of methylated DNA sequence. The circles connected to the gene sequence signify cleavage sites of methylation sensitive restriction enzyme. Open and filled circles represent unmethylated and methylated sequences, respectively, at these methylation sensitive restriction enzyme cleavage sites. The methylation sensitive restriction enzyme digestion cleaves unmethylated DNA sequence at the enzyme restriction sites. As a result, only uncleaved methylated DNA sequence could be detected in the real-time PCR amplification step.

Methylation sensitive enzymes are enzymes that cut DNA only when their recognition site is not methylated. For more description, see, e.g., U.S. patent application publication No. US 2005/0158739 (Jeddeloh et al.). For example, BstU I recognizes the CGCG site and cuts the DNA when the CpG is not methylated. As shown in FIG. 8, more than one methylation sensitive enzymes can be used to digest unmethylated DNA, leaving only the methylated sequences intact. Methods such as real-time PCR can be used subsequently to detect the DNA sequences which are still amplifiable after enzymatic digestion.

Materials and Methods

Subject Recruitment and Sample Collection

Subjects were recruited from the Department of Obstetrics and Gynaecology, Prince of Wales Hospital, Hong Kong. The study and the collection of human clinical samples were approved by the institutional review board. Informed consent was sought from each subject. Third trimester placental tissues were collected after elective cesarean delivery of uncomplicated pregnancies. Maternal peripheral blood samples were collected just prior to the performance of obstetric procedures.

Sample Processing and DNA Digestion by Methylation Sensitive Enzyme

Maternal blood samples were centrifuged at 1,600 g for 10 min and at 16,000 g for 10 min at 4° C. DNA was extracted from the 200 μl of buffy coat and 0.2 g of placental tissue using the QIAamp DNA Blood mini kit and the QIAamp DNA mini kit, respectively, following the manufacturer's recommendation. One hundred nanograms of placental and maternal buffy coat DNA were digested with 100 U of BstU I, a methylation sensitive enzyme, in 1× digestion buffer at 60° C. for 16 hours.

Real-Time PCR Detection for RASSF1A Sequence

RASSF1A sequence was amplified by real-time PCR using the primers RSF-b151F, 5'-AGCCTGAGCTCAT-TGAGCTG-3' and RSF-dsgnR, 5'-ACCAGCTGCCGT-GTGG-3', and the minor grove binding (MGB) fluorescent probe RSF-dsgnT, 5'-FAM-CCAACGCGCTGCGCAT-MGB-3'. The timing of or the number of PCR cycles required for the appearance of detectable fluorescent signal is inversely correlated with the amount of RASSF1A sequence in the input DNA sample. In other words, the higher the amount of RASSF1A sequence present in a DNA sample, the earlier the fluorescent signal would appear, resulting in a lower threshold cycle number.

Figure 9A:
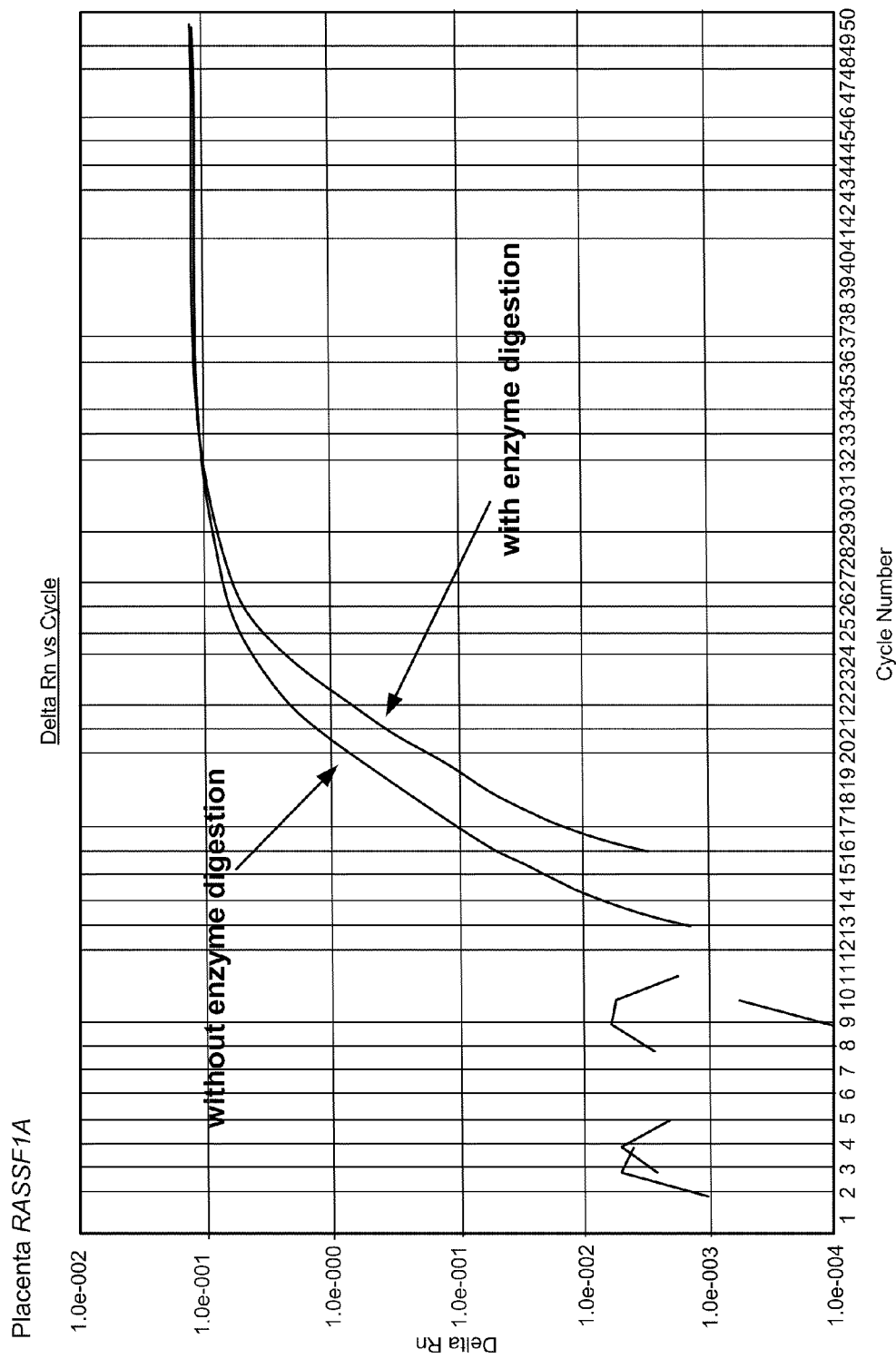
FIG. 9. (a) Real-time PCR amplification plots for RASSF1A in placental and maternal buffy coat DNA samples. After methylation sensitive restriction enzyme digestion, RASSF1A sequence was detected in the placental DNA sample, but not detected in the maternal buffy coat DNA sample. (b) Real-time PCR amplification for β-actin sequences in placental and maternal buffy coat DNA samples. After enzyme digestion, no β-actin was detected in the placental or maternal buffy coat DNA. (c) Methylation status of β-actin CpG island in third-trimester placental tissues and corresponding maternal blood cells. The analysed CpG sites are named according to the human cytoplasmic beta-actin gene GenBank Accession M10277 with the start codon of its protein coding sequence as position +1. The first CpG site (−970) corresponds to chr7:5536879 of the human genome in the UCSC Genome Browser (May 2004 assembly, hg17).
Figure 9A:
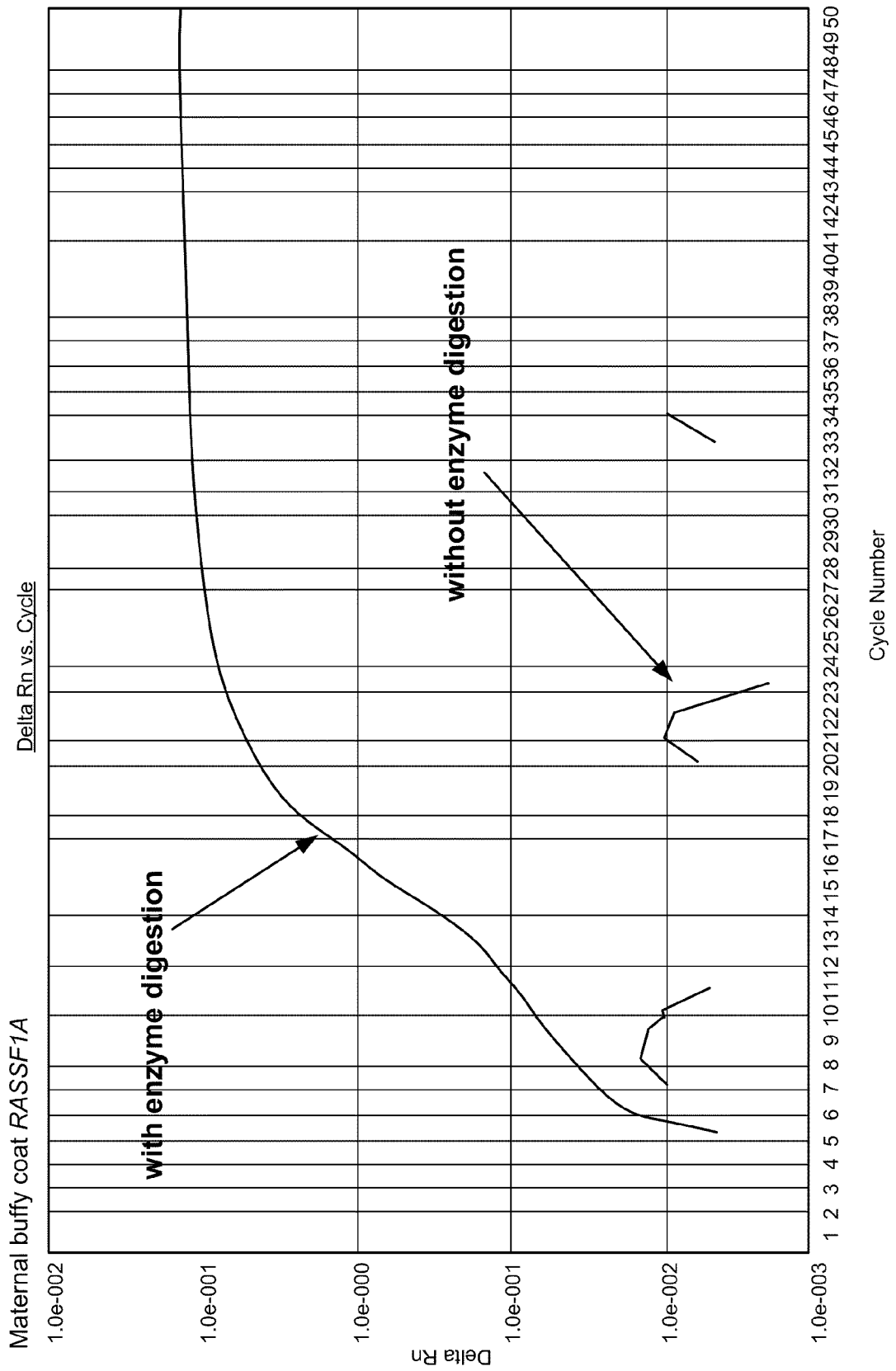
Figure 9B:
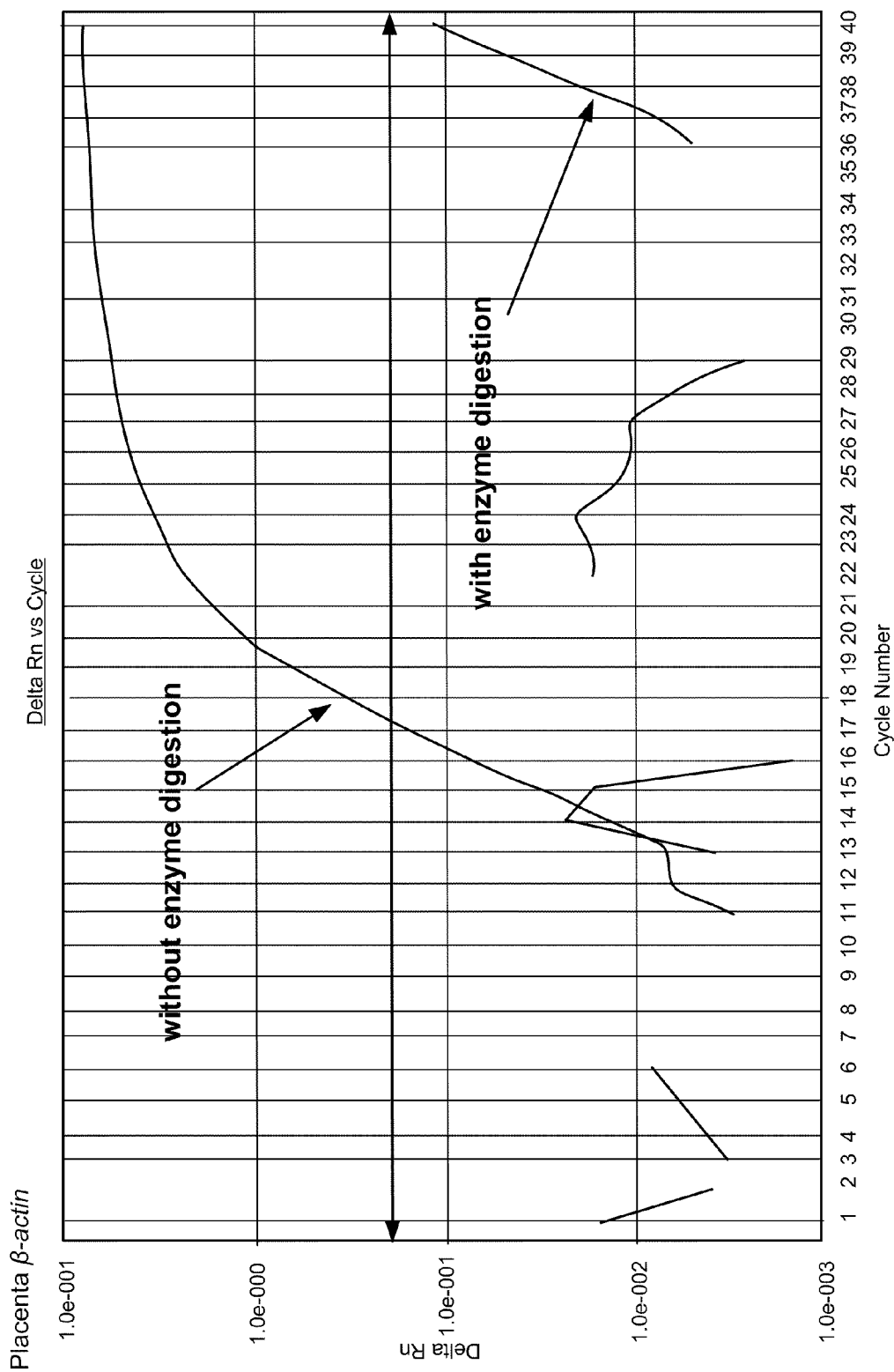
Figure 9B:
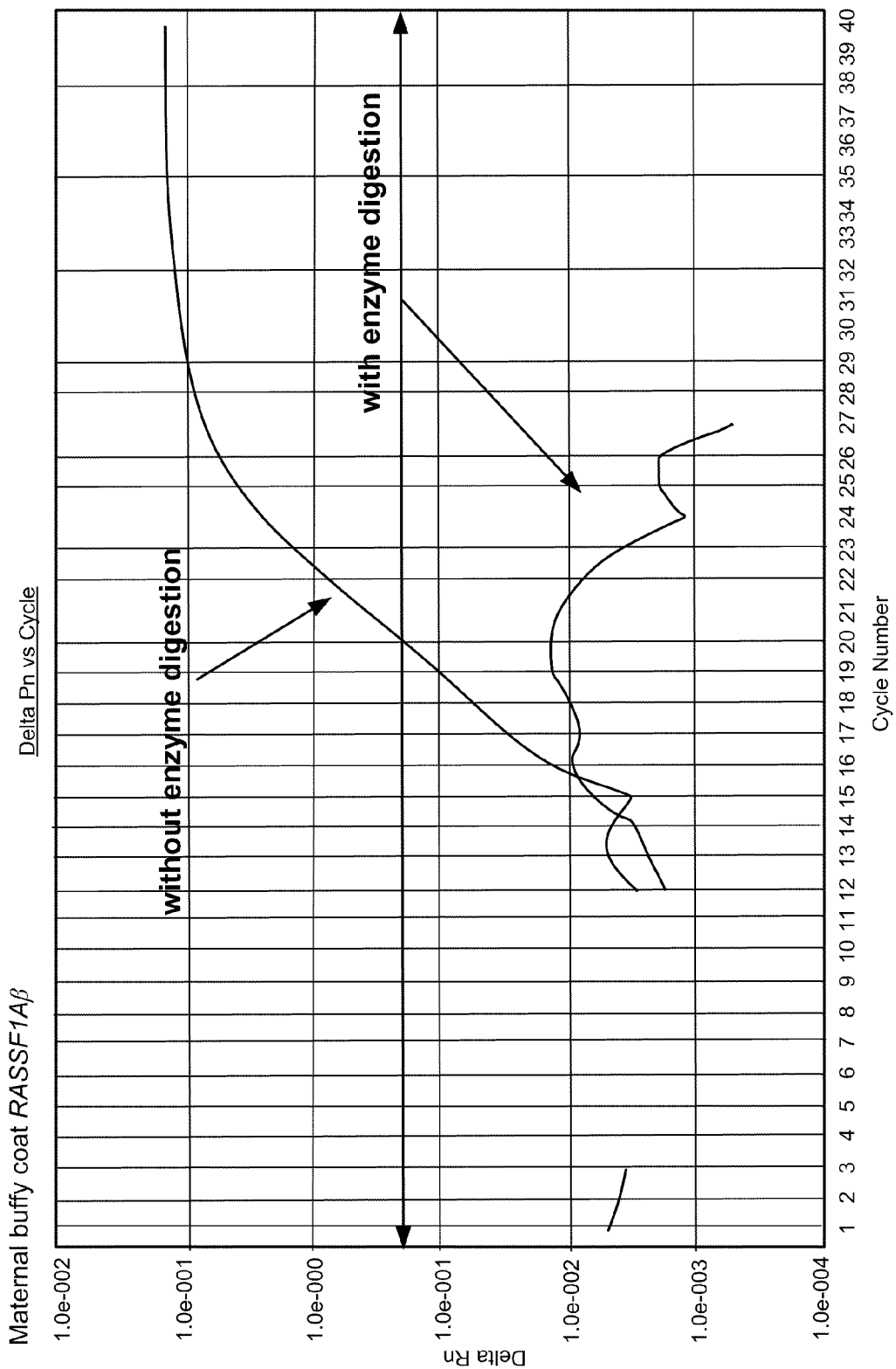
Figure 9C:
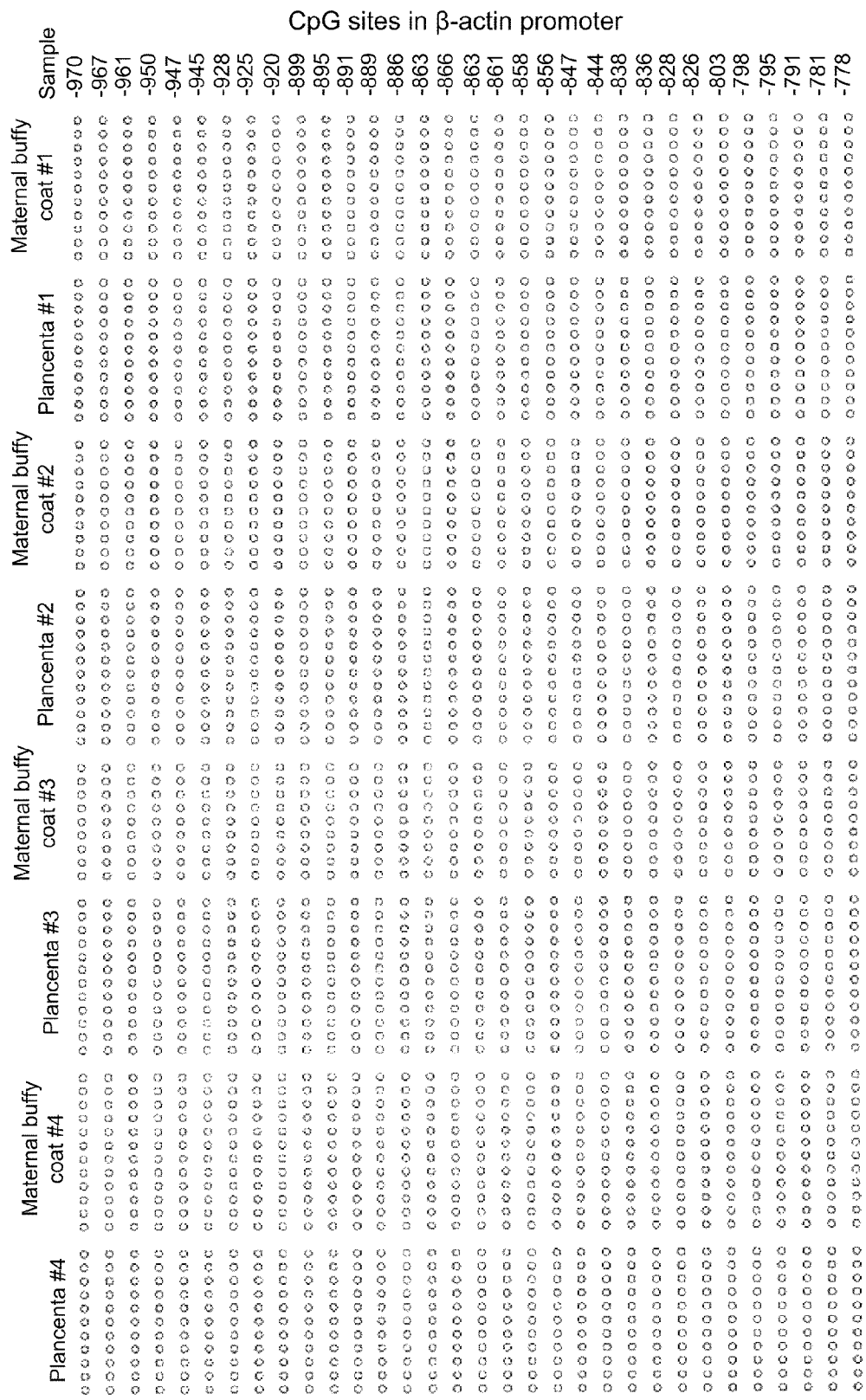

FIG. 9a shows an example of real-time PCR quantification of RASSF1A molecules from the placenta and maternal blood cells after BstU I digestion. Without enzyme digestion, RASSF1A molecules from both the placenta and maternal buffy coat were detected. With enzyme digestion, only RASSF1A molecules from the placenta were detected. For β-actin molecules, they were detectable only without enzyme digestion, regardless of their origins (FIG. 9b). It is expected since the β-actin sequence is not methylated. FIG. 9c shows the bisulfite sequencing results of the β-actin gene for the placenta and maternal buffy coat. Both the placenta tissues and maternal buffy coat were completely unmethylated.

Example 3

Detection of RASSF1A in Maternal Plasma after Enzymatic Digestion

In example 1, by bisulfite sequencing, we have demonstrated that the RASSF1A gene of maternal blood cells is completely unmethylated while that of the placenta (of fetal origin) is heavily methylated. In example 2, we have demonstrated that the RASSF1A sequences from maternal blood cells were completely digested by a methylation sensitive restriction enzyme, while the RASSF1A sequences from placenta were only partially digested by the same enzyme. Plasma DNA is composed of DNA of maternal origin (largely from maternal blood cells and thus is unmethylated) and DNA of fetal origin (placenta being a main contributor and thus is methylated for the markers described in this patent application). It is thus feasible to use methylation sensitive enzyme digestion of plasma DNA to remove the maternal DNA background and to increase the fractional concentration of the fetal-derived RASSF1A molecules in maternal plasma.

Figure 10A:
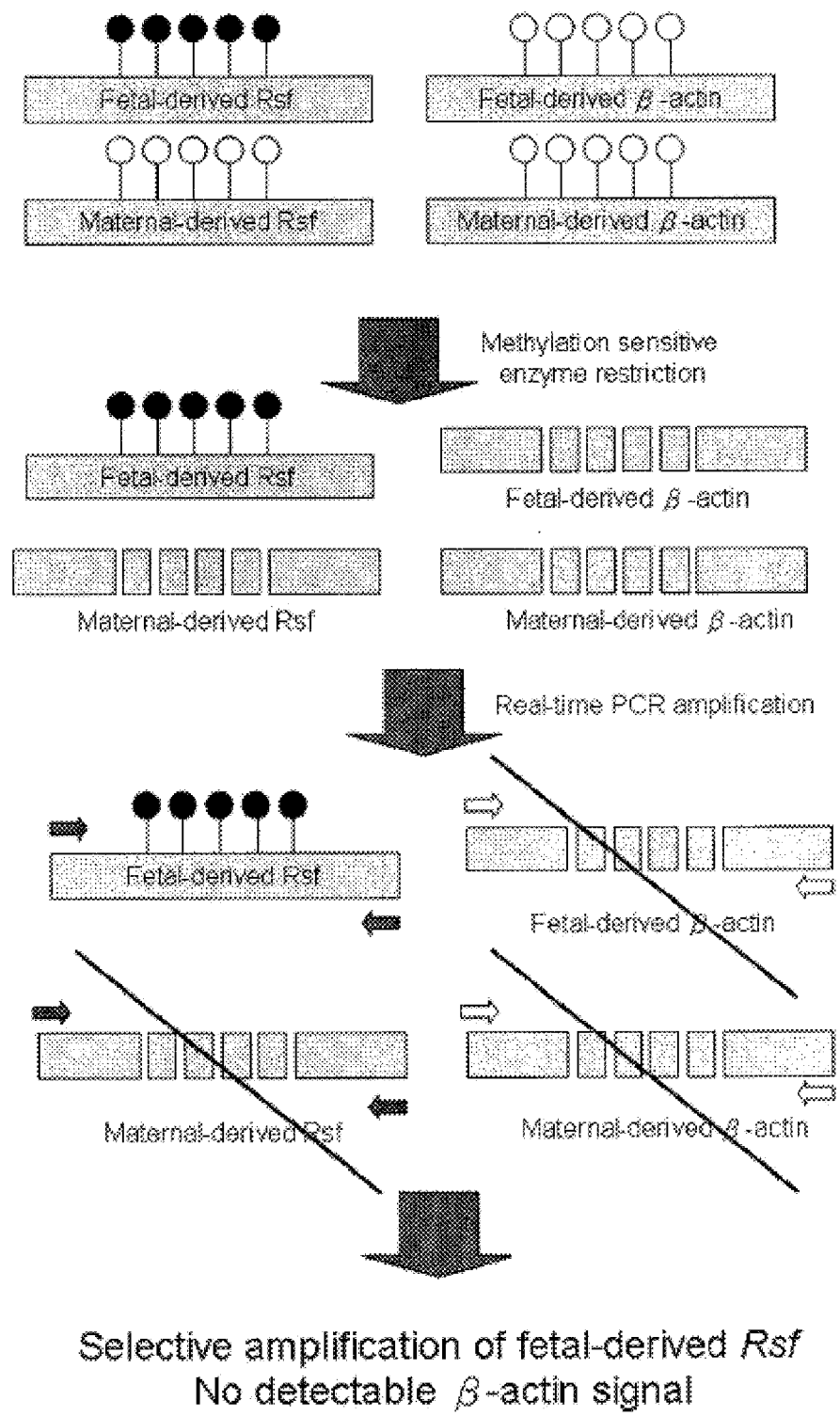
FIG. 10. (a) Schematic diagram showing the principle of the selective amplification of fetal-derived RASSF1A sequence in the maternal plasma DNA. The circles connected to the gene sequence signify cleavage sites of methylation sensitive restriction enzymes. Open and filled circles represent unmethylated and methylated sequences, respectively, at these methylation sensitive restriction enzyme cleavage sites. The methylation sensitive restriction enzyme digestion specifically digests unmethylated DNA at the enzyme restriction sites. As a result, maternal-derived RASSF1A (Rsf) and β-actin sequences, as well as fetal-derived β-actin sequence, would be digested, leaving detectable fetal-derived RASSF1A sequences. The filled and open arrows represent the PCR primers targeting the RASSF1A and β-actin genes, respectively. Therefore, only fetal-derived RASSF1A sequence could be detected by the real-time PCR system. (b) Schematic diagram illustrating the detection of incomplete enzyme digestion by the internal control of β-actin system. When the methylation sensitive enzyme digestion is incomplete, some maternal-derived RASSF1A and β-actin sequences, as well as some fetal derived β-actin sequences, would remain in the DNA sample. In this case, the RASSF1A signal, which may originate from both maternal-derived and fetal-derived sequences due to incomplete digestion, is not specific for fetal DNA. This internal control system is designed for minimizing the false positive detection due to incomplete enzymatic digestion.
Figure 10B:
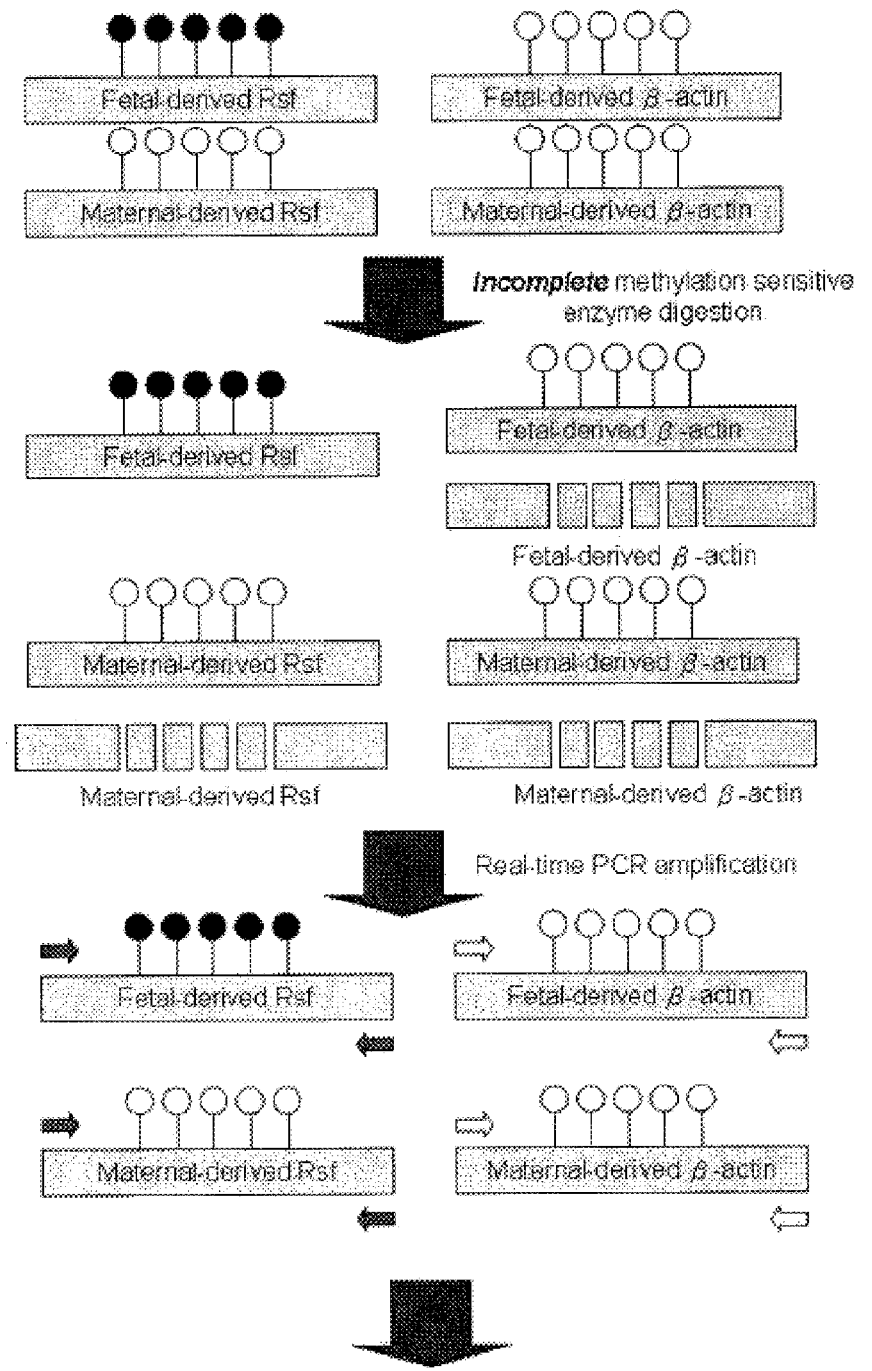
Figure 11A:
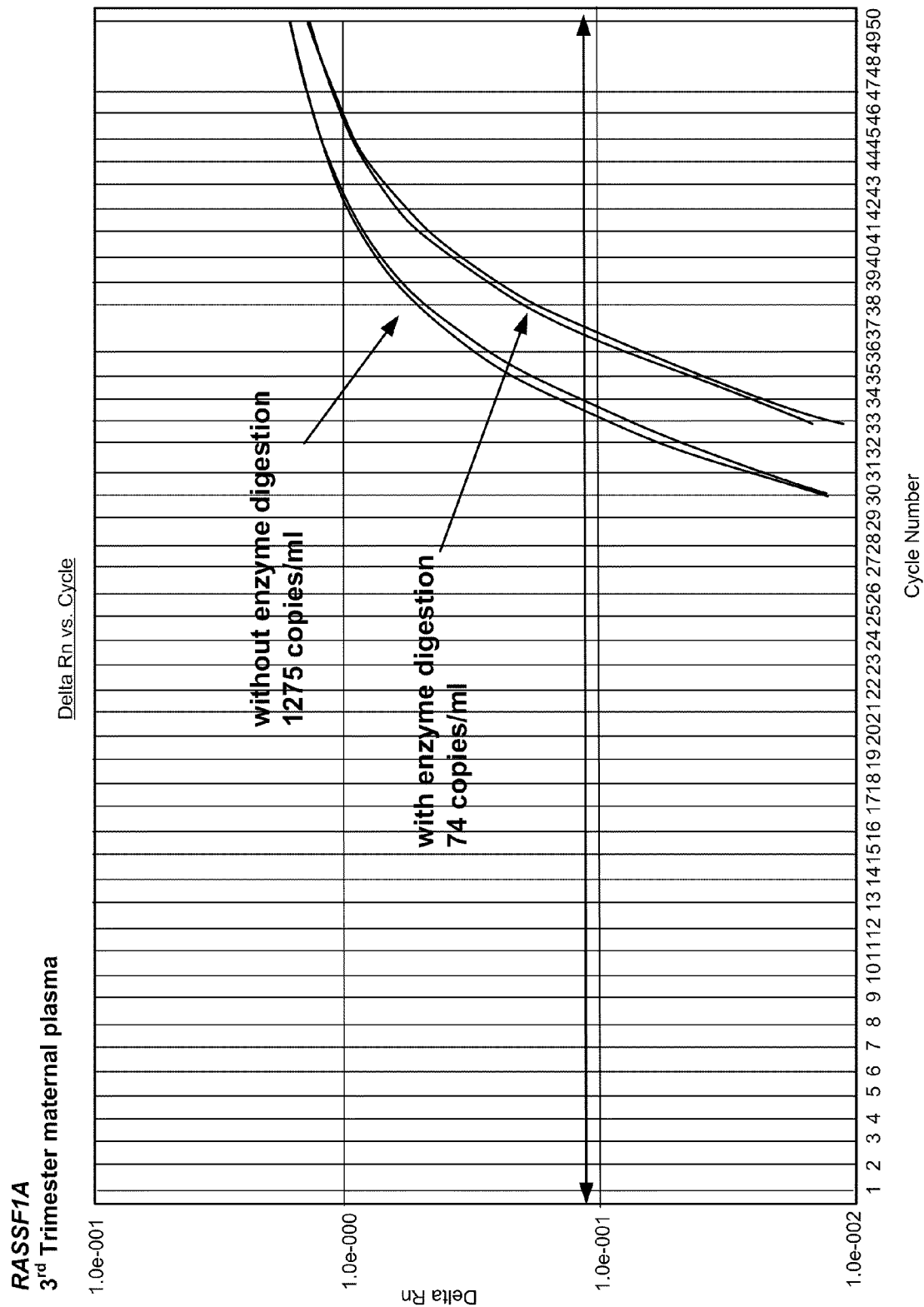
FIG. 11. Real-time amplification plots for RASSF1A and β-actin for the plasma DNA samples from a third trimester pregnant woman (a) and a first trimester pregnant woman (b). After enzymatic digestion, RASSF1A sequence remained detectable in the maternal plasma for both women. The right shift of the amplification curve is due to the reduction in the amount of RASSF1A sequence after the digestion of maternal-derived RASSF1A sequences by the methylation sensitive restriction enzyme. In contrast, β-actin sequences were digested by the enzyme, and were thus not detectable. The cell-free plasma DNA samples of 71 pregnant subjects were analyzed. Twenty-eight of them were in the first trimester of their pregnancy and 43 of them were in the third trimester. RASSF1A sequences were detectable in ALL of the plasma DNA samples after methylation sensitive enzyme digestion.
Figure 11A:
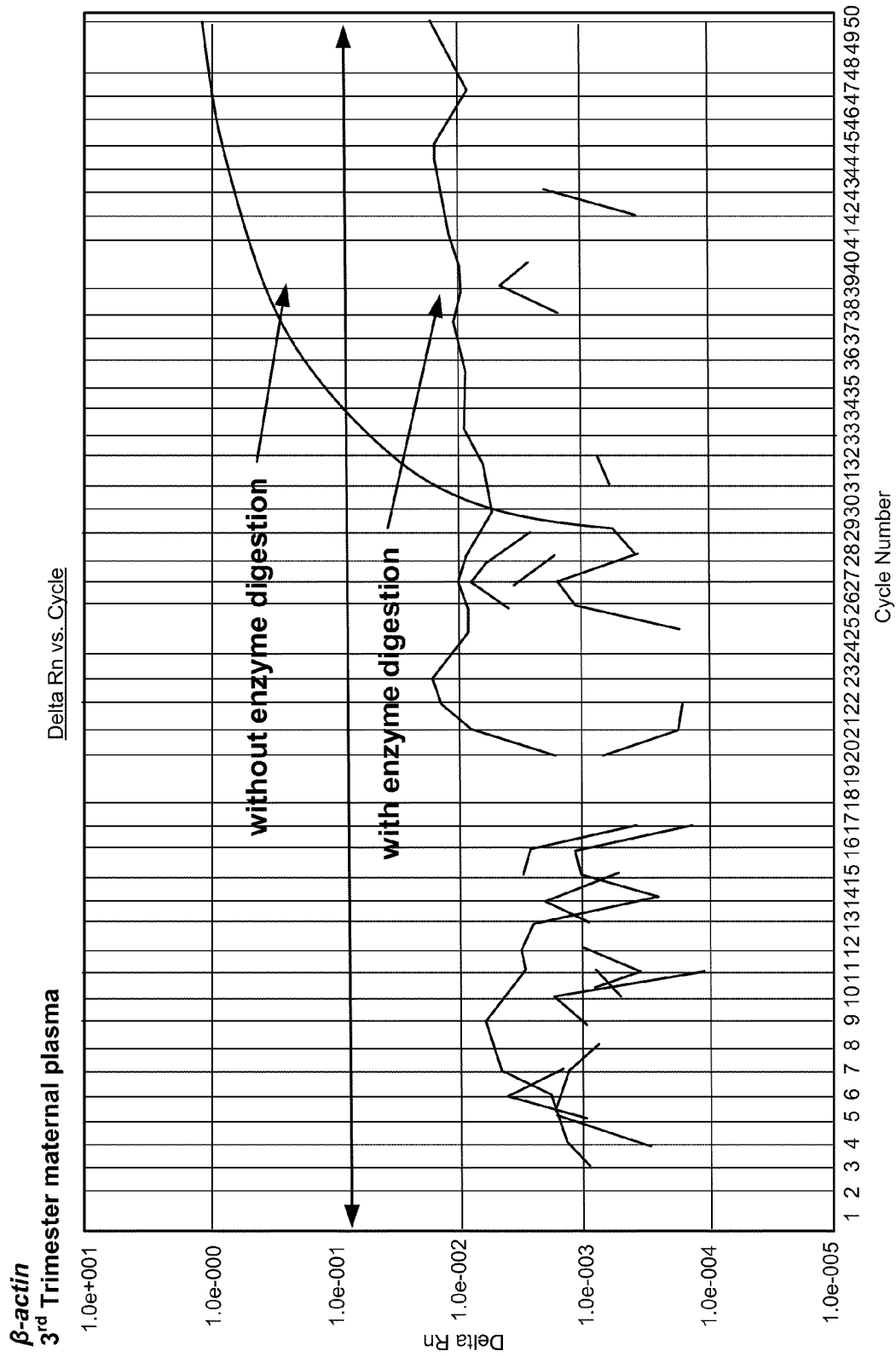
Figure 11B:
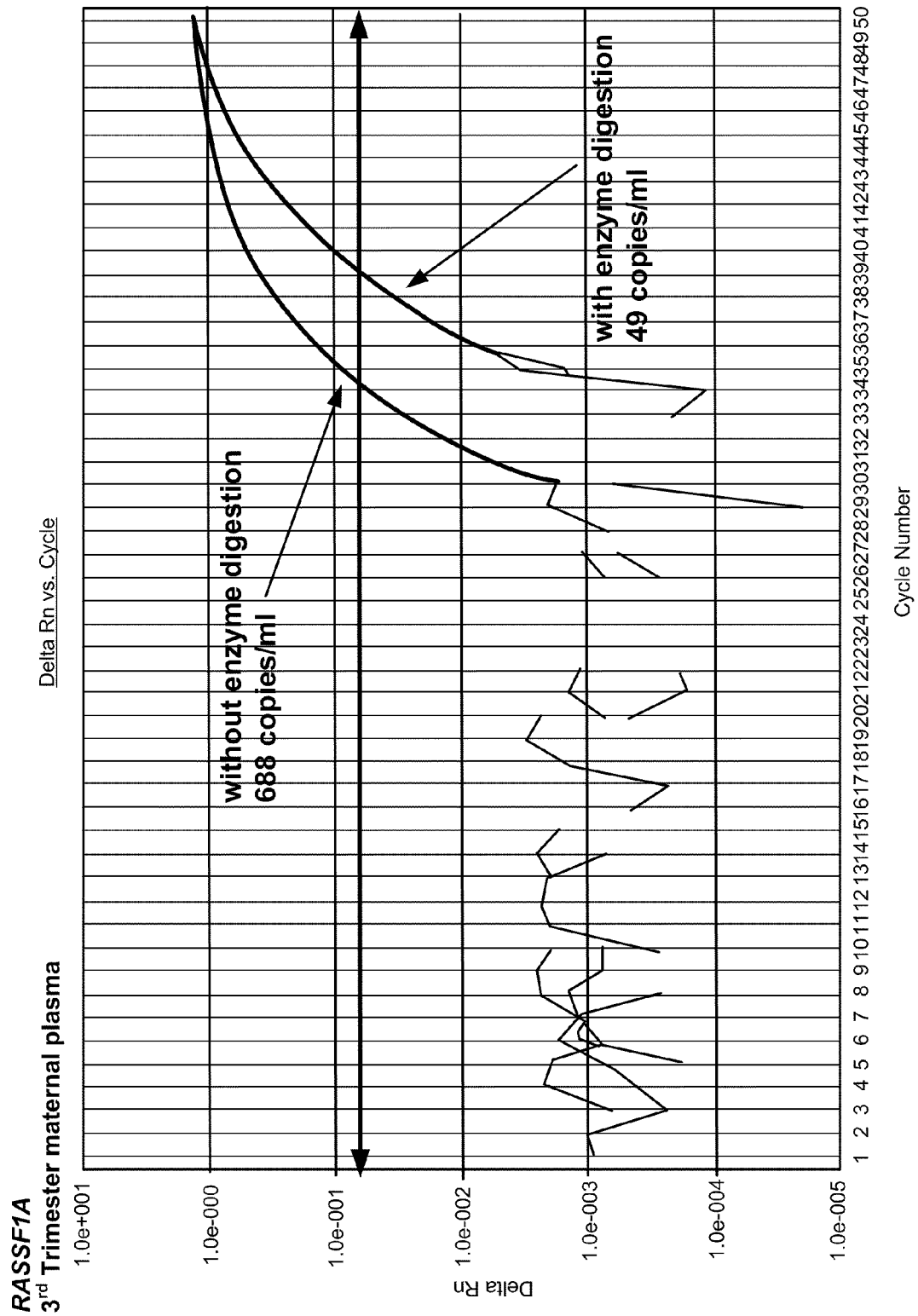
Figure 11B:
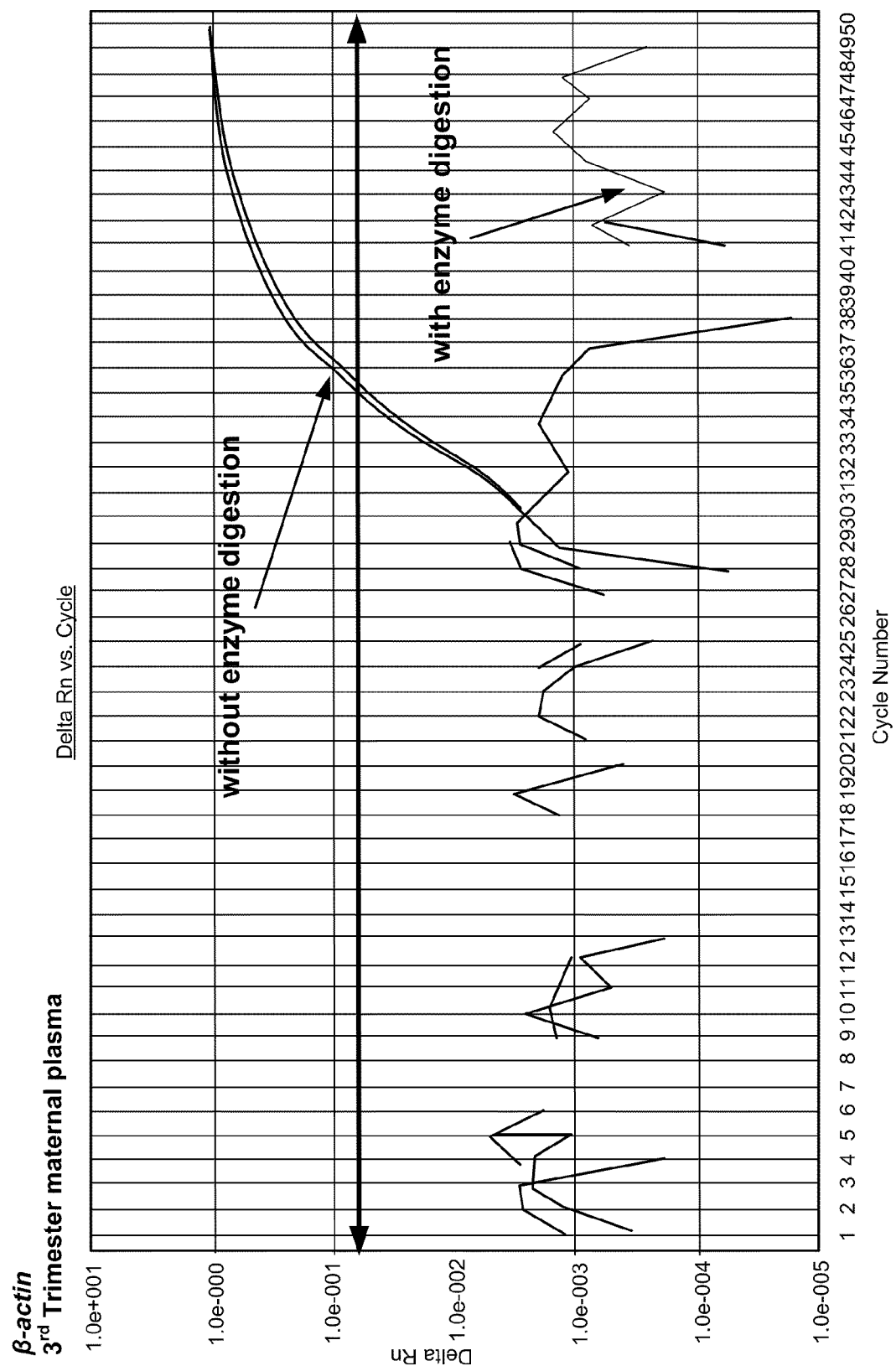

A schematic diagram is shown in FIG. 10a, maternal-derived RASSF1A is unmethylated and thus is digested by methylation sensitive enzyme while some of the fetal-derived RASSF1A is methylated and thus is not digested. If enzyme digestion is complete, only fetal-derived, methylated DNA is left intact and can serve as the template for PCR amplification. In the case of β-actin, since both the maternal and fetal-derived DNA sequences are unmethylated, complete enzyme digestion will destroy all sequences and subsequently no PCR amplification using this β-actin sequence can be achieved. Human errors and reagent quality sometimes may cause incomplete enzyme digestion. Beta-actin can thus be used as an internal control to indicate incomplete digestion (FIG. 10b). If PCR amplification is successful for β-actin after enzyme digestion, it is likely that the enzyme digestion is incomplete. In this case, the entire assay may need to be repeated until a negative result is achieved for the β-actin assay.

Materials and Methods

Sample Processing and DNA Digestion by Methylation Sensitive Enzyme

Maternal blood samples were centrifuged at 1,600 g for 10 min and at 16,000 g for 10 min at 4° C. DNA was extracted from 1.6 ml plasma using the QIAamp mini kit (Qiagen) and eluted with 50 μl of $H_2O$. Thirty-five microliters of plasma DNA were digested with 100 U of BstU I enzyme, in 1× digestion buffer at 60° C. for 16 hours.

Real-Time PCR Detection for RASSF1A and Beta-Actin Sequences

RASSF1A sequence was amplified and quantified by real-time PCR as described above. Beta-actin sequence was amplified and quantified by real-time PCR using the primers Actin-163F, 5'-GCGCCGTTCCGAAAGTT-3' and Actin-298R, 5'-CGGCGGATCGGCAAA-3', and the MGB fluorescent probe Actin-243T, 5'-VIC-ACCGCCGAGAC-CGCGTC-MGB-3'. SRY sequence was amplified and quantified using the primers SRY-109F, 5'-TGGCGAT-TAAGTCAAATTCGC-3' and SRY-245R, 5'-CCCCCTAG-TACCCTGACAATGTATT-3', and the fluorescent probe SRY-142T, 5'-FAM-AGCAGTAGAGCAGTCAGGGAG-GCAGA-TAMRA-3'. A DNA construct containing one copy each of the RASSF1A, SRY and β-actin amplicons was established as the quantitative standard of the three assays. A calibration curve was created by serial dilutions of a known quantity of the DNA construct and was included in each round of real-time PCR for the quantification of plasma RASSF1A, β-actin and SRY.

FIG. 11 shows an example of real-time PCR quantification of RASSF1A molecules from $1^{st}$ and $3^{rd}$ trimester maternal plasma with and without BstU I digestion. For the 1st trimester sample, RASSF1A concentration was reduced from 688 copies/mL plasma to 49 copies/mL plasma due to enzyme digestion. This dramatic reduction is expected since the majority (on average 96.6%, Lo et al., *Am J Hum Genet* 1998, 62: 768-775) of the DNA molecules are of maternal origin, and thus are unmethylated and digested. For the third trimester sample, RASSF1A concentration was reduced from 1275 copies/mL plasma to 74 copies/mL plasma due to enzyme digestion. We have analyzed 71 pregnant women (28 in 1st trimester and 43 in $3^{rd}$ trimester) using this assay on RASSF1A molecules. RASSF1A sequences were detectable in all of the plasma DNA samples after methylation sensitive enzyme digestion. Beta-actin digestion control was analyzed for all the samples. For every case, β-actin sequence was detected only without enzyme digestion.

Example 4

Demonstration of Fetal-Specificity of RASSF1A Sequence in Maternal Plasma after Enzymatic Digestion Fetal-specificity of the DNA sequences after enzymatic digestion is important for the application to prenatal diagnosis and pregnancy monitoring. In this example, we shall demonstrate the fetal-specificity of RASSF1A sequence after enzymatic digestion in maternal plasma by four lines of experiments.

Figure 12:
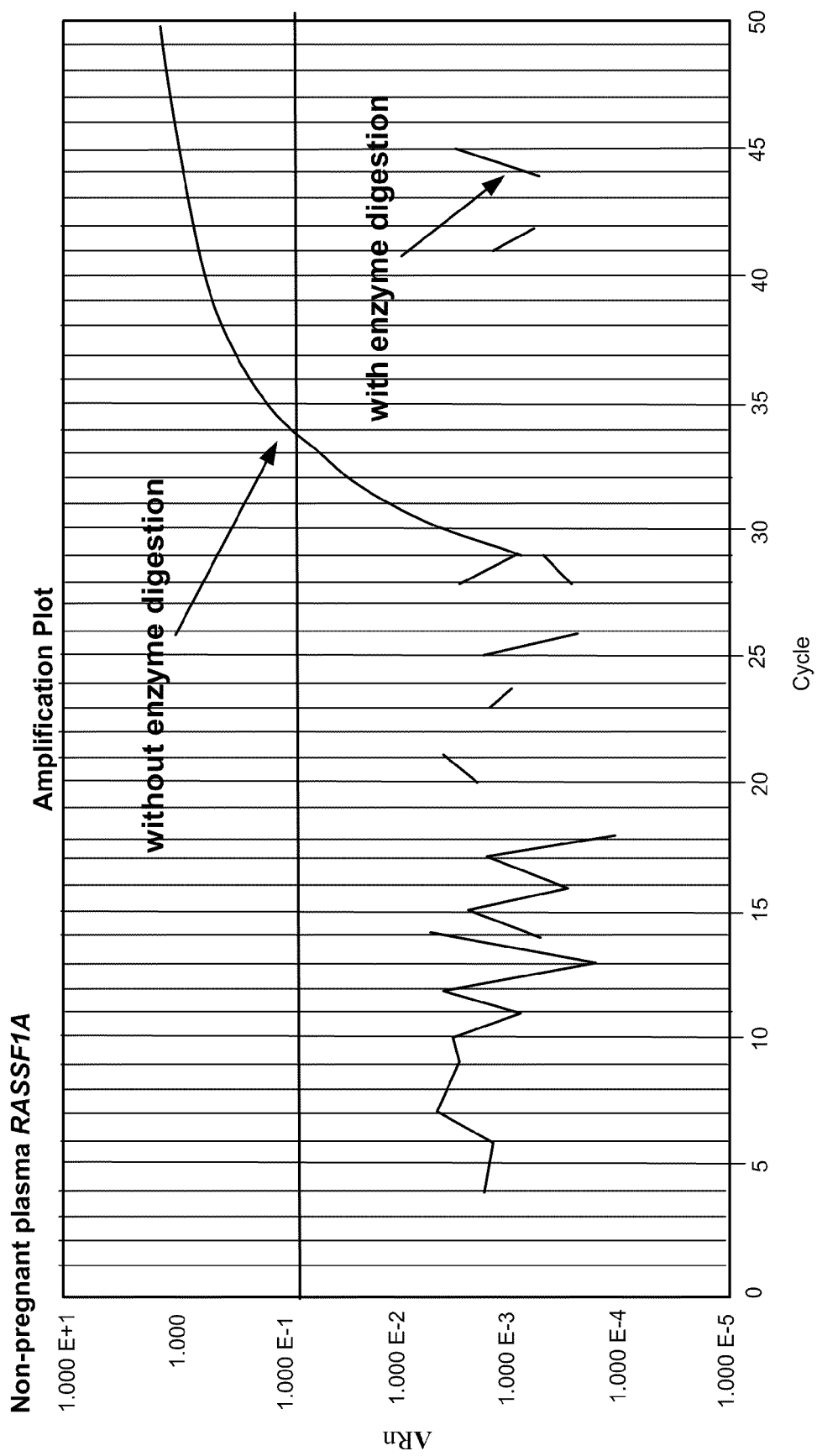
FIG. 12. Real-time amplification plots for RASSF1A and β-actin for the maternal plasma DNA from a non-pregnant woman. After enzyme digestion, no RASSF1A or β-actin sequence was detected in the plasma DNA sample. In the 25 non-pregnant females recruited for this study, none showed detectable RASSF1A signal in the plasma after methylation sensitive restriction enzyme digestion.
Figure 12:
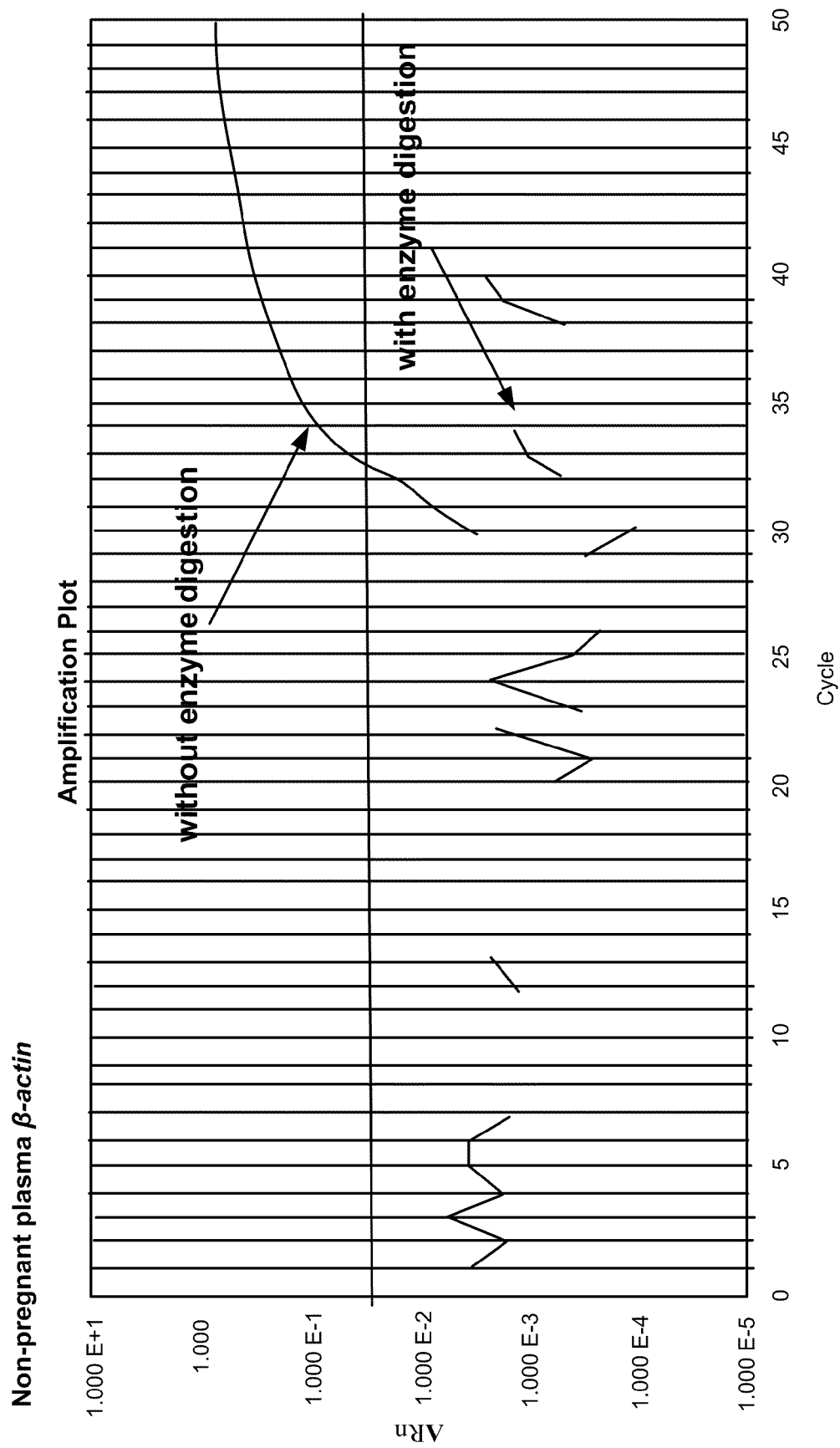

In the first experiment, it is demonstrated that the RASSF1A sequence was not detectable after enzymatic digestion in non-pregnant women. This is important since if the RASSF1A molecules after enzymatic digestion are fetal-specific, they should not be detected in non-pregnant women. In FIG. 12, one case of non-pregnant women is shown. RASSF1A sequence was only detected without enzyme digestion. With enzyme digestion, no detectable RASSF1A sequence was found. As expected, the β-actin digestion control was only detected without enzyme digestion. In the 25 non-pregnant volunteers we have recruited for this study, none of them showed detectable RASSF1A signal in the plasma after methylation sensitive restriction enzyme digestion.

In the second experiment, it is demonstrated that the RASSF1A sequence after enzymatic digestion was not detectable after the delivery of the baby. If the RASSF1A molecules after enzymatic digestion are fetal specific, it is expected that they will disappear from the maternal plasma since the sources (placenta being a main one) that release such molecules are removed after delivery. Other fetal specific markers such as SRY had been shown to demonstrate similar clearance after delivery (Lo et al., *Am J Hum Genet* 1998, 62: 768-775). Five pairs of pre- and post-delivery maternal plasma samples were collected. For all cases, after enzymatic digestion, RASSF1A molecules were detectable before delivery, but not detectable after delivery (Table 1). Similarly, the fetal-specific SRY marker was only detectable before delivery.

In the third experiment, a single nucleotide polymorphism (SNP) marker was used to distinguish the maternal-derived and fetal-derived RASSF1A sequences. If the RASSF1A sequences after enzymatic digestion are indeed fetal specific, then the genotype of such sequences should be that of the fetus, instead of that of the mother. For example, if a SNP marker is CC in the fetus and AC in the mother, the genotype of the DNA after enzymatic digestion should be CC, instead of AC. Similarly, for an AC/CC (fetal/maternal) pair, the genotype of the DNA after enzymatic digestion should be AC, instead of CC. For the plasma DNA without digestion, the genotype may be the same as that of the mother, since the majority of the plasma DNA is of maternal origin.

Materials and Methods

RASSF1A Genotyping

DNA was extracted from maternal plasma, maternal buffy coat and placenta as described above. Thirty-five microliters of each maternal plasma DNA sample were subjected to BstU I enzyme digestion for 16 hours as described above. PCR amplification of the RASSF1A sequence was performed with the primers RSF-b151F, 5'-AGCCTGAGCTCAT-TGAGCTG-3' and RSF-dsgnR, 5'-ACCAGCTGCCGT-GTGG-3' using maternal buffy coat DNA, placental DNA, maternal plasma DNA without enzymatic digestion and maternal plasma DNA after enzymatic digestion as templates. As there is a single nucleotide polymorphism (SNP id: rs4688725) within this RASSF1A amplicon, the RASSF1A genotypes of different tissues may be determined. A primer extension reaction was set up for the genotyping of RASSF1A DNA. Each 14 μl reaction contained 10 μl of PCR products, 0.77 μM extension primer Rsf-R17 5'-CAGC-CGGGTGGGCCCT-3', 1.15 U thermosequenase and a mixture of dideoxynucleotides (ddATP, ddCTP and ddTTP) and the deoxynucleotide dGTP (64 μM each). For RASSF1A sequence with a genotype A, the primer would be extended to produce 5'-CAGCCGGGTGGGCCCTddT-3' with a molecular weight of 5476.6 Da. For RASSF1A sequence with a genotype C, the primer would be extended to produce 5'-CAGCCGGGTGGGCCCTGddC-3' with a molecular weight of 5790.8 Da. The final base extension products were analyzed by the MassARRAY MALDI-TOF mass spectrometry (SEQUENOM). The genotype of the RASSF1A was determined by the TyperAnalyzer software (SEQUENOM).

Figure 13:
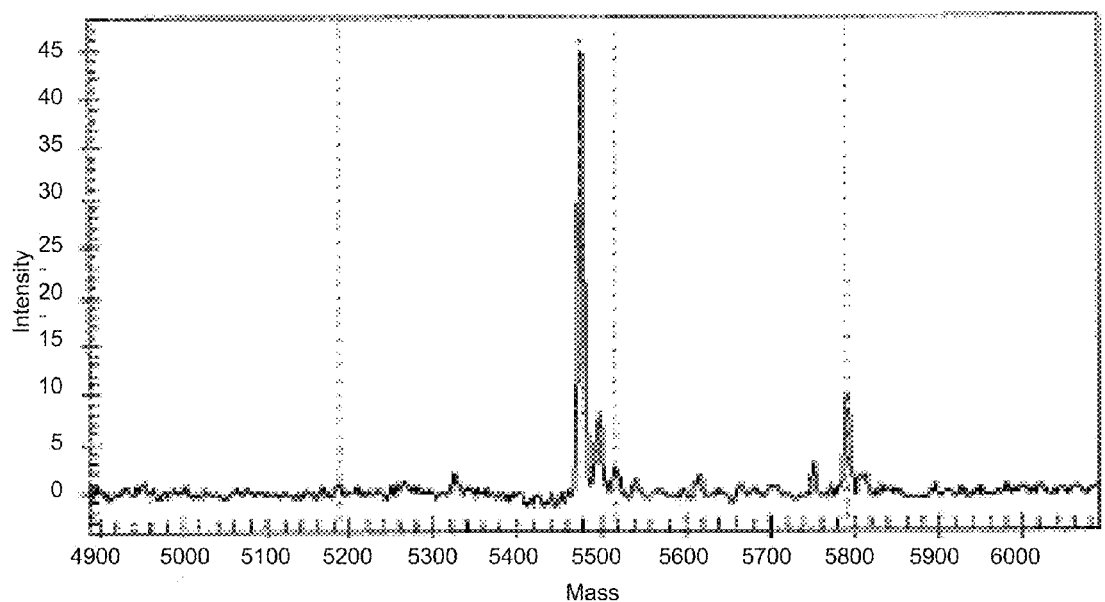
FIG. 13. In this case, the RASSF1A genotypes of the mother (maternal buffy coat DNA) and the fetus (placental DNA) were AC and CC, respectively. Without enzyme digestion, the RASSF1A genotype of the maternal plasma was identical to that of the mother which was AC. After enzyme digestion, the RASSF1A genotype of the maternal plasma changed to CC which was identical to the placental (fetal) genotype.
Figure 13:
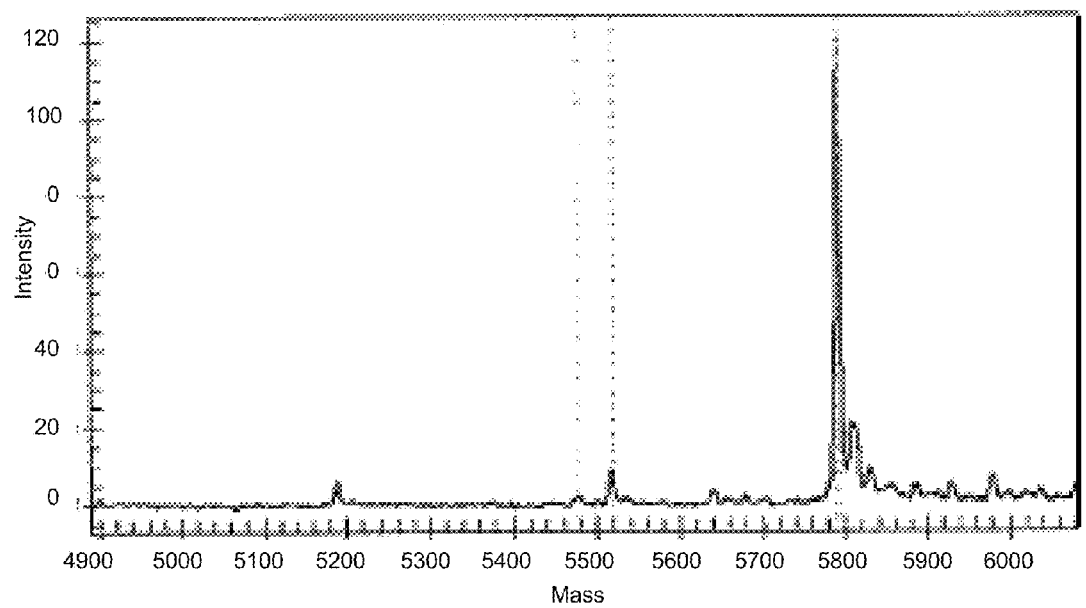
Figure 13:
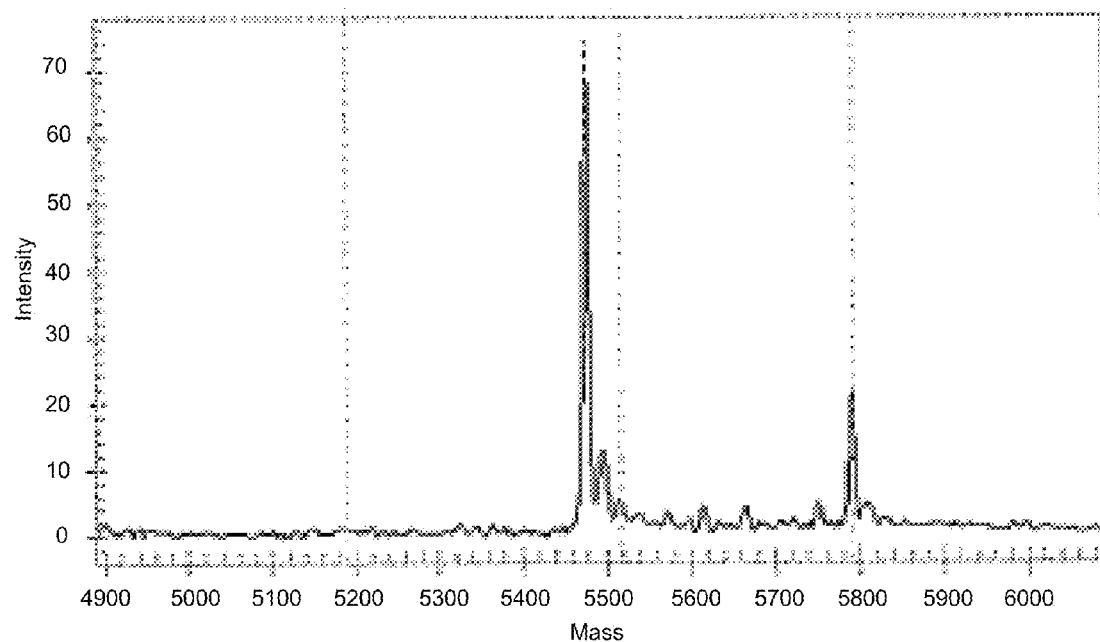
Figure 13:
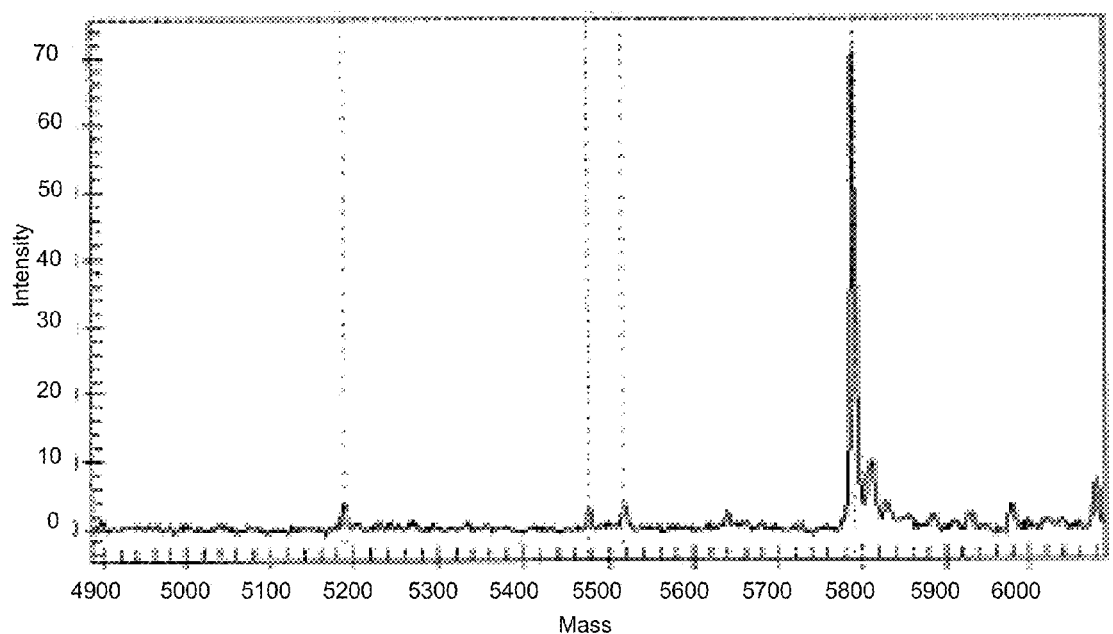

FIG. 13 shows an example of the genotyping experiment result for maternal plasma DNA with or without enzyme digestion, maternal buffy coat DNA and placental DNA. As expected, the genotype of the maternal plasma DNA after enzymatic digestion was the same as that of the placenta (fetal genotype), but not that of the maternal buffy coat. Table 2 shows the genotyping results for 43 cases where maternal plasma DNA with or without enzyme digestion, maternal buffy coat DNA and placental DNA were all analyzed. In each of the 43 cases, the genotype of the maternal plasma DNA after enzymatic digestion was identical to the placental (fetal) genotype.

Figure 14:
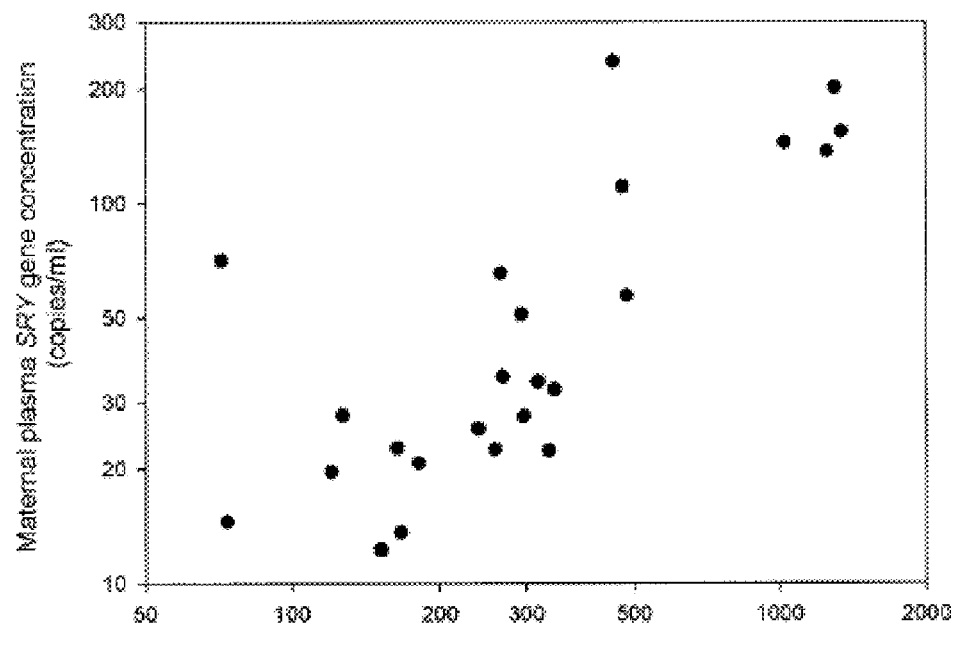
FIG. 14. Correlations of the concentrations of SRY sequence vs. RASSF1A sequence in the maternal plasma with or without enzyme digestion for 24 third trimester pregnant women. All subjects were carrying a male fetus. There was a positive correlation between the concentrations of SRY and RASSF1A in the maternal plasma with enzyme digestion ($r=0.717$, $p<0.0001$, Spearman correlation). However, there is no correlation between the concentrations of SRY and total RASSF1A measured without enzyme digestion ($r=0.228$, $p=0.280$, Spearman).

In the fourth experiment, we demonstrated that two markers, namely the RASSF1A sequence after enzymatic digestion and SRY sequence, had concentrations in the maternal plasma that correlated with each other. Plasma DNA was extracted from 24 $3^{rd}$ trimester pregnant women carrying a single male fetus. As shown in FIG. 14, a positive correlation was observed between RASSF1A sequence after enzymatic digestion and SRY sequence (r=0.717, p<0.0001, Spearman correlation). Additionally, the concentration of total RASSF1A without enzymatic digestion, which was derived predominantly from the mother, did not correlate with that for SRY.

These four experiments demonstrated, conclusively, that the RASSF1A sequence after enzymatic digestion was exclusively (to the extent of the techniques we used) of fetal origin. RASSF1A is thus useful for prenatal diagnosis and pregnancy monitoring.

Example 5

Demonstration of RASSF1A as a Positive Analytical Marker for Prenatal Diagnosis of RhD Blood Type Rhesus D (RhD) blood group incompatibility is an important cause of hemolytic disease of the fetus and newborn. The pathogenesis of this disorder involves alloimmunization of a RhD negative pregnant woman by RhD antigen encoded by the paternal allele and displayed on the surface of fetal red cells. Maternal alloimmunization usually occurs during delivery when the tissue of a RhD positive fetus comes into contact with maternal blood. This would generate anti-RhD antibodies that can cross the placenta and destroy fetal red cells in the subsequent pregnancies with a RhD positive fetus. Maternal alloimmunization can be prevented or minimized by giving prophylactic anti-RhD immunoglobulin before and after the delivery of the first RhD positive baby. Therefore, it is beneficial to know the RhD status of a fetus before delivery. However, obtaining fetal cells for RhD genotyping/phenotyping by amniocentesis carries a risk of transplacental hemorrhage, which, if the fetus is RhD positive, could sensitize the maternal production of anti-RhD. The development of non-invasive prenatal RhD genotyping offers a safe alternative to obtaining fetal cells for RhD genotyping (Lo et al., *N Engl J Med* 1998; 339: 1734-1738). This technique involves the detection of fetal RhD sequence in the maternal plasma. The presence of RhD sequence in the plasma of a RhD negative pregnant women would indicate a RhD positive fetus. However, the absence of such sequence in the maternal plasma can be interpreted in two ways: 1) the fetus is RhD negative; or 2) there is inadequate fetal DNA in the maternal plasma to allow accurate fetal RhD typing. A universal fetal DNA marker as a positive control in the maternal plasma DNA would be useful to exclude the second possibility. The detection of the positive control fetal DNA marker in maternal plasma DNA would support the presence of a RhD negative fetus while the absence of the fetal DNA marker would suggest inadequate fetal DNA in maternal plasma. To date, available fetal DNA markers that can be used as positive control include Y chromosomal DNA and DNA polymorphisms. Both of these two types of markers are only applicable to a subset of pregnancies. Y chromosomal DNA is only applicable to pregnancies with a male fetus. DNA polymorphism is only applicable to particular genotype combinations where certain genotype is present only in the fetus, but not in the pregnant woman. In this regard, the methylated RASSF1A sequence illustrated in the above sections could be used as a universal fetal DNA marker that is applicable to all pregnancies regardless of the gender or polymorphism of the fetus. Those of skill in the art will also recognize that, besides the methylated RASSF1A marker, the other markers described herein could also be used in such a fashion.

Figure 15:
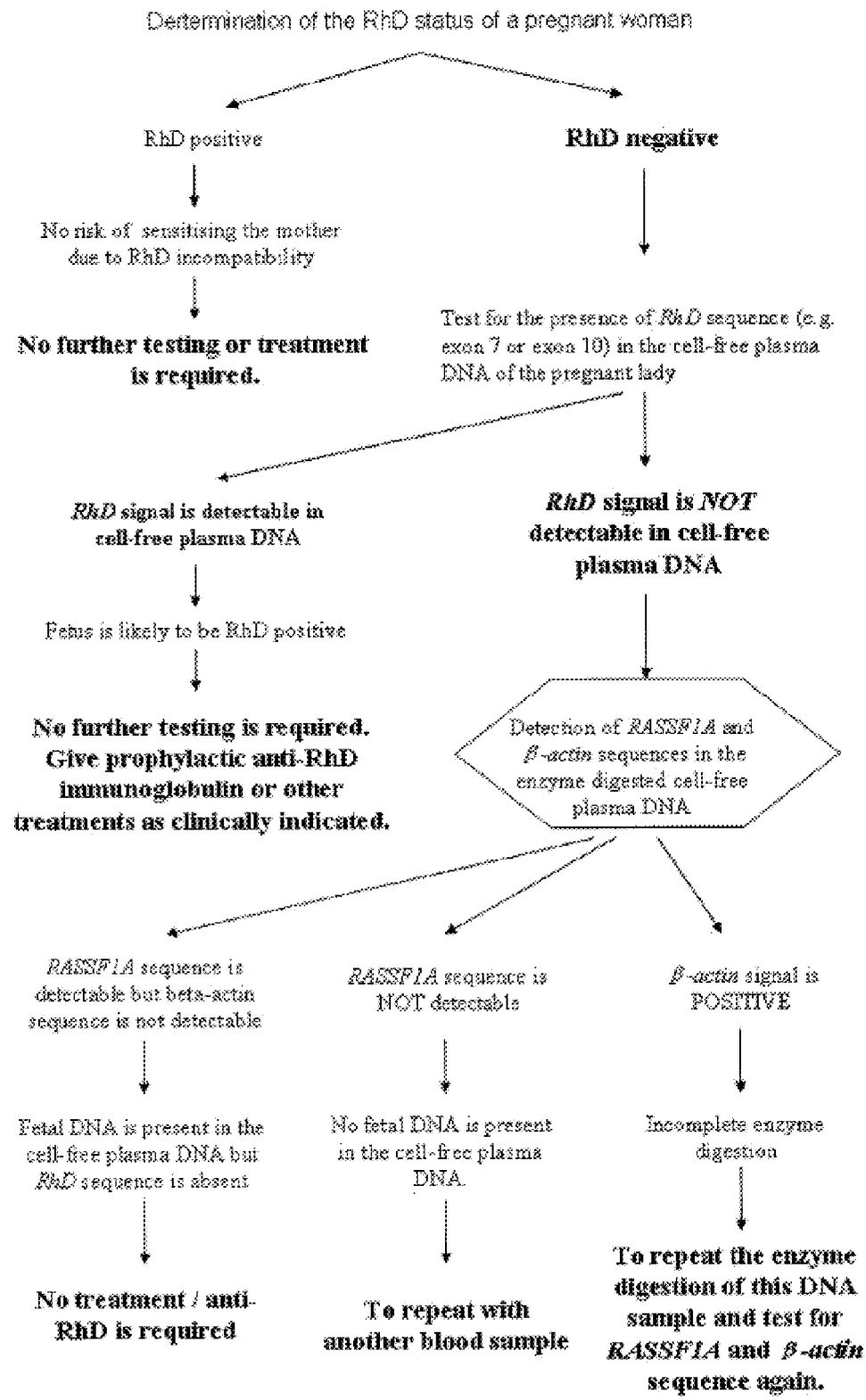
FIG. 15. Schematic diagram showing the strategy of non-invasive fetal rhesus D testing in pregnant women.

FIG. 15 shows a schematic diagram outlining one strategy for non-invasive RhD typing of the fetus. This is by no means the only way that a hypermethylated fetal DNA marker can be used as a positive analytical marker for prenatal diagnosis of RhD blood type. Those of skill in the art can also appreciate that a hypermethylated fetal DNA marker such as RASSF1A can be used as a positive analytical marker for prenatal diagnosis of other conditions, such as β-thalassemia, cystic fibrosis, congenital adrenal hyperplasia, and chromosomal aneuploidies. This positive analytical marker may also be assessed prior to, or simultaneously with the actual prenatal assessment of a condition such as RhD blood type.

Materials and Methods

Subject Recruitment and Sample Collection

Subjects undergoing first trimester Down syndrome screening were recruited from the King's College Hospital London, United Kingdom. The study and the collection of human clinical samples were approved by the institutional review board. Informed consent was sought from each subject. Chorionic villus tissues were collected via chorionic villus sampling procedure. Maternal peripheral blood samples were collected just prior to the performance of obstetrics procedures.

Sample Processing and Real-Time PCR Detection for RHD Sequences

DNA was extracted from maternal plasma, buffy coat and CVS samples as described in previous sections. The RhD status of the mother and the fetus were determined by real-time amplification of a sequence on the exon 7 and exon 10 of the RHD gene as described previously (Lo et al., *N Engl J Med* 1998, 339: 1734-1738; Rijnders et al., *Obstet Gynecol* 2004, 103:157-164) using maternal buffy coat DNA and CVS DNA as templates, respectively. In our cohort, the exon 7 and exon 10 assays gave identical results for all subjects studied. The detectability of RHD sequence in the maternal plasma was determined by the same real-time PCR systems using 5 μl plasma DNA as templates. All experiments were carried out in duplicates. A sample would be scored as positive if any of the duplicates was positive. The presence of fetal DNA in the maternal plasma was confirmed by the amplification of SRY sequence (for male fetuses) and the RASSF1A sequence after enzymatic digestion from the maternal plasma DNA. The real-time PCR targeting the SRY gene was carried out using plasma DNA without enzymatic digestion as the templates. The real-time PCRs for RASSF1A and β-actin sequences were carried out using maternal plasma DNA after enzymatic digestion as the templates.

Results

The RhD status of 355 pregnant women was screened. Fifty-four of them were RHD negative. As this group of subjects were at risk of alloimmunization by a RhD positive fetus, their plasma and CVS were subjected to further investigation for fetal RhD status. RHD sequences were detected in the maternal plasma DNA of 35 subjects and were negative in the maternal plasma of 19 subjects. In 15 of the 19 subjects with negative maternal plasma RHD result, RASSF1A sequences were detected in the plasma DNA after enzymatic digestion. The other 4 cases were negative for RASSF1A after enzymatic digestion. Beta-actin signal was negative in all cases indicating that the BstU I enzyme digestion was complete in all 19 cases. Based on the analysis of the CVS samples, all 15 subjects with positive detection of RASSF1A after enzymatic digestion were carrying a RhD-negative fetus. In the 4 subjects showing negative detection of RHD and RASSF1A in their plasma, the CVS were RHD positive in 2 of them. Thus, for these two cases, maternal plasma RHD genotyping had produced false negative results, which were picked up by the failure to detect the positive analytical marker RASSF1A after enzymatic digestion. To illustrate the importance of this gender independent fetal marker, these results were compared with an existing fetal DNA marker SRY. The SRY assay would be positive only when the fetus is male. For the 19 subjects with negative detection of RHD sequence in their plasma, 6 of them were positive for SRY, indicating the presence of amplifiable fetal DNA in the analyzed maternal plasma sample and thus further confirmed the genuine nature of the RhD-negative status of the fetus. In the remaining 13 cases, whether the negative detection of RHD and SRY sequences in the plasma DNA is a result of a female RhD negative fetus or the inadequate fetal DNA in the maternal plasma cannot be ascertained without using the RASSF1A protocol as a positive control for fetal DNA.

Example 6

Figure 16:
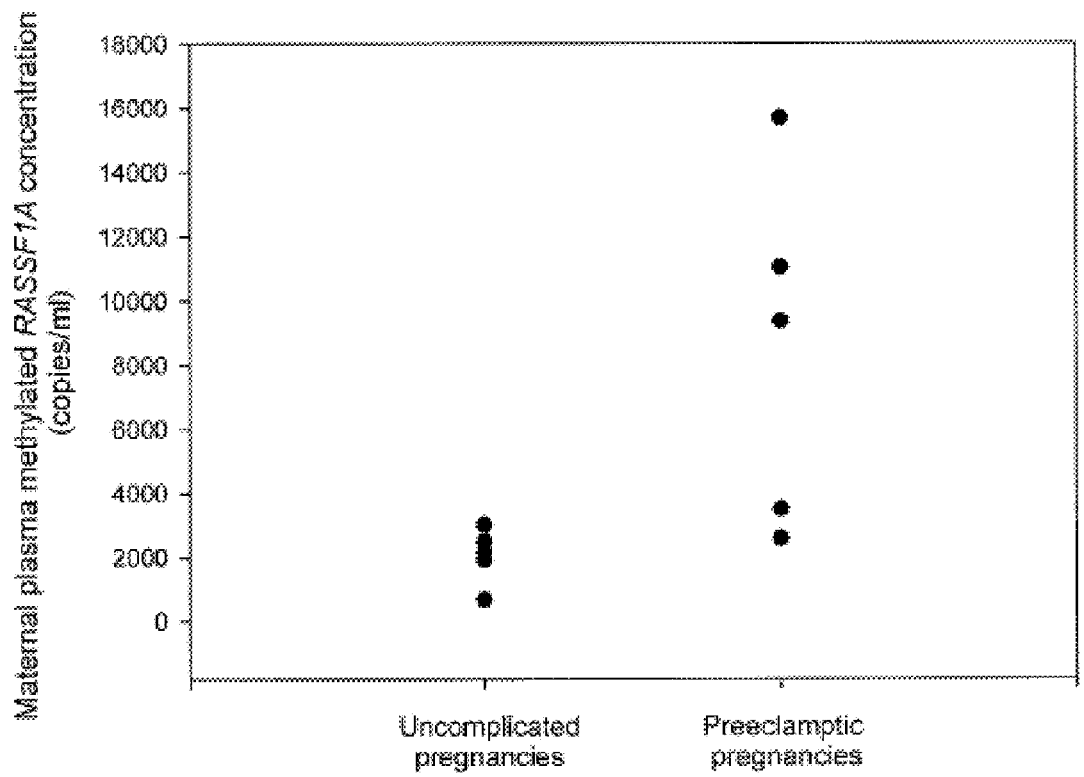
FIG. 16. The concentration of RASSF1A sequence after enzymatic digestion in maternal plasma was elevated in preeclamptic pregnancies.

Demonstration of RASSF1A as a Gender-Independent Marker for Monitoring Preeclampsia The clinical utility of the hypermethylated fetal DNA markers goes beyond serving as a positive analytical marker. The detection and/or quantification of the RASSF1A by itself after enzymatic digestion can be useful in prenatal diagnosis and pregnancy monitoring. In other words, these hypermethylated fetal DNA sequences in maternal plasma can serve as biomarkers by their own right. Previously, it has been demonstrated that fetal DNA concentration in maternal plasma is increased in certain conditions such as preeclampsia and fetal aneuploidies. However, due to the lack of a gender-independent fetal DNA marker, previous studies were limited to pregnant women carrying a male fetus (Levine et al., *Am J Obstet Gynecol* 190:707-713; Leung et al., *Clin Chem* 47:147-139). In this example, we have compared the fetal DNA concentrations in the plasma, by targeting the RASSF1A sequence after enzymatic digestion, of 5 women suffering from preeclampsia with 5 gestational-age matched pregnant women without any pregnancy associated complication. The RASSF1A concentrations measured in the maternal plasma DNA samples after enzymatic digestion of the two groups are shown in FIG. 16. The median concentrations of the pregnant women with and without preeclampsia were 9400 copies/ml and 2200 copies/ml plasma, respectively. The difference between the two groups was statistically significant ($p=0.016$, Mann-Whitney test).

All patents, patent applications, and other publications cited in this application, including published amino acid or polynucleotide sequences, are incorporated by reference in the entirety for all purposes.

TABLE 1

Clearance of RASSF1A and SRY sequences from maternal plasma after delivery. Blood was taken from 5 pregnant women carrying a male fetus just before delivery and 24 hours after delivery. After the maternal plasma DNA samples were treated by the methylation sensitive enzyme, RASSF1A and SRY sequences were detected in the plasma of all subjects before delivery, but were not detectable in any of the plasma samples at 24 hours after delivery.

| | After enzymatic digestion, plasma concentrations of (copies/ml) | | | |
|---|---|---|---|---|
| | RASSF1A | | SRY | |
| Subjects | Before delivery | 24 hours after delivery | Before delivery | 24 hours after delivery |
| A | 84 | 0 | 27 | 0 |
| B | 49 | 0 | 13 | 0 |
| C | 42 | 0 | 15 | 0 |
| D | 23 | 0 | 11 | 0 |
| E | 19 | 0 | 9 | 0 |

TABLE 2

The RASSF1A genotypes of the maternal buffy coat DNA, placental DNA, and maternal plasma DNA with or without enzyme digestion of 43 pregnant women. In each of the 43 cases, the genotype of the maternal plasma DNA with enzyme digestion was identical to the placental (fetal) genotype, suggesting that only fetal-specific DNA molecules were amplifiable after the enzyme digestion of the maternal plasma DNA samples.

| | RASSF1A genotype | | | |
|---|---|---|---|---|
| Case | Maternal buffy coat DNA | Maternal plasma DNA without Digestion | Placental DNA | Maternal plasma DNA with Digestion |
| 616 | CC | CC | CC | CC |
| 677 | AC | AC | AC | AC |
| 688 | AC | AC | CC | CC |
| 695 | CC | CC | CC | CC |
| 832 | AC | AC | CC | CC |
| 849 | AC | AC | CC | CC |
| 873 | AC | AC | AC | AC |
| 920 | AC | AC | AC | AC |
| 928 | AA | AA | AC | AC |
| 1082 | CC | CC | CC | CC |
| 1088 | AC | AC | CC | CC |
| 1089 | AA | AA | AC | AC |
| 1112 | CC | CC | CC | CC |
| 1114 | AA | AA | AA | AA |
| 1145 | AA | AA | AA | AA |
| 1148 | AC | AC | AC | AC |
| 1149 | CC | CC | CC | CC |
| 1155 | AA | AA | AA | AA |
| 1157 | CC | CC | CC | CC |
| 1158 | AC | AC | AA | AA |
| 1170 | CC | CC | CC | CC |
| 1171 | AC | AC | CC | CC |
| 1172 | AC | AC | AC | AC |
| 1182 | CC | CC | CC | CC |
| 1185 | AC | AC | AC | AC |
| 1186 | AC | AC | AA | AA |

TABLE 2-continued

The RASSF1A genotypes of the maternal buffy coat DNA, placental DNA, and maternal plasma DNA with or without enzyme digestion of 43 pregnant women. In each of the 43 cases, the genotype of the maternal plasma DNA with enzyme digestion was identical to the placental (fetal) genotype, suggesting that only fetal-specific DNA molecules were amplifiable after the enzyme digestion of the maternal plasma DNA samples.

| | RASSF1A genotype | | | |
|---|---|---|---|---|
| Case | Maternal buffy coat DNA | Maternal plasma DNA without Digestion | Placental DNA | Maternal plasma DNA with Digestion |
| 1192 | AC | AC | AA | AA |
| 1194 | AC | AC | AC | AC |
| 1195 | CC | CC | CC | CC |
| 1197 | CC | CC | AC | AC |
| 1200 | AC | AC | AC | AC |
| 1203 | AA | AA | AA | AA |
| 1204 | AA | AA | AC | AC |
| 1210 | AC | AC | AC | AC |
| 1211 | CC | CC | AC | AC |
| 1212 | AC | AC | AC | AC |
| 1213 | AC | AC | CC | CC |
| 1214 | AC | AC | CC | CC |
| 1222 | CC | CC | CC | CC |
| 1234 | CC | CC | CC | CC |
| 1235 | CC | CC | CC | CC |
| 1266 | AC | AC | AC | AC |
| 1276 | AA | AA | AA | AA |

What is claimed is:

1. A method for detecting the presence of fetal DNA in a sample from a pregnant woman, comprising the sequential steps of:
   (a) treating a first plasma or serum sample from the woman with an agent that differentially modifies methylated and unmethylated DNA;
   (b) detecting the presence of methylated DNA sequence of RASSF1A in the first sample;
   (c) determining that the sample contains fetal DNA based on the presence of methylated RASSF1A DNA sequence in step (b); and
   (d) when and only when methylated RASSFIA DNA sequence is present in the first sample in step (b), determining the amount of a fetal DNA sequence other than RASSFIA in the same sample or in a second, identical plasma or serum sample from the woman.

2. The method of claim 1, wherein the first sample is a plasma sample.

3. The method of claim 1, wherein the first sample is a serum sample.

4. The method of claim 1, wherein the agent digests unmethylated DNA but not methylated DNA.

5. The method of claim 4, wherein the agent is a methylation sensitive enzyme.

6. The method of claim 5, wherein the methylation sensitive enzyme is a methylation sensitive restriction enzyme.

7. The method of claim 6, wherein the methylation sensitive restriction enzyme is Hpa II or BstU I.

8. The method of claim 1, wherein the agent comprises bisulfite.

9. The method of claim 1, wherein step (b) comprises an amplification process.

10. The method of claim 9, wherein the amplification process is a polymerase chain reaction (PCR).

11. The method of claim 10, wherein the PCR is real-time PCR.

12. The method of claim 1, wherein step (b) further comprises determining the amount of the methylated RASSF1A DNA sequence.

13. The method of claim 1, wherein the first sample and the second sample are the same sample.

14. The method of claim 1, wherein the second sample in step (d) is not treated with any agent that differentially modifies methylated and unmethylated DNA.

15. The method of claim 1, wherein the second sample in step (d) is treated with the agent before the amount of the fetal DNA sequence other than RASSF1A is determined.

16. The method of claim 1, wherein the second sample in step (d) is treated with a second, different agent that differentially modifies methylated and unmethylated DNA before the amount of the fetal DNA sequence other than RASSF1A is determined.

17. The method of claim 1, wherein the fetal DNA sequence other than RASSF1A is a gene of a RhD blood type, of an ABO blood type, of a RhC blood type, of a RhE blood type, of a HLA type, on the Y chromosome, or containing a pre-determined mutation.

18. The method of claim 17, wherein the second sample in step (d) is not treated with any agent that differentially modifies methylated and unmethylated DNA.

19. The method of claim 17, wherein step (d) comprises an amplification process.

20. The method of claim 19, wherein the amplification process is a polymerase chain reaction (PCR).

21. The method of claim 20, wherein the PCR is real-time PCR.

22. The method of claim 1, wherein the fetal DNA sequence other than RASSF1A is distinguished from its maternal counterpart by a difference in sequence or methylation.

* * * * *

SEQUENCE LISTING

<160> NUMBER OF SEQ ID NOS: 38

<210> SEQ ID NO 1
<211> LENGTH: 20
<212> TYPE: DNA
<213> ORGANISM: Artificial Sequence
<220> FEATURE:
<223> OTHER INFORMATION: methylation-specific PCR oligo Ras association
      (Ra1GDS/AF-6) domain family 1 (RASSF1A) RASSF1A-MF
      synthetic forward primer

<400> SEQUENCE: 1
gtgttaacgc gttgcgtatc                                          20

<210> SEQ ID NO 2
<211> LENGTH: 21
<212> TYPE: DNA
<213> ORGANISM: Artificial Sequence
<220> FEATURE:
<223> OTHER INFORMATION: methylation-specific PCR oligo Ras association
      (Ra1GDS/AF-6) domain family 1 (RASSF1A) RASSF1A-MR
      synthetic reverse primer

<400> SEQUENCE: 2 aacccgcga actaaaaacg a                                         21

<210> SEQ ID NO 3
<211> LENGTH: 23
<212> TYPE: DNA
<213> ORGANISM: Artificial Sequence
<220> FEATURE:
<223> OTHER INFORMATION: methylation-specific PCR oligo Ras association
      (Ra1GDS/AF-6) domain family 1 (RASSF1A) RASSF1A-UF
      synthetic forward primer

<400> SEQUENCE: 3
tttggttgga gtgtgttaat gtg                                      23

<210> SEQ ID NO 4
<211> LENGTH: 23
<212> TYPE: DNA
<213> ORGANISM: Artificial Sequence

```
<220> FEATURE:
<223> OTHER INFORMATION: methylation-specific PCR oligo Ras association
      (Ra1GDS/AF-6) domain family 1 (RASSF1A) RASSF1A-UR
      synthetic reverse primer

<400> SEQUENCE: 4
caaaccccac aaactaaaaa caa                                              23

<210> SEQ ID NO 5
<211> LENGTH: 30
<212> TYPE: DNA
<213> ORGANISM: Artificial Sequence
<220> FEATURE:
<223> OTHER INFORMATION: Ras association (Ra1GDS/AF-6) domain family 1
      (RASSF1A) bisulfite sequencing oligo HsPromoter-F
      synthetic forward primer

<400> SEQUENCE: 5
gggttttata gttttttgtat ttaggttttt                                      30

<210> SEQ ID NO 6
<211> LENGTH: 25
<212> TYPE: DNA
<213> ORGANISM: Artificial Sequence
<220> FEATURE:
<223> OTHER INFORMATION: Ras association (Ra1GDS/AF-6) domain family 1
      (RASSF1A) bisulfite sequencing oligo HsPromoter-R
      reverse primer

<400> SEQUENCE: 6
caactcaata aactcaaact ccccc                                            25

<210> SEQ ID NO 7
<211> LENGTH: 24
<212> TYPE: DNA
<213> ORGANISM: Artificial Sequence
<220> FEATURE:
<223> OTHER INFORMATION: Ras association (Ra1GDS/AF-6) domain family 1
      (RASSF1A) bisulfite sequencing oligo HsExon1-F
      synthetic forward primer

<400> SEQUENCE: 7
ggggagtttg agtttattga gttg                                             24

<210> SEQ ID NO 8
<211> LENGTH: 22
<212> TYPE: DNA
<213> ORGANISM: Artificial Sequence
<220> FEATURE:
<223> OTHER INFORMATION: Ras association (Ra1GDS/AF-6) domain family 1
      (RASSF1A) bisulfite sequencing oligo HsExon1-R
      synthetic reverse primer

<400> SEQUENCE: 8 ctaccccta actacccctt cc                                                22

<210> SEQ ID NO 9
<211> LENGTH: 34
<212> TYPE: DNA
<213> ORGANISM: Artificial Sequence
<220> FEATURE:
<223> OTHER INFORMATION: synthetic adenomatosis polyposis coli (APC)
      bisulfite sequencing oligo HsPromoter-F forward primer

<400> SEQUENCE: 9
taatttattt aatattattg ttttttttgtg ttgt                                 34

<210> SEQ ID NO 10
```

```
<211> LENGTH: 26
<212> TYPE: DNA
<213> ORGANISM: Artificial Sequence
<220> FEATURE:
<223> OTHER INFORMATION: synthetic adenomatosis polyposis coli (APC)
      bisulfite sequencing oligo HsPromoter-R reverse primer

<400> SEQUENCE: 10
caccctaacr aactacacca atacaa                                          26

<210> SEQ ID NO 11
<211> LENGTH: 30
<212> TYPE: DNA
<213> ORGANISM: Artificial Sequence
<220> FEATURE:
<223> OTHER INFORMATION: synthetic retinoic acid receptor, beta (RARB)
      bisulfite sequencing oligo HsRARBPromoter-F forward primer

<400> SEQUENCE: 11
gtaggyggaa tatygttttt taagttaagt                                      30

<210> SEQ ID NO 12
<211> LENGTH: 32
<212> TYPE: DNA
<213> ORGANISM: Artificial Sequence
<220> FEATURE:
<223> OTHER INFORMATION: synthetic retinoic acid receptor, beta (RARB)
      bisulfite sequencing oligo HsRARBPromoter-R reverse primer

<400> SEQUENCE: 12
acttcctact acttctatca cacaaaataa aa                                   32

<210> SEQ ID NO 13
<211> LENGTH: 32
<212> TYPE: DNA
<213> ORGANISM: Artificial Sequence
<220> FEATURE:
<223> OTHER INFORMATION: synthetic retinoic acid receptor, beta (RARB)
      bisulfite sequencing oligo HsRARBExon1-F forward primer

<400> SEQUENCE: 13
ttttattttg tgtgatagaa gtagtaggaa gt                                   32

<210> SEQ ID NO 14
<211> LENGTH: 28
<212> TYPE: DNA
<213> ORGANISM: Artificial Sequence
<220> FEATURE:
<223> OTHER INFORMATION: synthetic retinoic acid receptor, beta (RARB)
      bisulfite sequencing oligo HsRARBExon1-R reverse primer

<400> SEQUENCE: 14
aatcatttac cattttccaa acttactc                                        28

<210> SEQ ID NO 15
<211> LENGTH: 22
<212> TYPE: DNA
<213> ORGANISM: Artificial Sequence
<220> FEATURE:
<223> OTHER INFORMATION: methylation-specific PCR oligo caspase 8,
      apoptosis-related cysteine peptidase (CASP8)
      CASP8-MF forward primer

<400> SEQUENCE: 15
ggttagggga ttcggagatt gc                                              22

<210> SEQ ID NO 16
<211> LENGTH: 29
```

```
<212> TYPE: DNA
<213> ORGANISM: Artificial Sequence
<220> FEATURE:
<223> OTHER INFORMATION: methylation-specific PCR oligo caspase 8,
      apoptosis-related cysteine peptidase (CASP8)
      CASP8-MR synthetic reverse primer

<400> SEQUENCE: 16
aaaaaaaccg tatatctaca ttcgaaacg                                    29

<210> SEQ ID NO 17
<211> LENGTH: 25
<212> TYPE: DNA
<213> ORGANISM: Artificial Sequence
<220> FEATURE:
<223> OTHER INFORMATION: caspase 8, apoptosis-related cysteine peptidase
      (CASP8) bisulfite sequencing oligo HsExon1-F
      synthetic forward primer

<400> SEQUENCE: 17
agggaagtgt ttttataggt ttttt                                        25

<210> SEQ ID NO 18
<211> LENGTH: 29
<212> TYPE: DNA
<213> ORGANISM: Artificial Sequence
<220> FEATURE:
<223> OTHER INFORMATION: caspase 8, apoptosis-related cysteine peptidase
      (CASP8) bisulfite sequencing oligo HsExon1-R
      synthetic reverse primer

<400> SEQUENCE: 18
ataatttcct attaaaaaaa ccaccttaa                                    29

<210> SEQ ID NO 19
<211> LENGTH: 21
<212> TYPE: DNA
<213> ORGANISM: Artificial Sequence
<220> FEATURE:
<223> OTHER INFORMATION: methylation-specific PCR oligo secretoglobulin,
      family 3A, member 1 (SCGB3A1) SCGB3A1-MF synthetic
      forward primer

<400> SEQUENCE: 19
tttagttttg taggggggcg c                                            21

<210> SEQ ID NO 20
<211> LENGTH: 24
<212> TYPE: DNA
<213> ORGANISM: Artificial Sequence
<220> FEATURE:
<223> OTHER INFORMATION: methylation-specific PCR oligo secretoglobulin,
      family 3A, member 1 (SCGB3A1) SCGB3A1-MF synthetic
      forward primer

<400> SEQUENCE: 20
accaacttcc tactacgacc gacg                                         24

<210> SEQ ID NO 21
<211> LENGTH: 25
<212> TYPE: DNA
<213> ORGANISM: Artificial Sequence
<220> FEATURE:
<223> OTHER INFORMATION: secretoglobulin, family 3A, member 1 (SCGB3A1)
      bisulfite sequencing oligo Hspromoter-F synthetic
      forward primer

<400> SEQUENCE: 21
gattagaggt agggattagg gagtt                                        25
```

<210> SEQ ID NO 22
<211> LENGTH: 24
<212> TYPE: DNA
<213> ORGANISM: Artificial Sequence
<220> FEATURE:
<223> OTHER INFORMATION: secretoglobulin, family 3A, member 1 (SCGB3A1)
      bisulfite sequencing oligo Hspromoter-R synthetic
      reverse primer

<400> SEQUENCE: 22
taacaaacrc taaaccctc taaa                                         24

<210> SEQ ID NO 23
<211> LENGTH: 19
<212> TYPE: DNA
<213> ORGANISM: Artificial Sequence
<220> FEATURE:
<223> OTHER INFORMATION: methylation-specific PCR oligo DOC-2/DAB2
      interacting protein (DAB2IP) DAB2IP-MF synthetic
      forward primer

<400> SEQUENCE: 23
gtaagggtgc gggtttcgc                                              19

<210> SEQ ID NO 24
<211> LENGTH: 23
<212> TYPE: DNA
<213> ORGANISM: Artificial Sequence
<220> FEATURE:
<223> OTHER INFORMATION: methylation-specific PCR oligo DOC-2/DAB2
      interacting protein (DAB2IP) DAB2IP-MR synthetic
      reverse primer

<400> SEQUENCE: 24
gaactcacct ctcattatcc gcg                                         23

<210> SEQ ID NO 25
<211> LENGTH: 28
<212> TYPE: DNA
<213> ORGANISM: Artificial Sequence
<220> FEATURE:
<223> OTHER INFORMATION: DOC-2/DAB2 interacting protein (DAB2IP)
      bisulfite sequencing oligo HsExon1-F forward primer

<400> SEQUENCE: 25 aagggttta ttaagygtat taagagtt                                    28

<210> SEQ ID NO 26
<211> LENGTH: 20
<212> TYPE: DNA
<213> ORGANISM: Artificial Sequence
<220> FEATURE:
<223> OTHER INFORMATION: DOC-2/DAB2 interacting protein (DAB2IP)
      bisulfite sequencing oligo HsExon1-R synthetic reverse primer

<400> SEQUENCE: 26
accccraaaa aaaacacaaa                                             20

<210> SEQ ID NO 27
<211> LENGTH: 20
<212> TYPE: DNA
<213> ORGANISM: Artificial Sequence
<220> FEATURE:
<223> OTHER INFORMATION: synthetic RASSF1A real-time PCR forward primer
      RSF-b151F

<400> SEQUENCE: 27
agcctgagct cattgagctg                                                 20

<210> SEQ ID NO 28
<211> LENGTH: 16
<212> TYPE: DNA
<213> ORGANISM: Artificial Sequence
<220> FEATURE:
<223> OTHER INFORMATION: synthetic RASSF1A real-time PCR reverse primer
      RSF-dsgnR

<400> SEQUENCE: 28
accagctgcc gtgtgg                                                     16

<210> SEQ ID NO 29
<211> LENGTH: 16
<212> TYPE: DNA
<213> ORGANISM: Artificial Sequence
<220> FEATURE:
<223> OTHER INFORMATION: RASSF1A real-time PCR minor groove binding
      (MGB) synthetic fluorescent probe RSF-dsgnT
<220> FEATURE:
<221> NAME/KEY: modified_base
<222> LOCATION: (1)...(1)
<223> OTHER INFORMATION: n = c modified by FAM
<220> FEATURE:
<221> NAME/KEY: modified_base
<222> LOCATION: (16)...(16)
<223> OTHER INFORMATION: n = t modified by minor groove binder (MGB)

<400> SEQUENCE: 29
ncaacgcgct gcgcan                                                     16

<210> SEQ ID NO 30
<211> LENGTH: 17
<212> TYPE: DNA
<213> ORGANISM: Artificial Sequence
<220> FEATURE:
<223> OTHER INFORMATION: synthetic beta-actin real-time PCR forward
      primer Actin-163F

<400> SEQUENCE: 30
gcgccgttcc gaaagtt                                                    17

<210> SEQ ID NO 31
<211> LENGTH: 15
<212> TYPE: DNA
<213> ORGANISM: Artificial Sequence
<220> FEATURE:
<223> OTHER INFORMATION: synthetic beta-actin real-time PCR reverse
      primer Actin-298R

<400> SEQUENCE: 31
cggcggatcg gcaaa                                                      15

<210> SEQ ID NO 32
<211> LENGTH: 17
<212> TYPE: DNA
<213> ORGANISM: Artificial Sequence
<220> FEATURE:
<223> OTHER INFORMATION: synthetic beta-actin real-time PCR minor
      groove binding (MGB) fluorescent probe Actin-243T
<220> FEATURE:
<221> NAME/KEY: modified_base
<222> LOCATION: (1)...(1)
<223> OTHER INFORMATION: n = a modified by VIC
<220> FEATURE:
<221> NAME/KEY: modified_base
<222> LOCATION: (17)...(17)
<223> OTHER INFORMATION: n = c modified by minor groove binder (MGB)

<400> SEQUENCE: 32
nccgccgaga ccgcgtn                                                        17

<210> SEQ ID NO 33
<211> LENGTH: 21
<212> TYPE: DNA
<213> ORGANISM: Artificial Sequence
<220> FEATURE:
<223> OTHER INFORMATION: Y-chromosome sex-determining region Y (SRY)
      Synthetic real-time PCR forward amplification
      primer SRY-109F

<400> SEQUENCE: 33
tggcgattaa gtcaaattcg c                                                   21

<210> SEQ ID NO 34
<211> LENGTH: 25
<212> TYPE: DNA
<213> ORGANISM: Artificial Sequence
<220> FEATURE:
<223> OTHER INFORMATION: Y-chromosome sex-determining region Y (SRY)
      synthetic real-time PCR reverse amplification
      primer SRY-245R

<400> SEQUENCE: 34 cccctagta ccctgacaat gtatt                                                25

<210> SEQ ID NO 35
<211> LENGTH: 26
<212> TYPE: DNA
<213> ORGANISM: Artificial Sequence
<220> FEATURE:
<223> OTHER INFORMATION: Y-chromosome sex-determining region Y (SRY)
      real-time PCR minor groove binding (MGB)
      synthetic fluorescent probe SRY-142T
<220> FEATURE:
<221> NAME/KEY: modified_base
<222> LOCATION: (1)...(1)
<223> OTHER INFORMATION: n = a modified by FAM
<220> FEATURE:
<221> NAME/KEY: modified_base
<222> LOCATION: (26)...(26)
<223> OTHER INFORMATION: n = a modified by TAMRA

<400> SEQUENCE: 35
ngcagtagag cagtcaggga ggcagn                                              26

<210> SEQ ID NO 36
<211> LENGTH: 16
<212> TYPE: DNA
<213> ORGANISM: Artificial Sequence
<220> FEATURE:
<223> OTHER INFORMATION: synthetic RASSF1A extension primer Rsf-R17

<400> SEQUENCE: 36
cagccgggtg ggccct                                                         16

<210> SEQ ID NO 37
<211> LENGTH: 17
<212> TYPE: DNA
<213> ORGANISM: Artificial Sequence
<220> FEATURE:
<223> OTHER INFORMATION: synthetic RASSF1A genotype A primer extension
      reaction product
<220> FEATURE:
<221> NAME/KEY: modified_base
<222> LOCATION: (17)...(17)
<223> OTHER INFORMATION: n = dideoxythymidine

<400> SEQUENCE: 37

-continued

```
cagccgggtg ggccctn                                                    17

<210> SEQ ID NO 38
<211> LENGTH: 18
<212> TYPE: DNA
<213> ORGANISM: Artificial Sequence
<220> FEATURE:
<223> OTHER INFORMATION: synthetic RASSF1A genotype C primer extension
      reaction product
<220> FEATURE:
<221> NAME/KEY: modified_base
<222> LOCATION: (18)...(18)
<223> OTHER INFORMATION: n = dideoxycytidine

<400> SEQUENCE: 38
cagccgggtg ggccctgn                                                   18
```